US007912733B2

(12) United States Patent
Clements et al.

(10) Patent No.: US 7,912,733 B2
(45) Date of Patent: Mar. 22, 2011

(54) SYSTEM, METHOD AND PROGRAM PRODUCT FOR DELIVERING MEDICAL SERVICES FROM A REMOTE LOCATION

(75) Inventors: Leon M. Clements, League City, TX (US); Jason Calhoun, Columbia, MO (US); Glenn G. Hammack, Houston, TX (US); Oscar Boultinghouse, Friendswood, TX (US); Kaye S. Cloutier, Nassau Bay, TX (US); Michael J. Davis, Bellaire, TX (US); William Whipkey, Houston, TX (US); Oliver M. Black, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1232 days.

(21) Appl. No.: 11/415,936

(22) Filed: May 2, 2006
(Under 37 CFR 1.47)

(65) Prior Publication Data
US 2006/0271400 A1  Nov. 30, 2006

Related U.S. Application Data

(60) Provisional application No. 60/677,709, filed on May 4, 2005.

(51) Int. Cl.
*G06Q 10/00*  (2006.01)
(52) U.S. Cl. ......................................................... 705/2
(58) Field of Classification Search .................. 600/301; 705/1, 2, 3, 20
See application file for complete search history.

(56) References Cited

U.S. PATENT DOCUMENTS

| 4,857,713 A | 8/1989 | Brown |
| 5,291,399 A | 3/1994 | Chaco |

(Continued)

FOREIGN PATENT DOCUMENTS

EP          0510 615 A      10/1992

(Continued)

OTHER PUBLICATIONS

UTMB Correctional Managed Care uses Cyb-R Care to provide remote physician services across the State of Texas, Booth Presentation, May 10, 2001.

(Continued)

*Primary Examiner* — Gerald J. O'Connor
*Assistant Examiner* — Teresa Woods
(74) *Attorney, Agent, or Firm* — Bracewell & Giuliani LLP

(57) ABSTRACT

A system, program product, and methods related to enhanced medical services delivery to geographically distributed patient populations by remotely located physicians are provided. An embodiment of the system includes a remote medical services server, a plurality of patient electronic medical records stored in the memory of the remote medical services server, and a remote medical services program product stored in the memory of the remote medical services server adapted to access the plurality of patient electronic medical records to thereby allow display of and data entry in a selected patient electronic medical record. A patient medical service delivery station captures patient video images and displays remote physician video images. A remote physician medical service delivery suite in communication with the patient medical service delivery station through the communications network captures remote physician video images and displays patient video images and patient electronic medical records, to allow the remote physician to perform remote patient medical service delivery.

42 Claims, 28 Drawing Sheets

U.S. PATENT DOCUMENTS

| | | | |
|---|---|---|---|
| 5,544,649 A * | 8/1996 | David et al. | 600/301 |
| 5,619,991 A | 4/1997 | Sloane | |
| 5,701,904 A * | 12/1997 | Simmons et al. | 600/301 |
| 5,758,095 A | 5/1998 | Albaum et al. | |
| 5,911,132 A | 6/1999 | Sloane | |
| 6,369,847 B1 | 4/2002 | James et al. | |
| 7,129,970 B2 | 10/2006 | James et al. | |
| 2004/0230458 A1 * | 11/2004 | Takayama et al. | 705/3 |
| 2007/0118389 A1 * | 5/2007 | Shipon | 705/1 |

FOREIGN PATENT DOCUMENTS

| | | |
|---|---|---|
| EP | 1 237 113 A | 9/2002 |
| WO | WO 99/41014 A | 8/1999 |
| WO | WO 2004/015602 A2 | 2/2004 |

OTHER PUBLICATIONS

Towards the Electronic Patient Record (TEPR), Using the Electronic Medical Record to Support Telemedicine, May 11, 2001.

Telemedicine, An Introduction, Review, and Considerations, HI 2001, May 16, 2001.

American Telemedicine Association (ATA), PowerPoint Presentation, Fort Lauderdale, Florida Jun. 5, 2001.

Business Computer Applications and the University of Texas Medical Branch Correctional Managed Care welcomes Representatives of the U.S. Federal Bureau of Prisons Washington, D.C., Aug. 14, 2001.

Digital Medical Services Telemedicine/EMR Update, VA-HHS, Aug. 15, 2001.

Digital Medical Services Telemedicine/EMR Update, ACA Philly, Aug. 23, 2001.

Digital Medical Services Technology Overview, Enron, Sep. 6, 2001.

Allen, John, UTMB Correctional Managed Care Private Prison Presentation, www.digitalmedicalservices.com, Private Prisons, Dec. 12, 2001.

Using the Emerald Reports Screens, Dec. 19, 2001.

UTMB Electronic Medical Records and Telemedicine in the Correctional Environment, www.digitalmedicalservices.com, American Correctional Association, Workshop A-2, San Antonio, Jan. 12, 2002. Same as above—Pfizer 2002, Jan. 13, 2002.

UTMB State of the Art Telemedicine and Electronic Medical Records in the Corrections, www.digitalmedicalservices.com, American Correctional Health Services Association (ACHSA), Portland, Oregon, Mar. 16, 2002.

UTMB Digital Medical Services, Overview, Federal Bureau of Prisons Visitors, www.digitalmedicalservices.com, Mar. 27, 2002.

UTMB Digital Medical provides remote physician services across the state of Texas, Digital Medical Services (DMS) Booth 2, May 14, 2002.

Towards the Electronic Patient Record (TEPR), UTMB Correctional Managed Care Information Services, Design and Performance of the UTMB CMC Statewide EMR System, May 14, 2002.

UTMB Correctional Managed Care Uses +DMS to provide remote physican service across the state of TX, Jun. 3, 2002.

UTMB Correctional Managed Care Information Services, Future Management of EMR Implementation and Development, A Proposal to CMC Administration, Summer Quarterly Management Meeting, Open Gates, Galveston, Texas, Jul. 10, 2002.

UTMB Correctional Managed Care Information Services, The Primary Care Studio in Galveston, Texas, Administration Systems, Aug. 14, 2002.

UTMB Correctional Managed Care Information Services, Optometric Education of the Future Telemedicine, American Society of Clinical Oncology (ASCO) Telemed, Oct. 4, 2002.

UTMB Correctional Managed Care Information Services, A Common Electronic Medical Record for TDCJ Unit Clinics, Tech Lubbock, Oct. 18, 2002.

UTMB Correctional Managed Care Uses +DMS to provide remote physican service across the state of TX, +DMS Booth Presentation LMC, Oct. 27, 2002.

UTMB Correctional Managed Care Uses +DMS to provide remote physican service across the state of TX, www.digitalmedicalservices.com, +DMS Booth, Jan. 29, 2003.

UTMB Correctional Managed Care (CMC) Electronic Medical Record (EMR) and Digital Medical Services (DMS), Dallas County Commissioners, Mar. 26, 2003.

UTMB Correctional Managed Care Uses +DMS to provide remote physician service across the state of TX, www.digitalmedicalservices.com, +DMS Booth, Aug. 12, 2003.

UTMB Correctional Managed Care (CMC) Information Systems, Electronic Medical Record (EMR) and Digital Medical Services (DMS), www.digitalmedicalservices.com, Centers for Disease Control (CDC) Business Computer Applications (BCA), Sep. 9, 2003.

UTMB Correctional Managed Care (CMC) Information Systems, Real IP Telemedicine: A Sustained Model, www.digitalmedicalservices.com, Polycom TM, Oct. 7, 2003.

UTMB Correctional Managed Care (CMC) Information Systems, The Role of the Community Physician in the Evolving Landscape of e-Health or How We Fit Primary Care Services into an Active, Sustained Telemedicine Practice, www.digitalmedicalservices.com, Nov. 10, 2003.

UTMB Telemedicine in Managed Care, www.digitalmedicalservices.com,, Nov. 11, 2003.

Electronic Medical Records (EMR) Leadership Retreat, Texas Tech Kickoff Leadership, Huntsville, Texas, Dec. 16, 2003.

Studio Spinners, Apr. 10, 2004.

UTMB Correctional Managed Care (CMC) Information Systems, Digital Medical Systems (DMS) Cardiology, American Telemedicine Association (ATA) Cardio, Apr. 16, 2004.

UTMB Correctional Managed Care (CMC) Information Systems, Telemedicine (TM) Nuts and Bolts, Correctional Health Long Course, American Telemedicine Association (ATA) May 2, 2004.

Clements, et al., Presentation on "CyberCare A Medical Delivery System for the Future," Presented at National Healthcare Congress, Miami Fl. Nov. 6, 1999.

Article titled Innovative Programs in Telemedicine, University of Texas Medical Branch at Galveston Electronic Network, Telemedicine and e-Health, vol. 11, No. 2, 2005.

Bouabène, A, Article titled "Providing Emergency Medical Care to Offshore Oil and Gas Platforms in the Gulf of Mexico Using Telemedicine," Applications of Broadband Optical and Wireless Networks, Proceedings of SPIE, vol. 4912 (2002) XP-002396166.

Rainer, B., et al., "Health Care Delivery in the Texas Prison System, The Role of Academic Medicine, JAMA ," Journal of American Medical Association, Jul. 28, 2004, pp. 485-489, vol. 292, No. 4, U.S.

J. Carmenates, et al.: "Impact of Automation on Pharmacist Interventions and Medication Errors in a Correctional Health Care System," Journal of the American Society of Health.

P Bonnabry: "Information Technologies for the Prevention of Medication," Business Briefing: European Pharamcotherapy 2003, 'Online' 2003, pp. 1-5.

The University of Texas Medical Branch v. Emtel, Inc., Civil Action H-03-0889, Complaint for Declaratory Judgment. filed Mar. 11, 2003, United States District Court, Southern District of Texas, Houston Division.

Letter dated Sep. 13, 2002, from Emtel, Inc. to UTMB and P& O Cruise Lines, regarding Emtel patent 6,369,847.

UTMB, Electronic Health Network, Remote Physician Services Telemedicine Proposal, Jul. 14, 2005.

UTMB, The University of Texas Medical Branch, Telemedicine, Digital Medical Services, and The UTMB Electronic Health Network presentation, Mar. 2005.

John D. Stobo, MD; Telemedicine: The Future of Health Care; The University of Texas Medical Branch at Galveston; Energy Houston; 2002; pp. 92-96; vol. 4 No. 2; Houston, Texas.

Ben G. Raimer, MD; John D. Stobo, MD; Health Care Delivery in the Texas Prison System The Role of Academic Medicine; JAMA; 2004; pp. 485-489; vol. 292, No. 4.

Eric Berger; Inmate health care now up to standard; Report says privatization has helped the state better conditions; Jul. 28, 2004; Section B p. 1 Metfront; Houston, Texas.

Monica Perin; Online health care database headed to Texas; Houston Business Journal; Aug. 2007.

Lynn Cook Virtual care, real profit?; Houston Chronicle; 2007.

Dr. Glenn Hammack; Redefining Telemedicine; Health Management Technology; Oct. 2006.

Mary Ann Azevedo; Medical firm ready for national break-out; Houston Business Journal; Jan. 2006; pp. 55-57.

US States News; Galveston's West End Receiving University of Texas Medical Branch 'House Calls'; Jun. 2006; pp. 53-54.

Robert Stanton; Care made easy; Telehealth pilot program kicks off on west end of Galveston Island The; The Houston Chronicle; Jul. 2006; pp. 51-52.

Dr. Glenn Hammack; Redefining Telemedicine; Health Management Technology; Oct. 2006; pp. 47-50.

US States News; Grant Brings Mental Health Care to Schools; Galveston, Texas; Oct. 2006; pp. 45-46.

US States News; Rift Valley Fever Patient in Eastern Africa Examined by University of Texas's Medical Branch Experts via Real-Time, Telemedicine Connection; Galveston, Texas; Jan. 2007; pp. 42-44.

Monica Perin; UTMB, Sanders Morris Harris launch telemedicine company; Houston Business Journal; Aug. 2007; p. 41.

Lynn Cook; Health; UTMB, an innovator in the field of telemedicine, wants to make the process a commercial enterprise; Virtual care, real profit?; The Houston Chronicle; Aug. 2007; pp. 38-40.

UTMB; School among nation's tops in funding; The Houston Chronicle; Oct. 2007; pp. 36-37.

UTMB; Telemedicine program captures national award; The Houston Chronicle; Mar. 2008; pp. 34-35.

Targeted News Service; Lawmakers, Health Care Leaders to Hear about University of Texas Medical Branch's success with Telemedicine Initiatives; Galveston, Texas; May 2008; pp. 32-33.

Megan Sowder-Staley; Study; Telehealth Programs Can Slash Billions in Health Care Costs; Congressional Quarterly HealthBeat; Jun. 2008; pp. 30-31.

InPlace Medical Solutions Announces Advanced Medical Services for Offshore and Remote Locations; PR Newswire; Feb. 2009; pp. 23-29.

Is There a Doctor on the Line?; Targeted News Service; Galveston, Texas; Oct. 2009; pp. 20-22.

Alexander H. Vo, et al.; University of Texas Medical Branch telemedicine disaster response and recovery; lessons learned from hurricane Ike; Brief Communication; Report Telemedicine and e-Health; Jun. 2010; pp. 11-19.

Anscombe, D.L.; Healthcare delivery for oil rig workers: telemedicine plays a vital role; Medical Connectivity; Jul. 2010; pp. 4-10.

Telemedicine; Scientists at University of Texas Medical Branch publish new data on telemedicine; Education Letter; Dec. 2010; pp. 1-3.

EP-Summons to Attend Oral Hearing dated Sep. 6, 2010, in related European Application No. 06759017.4.

EP-Examination Report dated Jun. 6, 2008, in related European Application No. 06759017.4.

International Search Report dated Dec. 4, 2006, issued for related PCT patent application No. PCT/US2006/017068.

Kenrick, Mark, Response to Summons to Attend Oral Proceedings, including main request, first auxiliary request & second auxiliary request, pp. 31 (Nov. 5, 2010).

Davis, Michael J, Affidavit, pp. 1-3 (Nov. 4, 2010).

McLaughlin, Vanessa L., MPH, Affidavit, pp. 1-4 (Nov. 4, 2010).

Examination Report cited in co-pending European Patent Application Serial No. 06759017.4 dated Dec. 16, 2010.

Minutes of Oral Proceedings in co-pending European Patent Application Serial No. 06759017.4 dated Dec. 16, 2010.

* cited by examiner

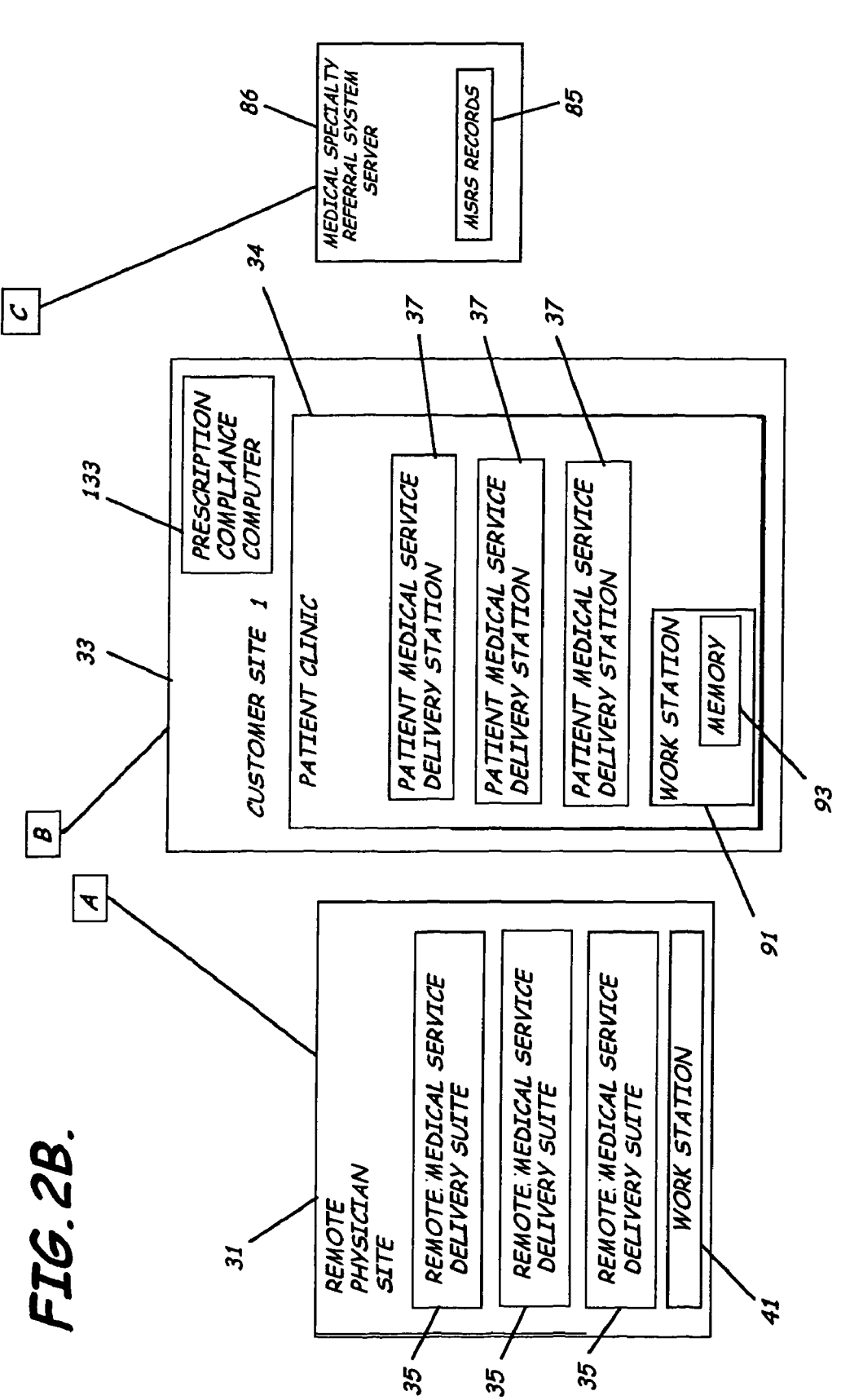

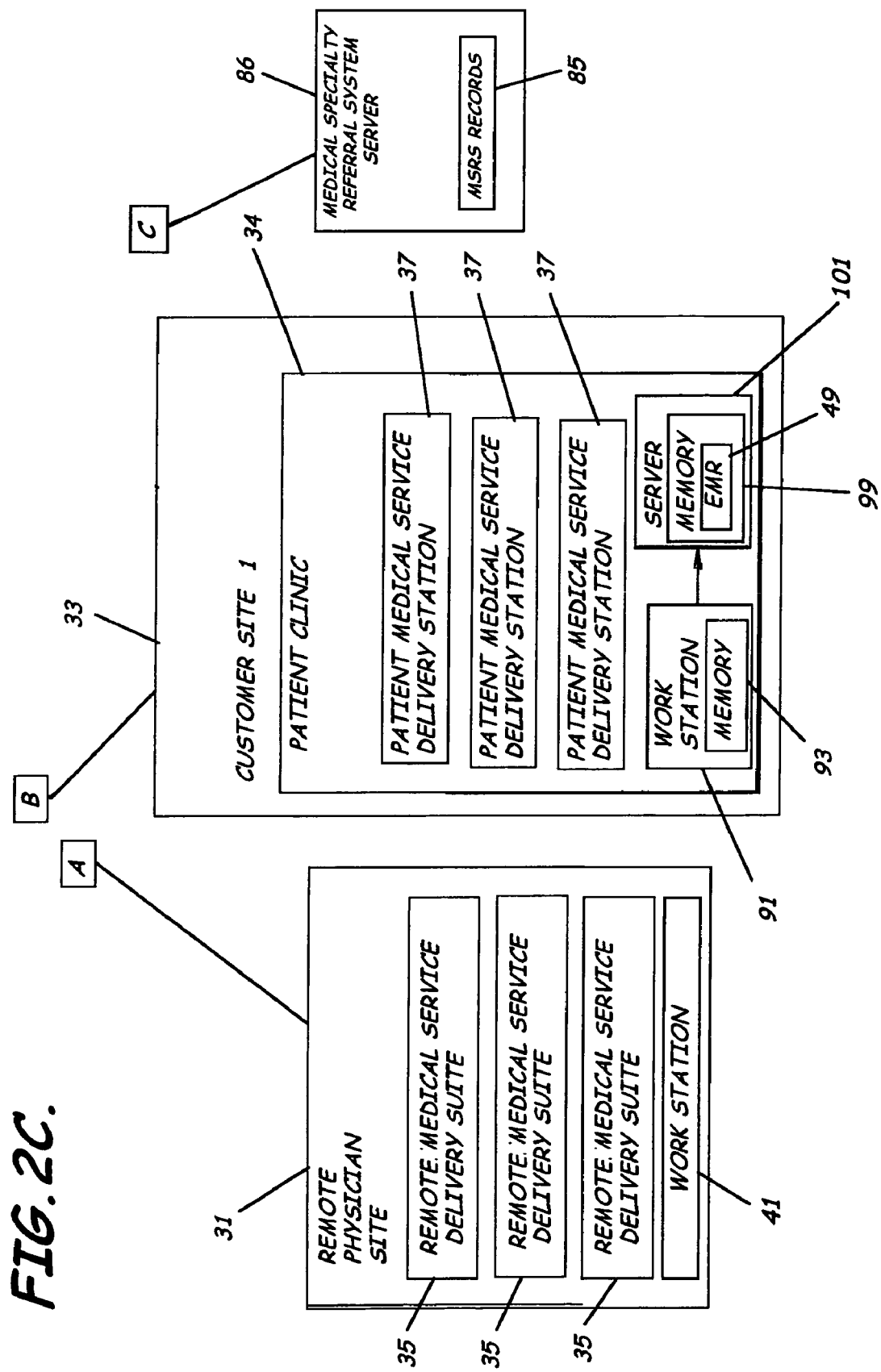

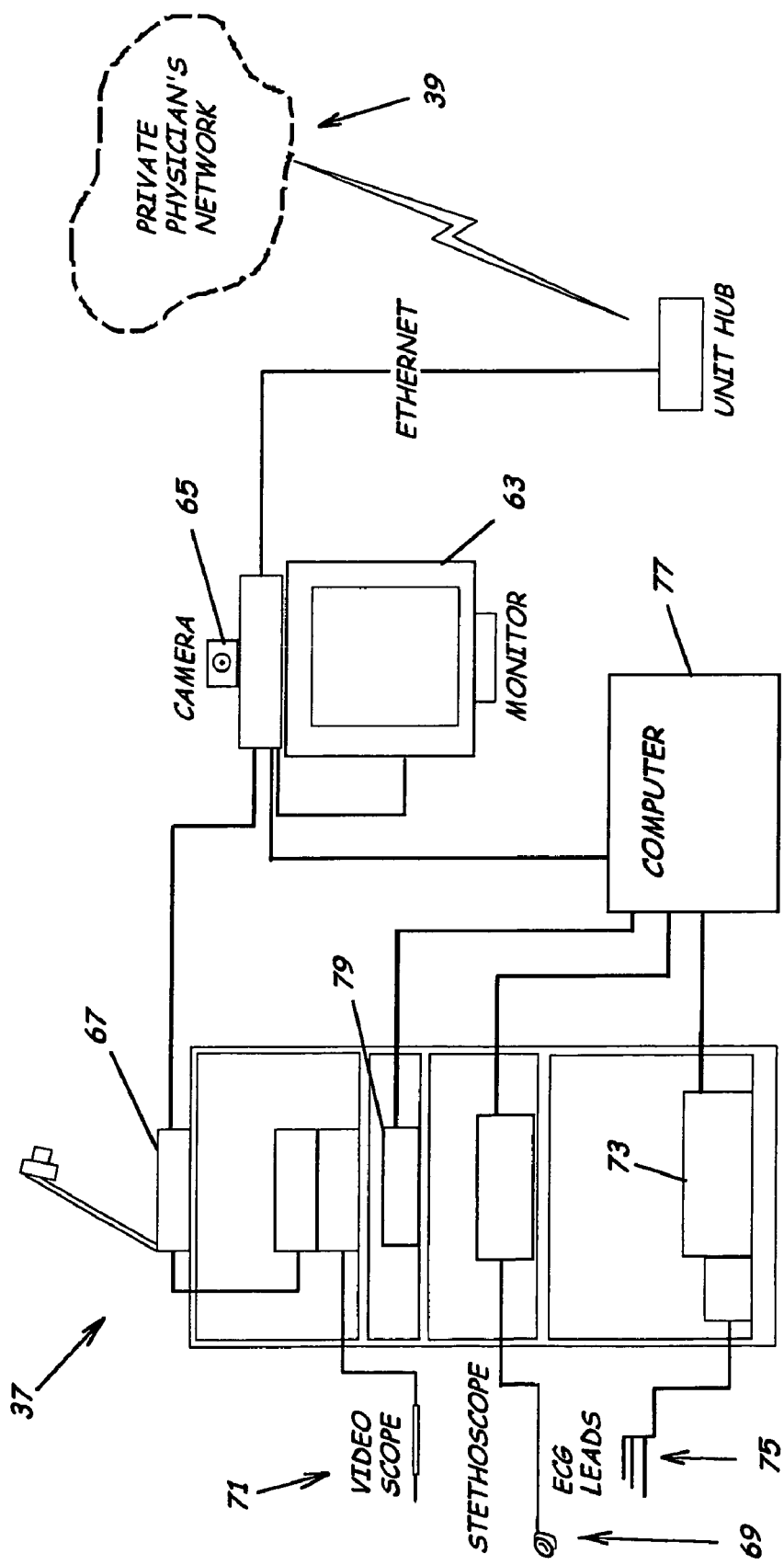

SYSTEM, METHOD AND PROGRAM PRODUCT FOR DELIVERING MEDICAL SERVICES FROM A REMOTE LOCATION

RELATED APPLICATIONS

This is a non-provisional patent application, which claims priority from and the benefit of U.S. Provisional Patent Application No. 60/677,709, filed May 4, 2005, titled "System, Method and Program Product for Delivering Medical Services From A Remote Location", and which is incorporated herein by reference in its entirety.

BACKGROUND OF THE INVENTION

1. Field of the Invention

The present invention relates to medical service industries and more specifically, to systems, methods, and program products for delivering medical services from remote locations.

2. Description of the Related Art

Typically, when a person suffers an illness or injury, that person must have transportation to a medical facility for diagnosis and treatment of the illness or injury. Managed healthcare is an important service provided to various non-medical facilities or institutions, such as, for example, correctional facilities, remote military or scientific bases, and large ships e.g. factory and cruise ships, etc., that have a patient clinic and/or a patient infirmary. Most of such facilities do not, however, have the internal resources to fully provide for all the branches of patient care. Further, smaller communities may be unable to afford a properly staffed medical facility or hospital, may not have enough of a population to support various medical specialties typically serviced by specialist physicians, or may have both adequate funding and population but nevertheless may have an inadequately staffed medical facilities due to physician recruiting difficulties.

In less modern times, the delivery of medical services did not require the level of training and education that is required today. For example, historically, most severing wound infections were treated through amputation rather than application of a regiment of antibiotics and/or localized surgery. Due to the advances in modern medicine, the number of illnesses and injuries that can now be treated have significantly increased while the number of properly trained in educated physicians, especially specialist physicians, have not kept pace. As a result, the difficulty of providing timely and cost efficient patient access to such medical professionals has become increasingly complicated, especially in the various non-medical facilities, institutions, and communities, described above, that are unable to support their own fully staffed hospital staffed with a sufficient number of physicians to provide adequate coverage for each medical specialty.

For this reason, facilities such as, for example, most large correctional facilities, outsource healthcare to external entities. Other facilities, such as smaller correctional facilities, remote military bases, and the various types of ships, along with small communities, generally either outsource healthcare to the external entities or contract with the external entities to have the requisite medical professionals visit their facilities to perform their respective medical services. Even through the use of outsourcing and the use of external contracts, generally there is still an insufficient pool of specialist physicians. Further, even when there is adequate physician resources, under normal conditions, there is generally an insufficient pool of substitute physicians to provide coverage where a physician is sick or otherwise unable to service his or her appointment schedule.

Also, even when a substitute physician or specialist physician is available, a significant amount of such physician's time is wasted in transporting the physicians between their "home" location and the location of the patient. Thus, patients often either need to be transported great distances in order to obtain such services, maximizing the available time of the physician, or the physician is transported to the patients, the result being a fewer number of patients are provided service than would otherwise be, corresponding to the time delay in transporting the physician to the patients.

The concept of telemedicine has been in existence for several years and is used widely throughout the country. Such systems, however, are difficult to use, provide poor imaging quality, and either do not provide for real-time feedback between the patient and physician or provide insufficient feedback such that it can not be considered a sufficient substitute for an in-person scheduled routine visit. Further, because telemedicine in its current form does not properly integrate the use of electronic medical records, pharmacy formularies, or medical protocols that reduce the need for discretion on the part of a patient care provider, they provide for an ineffective and non-standardized utilization of the physician resources. Still further, because such systems tend to be implemented either ad hoc, provide block-time physician availability, or are merely established to monitor a patient's condition without real-time patient-physician interactivity, they do not lend themselves to provide cost efficient utilization and prioritization of a remotely positioned physician's available time. Stated another way, they do not provide a physician centered system for delivering healthcare, and thus, ineffectively utilize limited physician resources; the result being difficulty in a patient obtaining desired medical services and increased costs in obtaining such service, when available.

Thus, there is a need for an integrated healthcare delivery system that brings healthcare to the patient rather than the patient to healthcare by utilizing 21st century technology. Particularly, there is a need for an integrated healthcare delivery system capable of providing medical services delivery to a patient by a remotely separated physician of such quality and functionality that it can be considered an equivalent if not superior substitute for an in-person consultation. Further, there is a need for an integrated healthcare delivery system that integrates the concept of telemedicine with electronic medical technology, medical protocols, and electronic billing to provide healthcare to patients anytime and anywhere from a remote facility and in both a resource efficient and a cost efficient manner.

In addition to the need for such an integrated healthcare delivery system that provides for communication between the physician and the patient, federal regulations, such as the Health Insurance Portability and Accountability Act (HIPAA), related to confidentiality and privacy of individual health records, have created an additional complicating factor for those involved in dealing with medical records in the provision of medical services. The medical records, whether in paper or electronic form, are required to be kept confidential and safeguards are required to be taken to protect such records. For example, many providers have a stated policy prohibiting transfer of information related to an individual's medical record by facsimile transmission because they do not deem this to be a secure transmittal method. Security measures are required to be implemented by those providing healthcare services to limit or control access to confidential medical records. Thus, there is also a need for an integrated healthcare delivery system that can allow for private secure communication of healthcare data between the physician and the patient and throughout the system.

Although generally management of chronic diseases is enhanced by maintaining a proper medication regiment, little data is available to perform statistical analysis to determine to what extent deviations from a proper medication regiment effect management of such chronic diseases. Even with the advent of electronic medical records, data is often created and placed sporadically in different records situated at remote locations, making such data difficult to access for analysis.

In connection with special facilities such as, for example, nursing homes, assisted living facilities, and correctional facilities, however, data related to patients is maintained to provide the respective facilities with accurate administrative records. Such facilities that have implemented record keeping using electronic records also maintain electronic medical records or medical histories of the patients. The medical records typically have been developed and maintained either by the facilities or by a third party that has been providing healthcare services for the facility system. As described in co-pending U.S. Patent Application Ser. No. 10/806,878 by Clements et al., titled "Pharmaceutical Inventory and Dispensation Computer System and Methods," incorporated by reference, the electronic medical records can be used to accurately record such events as, for example, provider visit results, prescription histories, lab work results, and the like.

Medicinal administrators within such facilities are also required to maintain records associated with the physical administration and dispensation of prescribed medication to patients. With respect to correctional facilities, for example, inmates by law must have proper medical care while in the custody of the correctional facilities. Inmates historically have filed lawsuits against the correctional facilities claiming that they have been denied proper medical care. To provide sufficient evidence that the correctional facilities has exerted its best efforts to provide proper medical care, the correctional facilities can maintain records indicating the time, type, and dosage of medication that was administered to an inmate. A prison guard, present during medication administration, ensures that the inmate actually consumed the prescribed medication, unless, as in rare circumstances, the inmate was allowed to keep the medication on his or her person, which is referred to keep-on-person medication. The correctional facility can further keep records indicating whether or not the inmate has actually consumed the medication.

These medical records, and those associated with the other forms of special facilities, can be so specific that, with proper masking of the data with respect to the identification of the patient, researchers can have a readily available database of highly accurate medication administrations including medication route, dose, frequency, duration; and most importantly, compliance, for a plethora of medications that can allow for long-term studies on such medications generated literally at a "moments notice" and without the requisite time delay of forming a test group in order to formulate and execute such studies. Further, due to the use of electronic medical records, this concept could be applied to an entire integrated healthcare system whereby such data can be kept for other members of the populace serviced by such a system, if such system were in existence. Thus, clearly there is a need for an integrated healthcare system that accurately stores patient medication administration data in electronic medical records adequate to provide for statistical analysis of various medications dependent upon the various delivery attributes including medication administration compliance.

SUMMARY OF THE INVENTION

In view of the foregoing, embodiments of the present invention advantageously provide a system, methods, and program product that can deliver enhanced medical services delivery to geographically distributed patient populations by remotely separated physicians. Embodiments of the present invention provide an integrated healthcare delivery system capable of providing medical services delivery to a patient by a remotely separated physician of such quality and functionality to provide an enhanced substitute for an in-person face-to-face consultation. Embodiments of the present invention provide an integrated healthcare delivery system developed and enhanced by physicians and information technologists that overcomes the challenges of physician availability (or lack thereof), that integrates the concept of telemedicine with electronic medical technology including electronic medical records, medical protocols, electronic billing, and pharmacy services, and that is equally applicable to the Medicare/Medicaid and private healthcare patients, to thereby provide basic patient healthcare services to patients from a remote physician location or facility to a patient at a remote patient location, in both a resource efficient and a cost efficient manner.

For example, embodiments of the present invention include a system used to provide medical expertise, e.g., primary and specialized healthcare, from a remotely located physician to remote communities or communities of patients in isolation-including rural communities, cruise ships, prison populations, and to home-based and deployed military personnel including those deployed on ships, as well as those in barracks or field environments. Also for example, according to embodiments of the system, a pharmacy can receive a prescription order for the system, check for patient allergies, alert the physician to harmful drug interactions, check the drug formulary, and send the prescription to any pharmacy of the patient's choosing. Improved information access is also provided for management and administrative functions including operations and financial management. For example, billing and remittances can be sent and received electronically and are instantly available, making the system essentially paperless.

Embodiments of the present invention provide a system including a virtual physician's office, referred to as a remote physician medical service delivery suite, that can deliver both primary and specialty care from an environment that resembles a high tech office suite. The suite can provide instant access to a medical library and to a pharmacy system. An electronic medical record, which can contain the same information as a patient's chart, can be updated real-time with patient data including laboratory and radiological reports. X-rays are viewable on the screen at the touch of a button. After electronically examining the patient, the physician can use voice recognition technology to dictate his notes from the appointment. In addition to primary care (general practice and internal medicine), various types of medical specialties supported can include orthopedics, dermatology, cardiology, infectious diseases, and psychiatry, etc.

A corresponding patient medical service delivery station typically in the form of a delivery cart or integrated delivery table is positioned at a patient treatment location. The patient's station can incorporate a light table that enables the physician to view a recent x-ray or an ECG received from another source. The physician, for example, need only touch buttons on a control panel in his virtual office to place the light table's subject into the electronic medical record. The patient's station includes either one or two video monitors that allow the patient to see the physician and him/herself. An electronic multi-functional medical camera scope, used to see the patient's throat or ears, and an electronic stethoscope for transmitting heart sounds for diagnostic purposes, are also part of the patient's station. The physician may capture information from these devices and record it in the electronic medical record as a digital image. The patient's station can include lockable cabinets to prevent equipment theft or damage that would otherwise cause an interruption in a scheduled appointment. Further, each piece of the patient's station equipment is preferably modular to enhance ease of replacing a malfunctioning unit to minimize downtime, thus, helping to prevent any interruption in a scheduled appointment.

Embodiments of the present invention utilize broadband or satellite telecommunications network to support a live interactive video image between the patient and the physician. According to embodiments of the present invention, the network can be a completely dedicated network referred to as a private physician's network and having no outside connections, that can allow for private secure communication of healthcare data between the physician and the patient and throughout the system, ensuring that patient information cannot be accessed from a computer terminal not sitting on this network. The private physician's network further can provide security features such as, for example, custom encryption software components incorporating use of a rolling security key concept designed to ensure complete security of each communication within the private physician's network.

Embodiments of the present invention provide a system of enhanced medical services delivery to a patient located at a patient clinic by a remotely separated physician located at a remote physician site. For example, in an embodiment of the present invention a system includes one or more remote medical information management computers including memory to store data therein to thereby define a remote medical services server. A database associated with the remote medical services server includes a plurality of patient electronic medical records which provide a single consolidated medical service delivery record for a corresponding plurality of patients. Each record is accessible by a patient clinic medical service provider, a medical services scheduler, a utilization review or case management nurse, and the remote physician. The system also includes a remote medical services program product stored in the memory of the remote medical services server. The program product includes a set of instructions adapted to accept remote input from medical personnel to access the plurality of patient electronic medical records, to thereby allow display of and data entry in a selected patient electronic medical record.

A dedicated communications link, in communication with the remote medical services server, provides dedicated communications between a patient treatment location and the remote physician site located remote from the patient treatment location. The dedicated communications link is provided to establish a private network connection between the patient treatment location and the remote physician, site, defining a private physician's network. A plurality of patient medical service delivery stations is also provided. Each patient medical service delivery station is preferably positioned in a patient clinic located at the patient treatment location or customer site, and is in communication with the remote medical services server through the private physician's network. Each station has a video conferencing device including a video input and audio input device to capture detailed patient video images and patient audio, and a video display device positioned to be monitored by the patient clinic medical service provider and/or viewed by the patient to provide positive feedback, in the form of both video and audio, between a remote physician and the patient.

The system also includes at least one but preferably a plurality of remote physician medical service delivery suites positioned remote from the patient clinic at the remote physician site and in communication with the remote medical services server and each of the plurality of patient medical service delivery stations through the private physician's network. Each suite includes a video conferencing device including a video input and audio input device to capture video images and audio of the remote physician, and a video display device positioned to be monitored by the physician to provide patient audio and to display simultaneously patient areas of interest and patient electronic medical records, to thereby allow the remote physician to perform remote patient medical service delivery through the remote physician medical service delivery suite and a respective patient medical service delivery station.

The system also includes at least one medical services scheduler computer positioned remote from the patient treatment location, in communication with the remote medical services server. The medical services scheduler computer includes memory and software stored in the memory adapted to provide access to the remote medical services program product, to allow further screening of the remote physician medical services request, examination of remote physician schedule availability, and scheduling of a remote physician and a patient clinic medical service provider, to thereby initiate remote patient medical service delivery to a preselected patient through one of the plurality of patient medical service delivery stations at a preselected time.

The system also includes at least one utilization review or case management nurse computer positioned remote from the treatment location, in communication with the remote medical services server. The utilization review or case management nurse computer includes memory and software stored in the memory adapted to provide access to the remote medical services program product. For utilization review, the utilization review or case management nurse can display predetermined physician screening criteria to evaluate a physician services request, comparing the patient clinical data against the predetermined screening criteria. For case management, the utilization review or case management nurse can display the electronic medical record to review medical service delivery and to obtain follow-up patient disposition data.

Embodiments of the present invention include a method of providing enhanced medical services delivery by a remote physician to a patient being serviced in a facility having a medical service provider and a patient medical service delivery station. For example, in an embodiment of the present invention a method includes initiating a remote physician medical service delivery encounter by connecting a remote physician medical service delivery suite to the patient medical service delivery station through a network, the medical service provider assigned to the patient medical service delivery station and the remote physician assigned to a remote physician medical service delivery suite. The method also includes displaying on a remote physician medical service delivery suite videoscreen an electronic medical record of the patient, and providing to the remote physician audio data and visual data of the patient and the medical service provider through the remote physician medical service delivery suite and the patient medical service delivery station, simultaneously while displaying the electronic medical record.

Embodiments of the present invention include a method of providing enhanced medical services delivery by a remote specialist physician to a patient being serviced in a facility having a medical service provider and a patient medical service delivery station. For example, in an embodiment of the present invention a method includes evaluating a patient medical services request, comparing patient clinical information contained in the patient medical services request against predetermined screening criteria; generating an automated authorization, responsive to approval data recordation; accessing a patient electronic medical record and admitting the patient to add the patient to a remote physician medical service delivery schedule, to thereby initiate a remote patient medical service encounter with the scheduled remote specialist physician; and providing remote patient medical service delivery through the patient medical service delivery station and a remote physician medical service delivery suite remotely positioned with the scheduled remote specialist physician.

Embodiments of the present invention provide a method of generating revenue from and reducing physician costs in providing medical services to a special facility having a patient clinic. For example, in an embodiment of the present invention a method includes contracting for or otherwise establishing a plurality of physical or virtual telecommunication links, e.g., dedicated lines each serially connected or a virtual private network tunnel established over the Internet or other public broadband, between a remote physician facility and a special facility, e.g., assisted living facility, nursing facility, remote patient clinic, or correctional facility, to thereby establish a private network connection between the remote physician facility and the special facility, defining a physician's private network. Further, each remote physician facility can be connected to a plurality of separate substantially similar private networks. Referring to a correctional facility for illustrative purposes, the method also includes establishing patient electronic medical records in a structured database for each pre-identified prison inmate or patient/potential patient in the facility, the database partitioned such that only entities connected to the physician's private network can access the electronic medical records for the particular facility. The method also includes establishing a specific identifier, e.g., an IP address, and password for a patient medical service delivery station positioned in the facility; and establishing a communications interface with a remote medical services program product stored in memory of a remote medical services server associated with the remote physician facility, the interface adapted to accept remote input from correctional facility medical personnel to access the patient electronic medical records. The method further includes establishing a communications interface between a remote physician medical service delivery suite located at the remote physician facility and the patient medical service delivery station positioned in the facility, the interface adapted to provide a video and audio connection between the remote physician medical service delivery suite and the patient medical service delivery station.

Embodiments of the present invention provide a method of generating revenue from a patient medication compliance knowledgebase. For example, in an embodiment of the present invention a method includes providing a database stored in memory of a computer for maintaining a plurality of patient specific electronic medical records for individual patients including data indicating a patient medication prescription history for a plurality of prescribed medications having a predetermined set of delivery attributes and a corresponding patient prescription administration compliance history for the prescribed medications; and providing access to the database to perform a statistical analysis study on at least one of the plurality of prescribed medications, the study including analysis of medication compliance with at least one of the delivery attributes.

Embodiments of the present invention provide a computer readable medium that is readable by a computer to provide enhanced medical services delivery by a remote physician to a patient being serviced in a facility having a patient medical service delivery station. For example, a computer readable medium can include a set of instructions that when executed by a computer cause the computer to perform the operations of establishing a communications link in between a remote physician medical service delivery suite and the patient medical service delivery station through a communications network, providing data to display on a first remote physician medical service delivery suite video screen an electronic medical record of the patient, and providing data to display on a second remote physician medical service delivery suite video screen a real-time video image of the patient transmitted from the patient medical service delivery station, to thereby provide for simultaneously displaying to the remote physician both the electronic medical record and the real-time video image of the patient.

The system is more than a mere improvement over existing technology because it uses integrated electronic medical records, pharmacy formularies and medical protocols that reduce the need for discretion on the part of the patient care provider. The system includes use of sophisticated instrumentation, such as large plasma television screens, as compared to the PC monitors used in ordinary telemedicine operations. The system is also unique in that it utilizes a specially developed cart or table that allows a medical encounter to occur anywhere the cart or table can be provided, and inputs the details of this encounter into an electronic medical record that can be made available to the patient and subsequent providers anytime, anywhere. Both primary and specialty care consultations are available through the virtual physician office. The system has the capability to reach from a single location multiple patients forming patient populations separated by geography, facility, insurance plan, or other factors. The specialized medical peripherals, such as medical cameras and tele-stethoscopy devices (which allow heart sounds to be transmitted remotely with diagnostic quality) are part of the remote physician medical services component.

Further, the system can store patient medication administration data in electronic medical records adequate to provide for statistical analysis of various medications dependent upon the various delivery attributes including medication administration compliance and allows for statistical analysis to determine a patient cost index for enhancing remote medical service contract bidding and forecasting expected patient medical costs. Further, the electronic medical records allow for a patient cost sub-index to determine costs based on patient attributes. Through data analysis, the system is flexible enough to provide custom tailored customer facility staffing of medical service providers dependent upon such factors as, for example, the facility potential patient population, medical condition of the facility members (typically analyzed through use of the electronic medical records), customer budget, and temporal coverage.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIGS. 2A-B is a schematic block diagram providing details of selected portions of the system shown in FIG. 1A according to an embodiment of the present invention;

FIG. 2C is a schematic block diagram providing an alternative configuration of FIG. 2B according to an embodiment of the present invention;

FIG. 3A is a schematic view of a patient medical service delivery station according to an embodiment of the present invention;

DETAILED DESCRIPTION

Figure 1A:
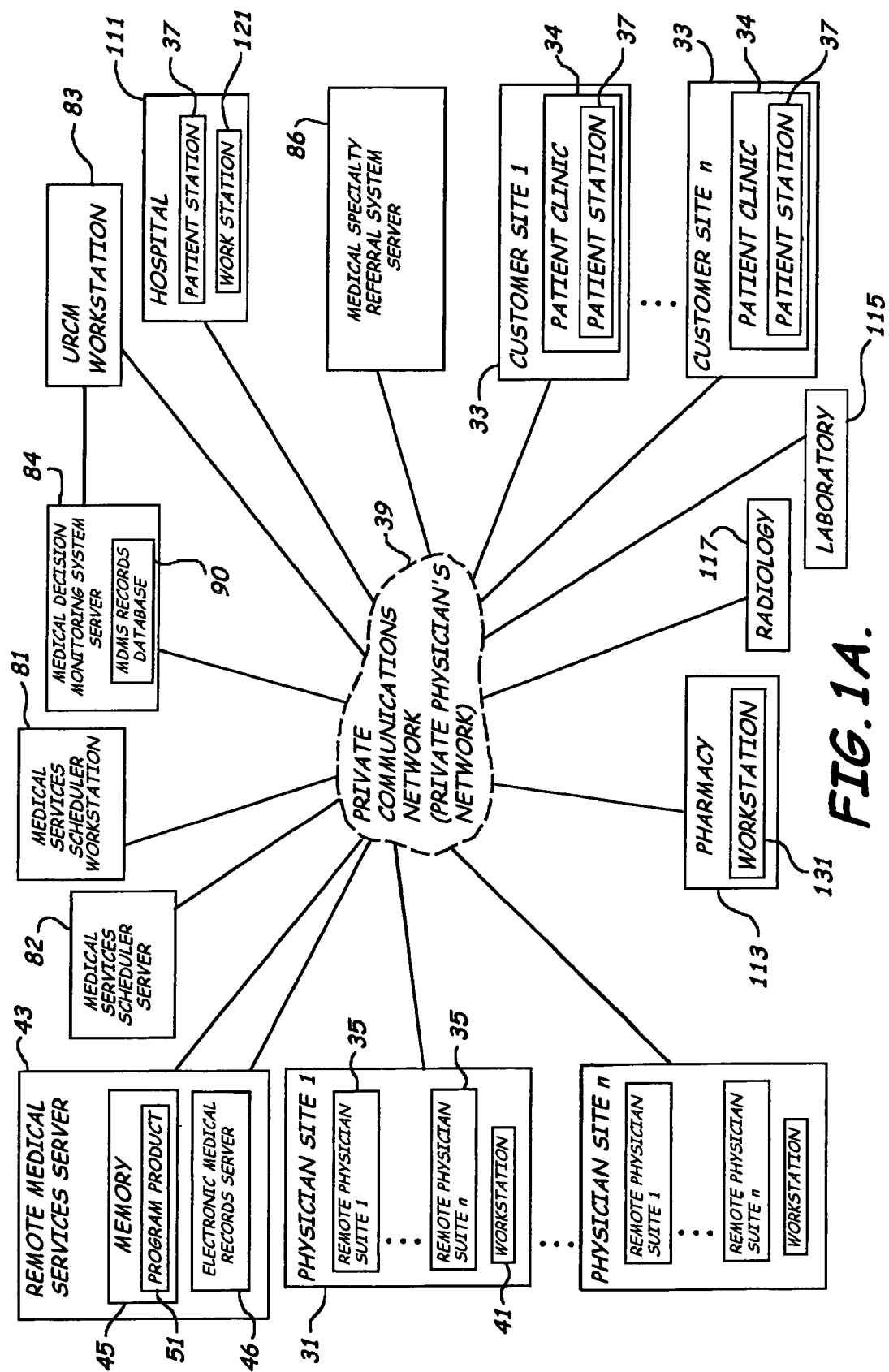
FIG. 1A is a schematic block diagram of system according to an embodiment of the present invention.

The present invention now will be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

As shown in FIGS. 1A-17, embodiments of the present invention provide a system 30 that includes the provision of remote physician medical services delivered from one or more physician sites 31 to a plurality of geographically distributed customer sites or facilities 33 using communication and information systems that allow an individual live face-to-face medical encounter with each patient. The system 30 includes provisions for the integration of all necessary records and information. A remote physician medical service delivery suite 35, in conjunction with an on-site patient medical service delivery station 37 connected through a network 39 provides the underpinning for delivery of physician care from an environment that resembles a high tech information technology command center. The system 30 has the capability to reach multiple customers from a single location. Specialized medical peripherals, such as, for example, medical cameras and tele-stethoscopy devices, which allow heart sounds to be transmitted remotely with diagnostic quality, are part of the patient medical service delivery station 37 component.

Advantageously, embodiments of the present invention provide an integrated healthcare system 30 that uses integrated electronic medical records, pharmacy formularies, telemedicine, and medical protocols developed and enhanced by physicians and information technologists to overcome the challenges of physician availability, and which can support the provision of both primary care (general practice and internal medicine) consultations and specialty (specific disciplines such as dermatology, cardiology etc.) consultations to various patient populations defined by geography, customer facility type, insurance plan, or other factors. For example, the system 30 can provide such medical services to remote communities or communities of patients in isolation such as, e.g., rural communities, cruise ships, and correctional facilities. The system 30 can also be used to provide healthcare to home-based and deployed military personnel. For example, it can be used in ships at sea, as well as in barracks and remote field environments. Also, advantageously, the system 30 provides for electronically managing patient scheduling, medical referrals, and providing utilization review prior to authorizing access to and scheduling of medical services.

More specifically, as shown in FIGS. 1A-2C, embodiments of the present invention provide a system 30 of enhanced medical services delivery to a patient located at a patient clinic 34 by one or more remotely separated physicians located at remote physician sites 31. For example, according to an embodiment of the present invention, a system 30 includes one or more remotely positioned medical information management computers, preferably located at one or more of the remote physician sites 31, and collectively forming a remote medical services server 43. The remote medical services server 43 includes memory 45 preferably in the form of RAM, ROM, and other forms of structured storage such as, for example, magnetic or optical memory. According to an embodiment of the present invention, a database 47 or plurality of preferably structured databases, preferably one for each customer unit, is associated with an electronic medical record database server 46 which along with the other computers and/or networking servers, known to those skilled in the art, form the remote medical services server 43. The database 47 includes a plurality of patient electronic medical records 49 preferably each providing a single consolidated medical service delivery record for a corresponding plurality of customer unit patients. Each electronic medical record 49 is preferably accessible by an on-site patient clinic medical service provider, a medical services scheduler, and a remote physician. Providing such access helps minimize artificial communication barriers, reduces the chance for miscommunication, and enhances patient care documentation.

To provide ready access to electronic medical records 49, the system 30 also includes a remote medical services program product 51 stored in the memory 45 of the remote medical services server 43. That is, the remote medical services program product 51 includes a set or sets of instructions to accept remote input from medical personnel to access the plurality of patient electronic medical records 49 to thereby allow display of and data entry in a selected patient electronic medical record 49. The remote medical services program product 51 includes a set or sets of instructions to electronically manage patient scheduling, medical referrals, and utilization review and case management data, to thereby enhance patient medical service delivery and documentation. Note, the remote medical services program product 51 can be in the form of microcode, programs, routines, and symbolic languages that provide a specific set for sets of ordered operations that control the functioning of the hardware and direct its operation, as known and understood by those skilled in the art. Note also, although described as being located generally and a single location, i.e., memory 45, the remote services program product 51 can have portions thereof distributed throughout the various computers forming the system 30, particularly with respect to banks or clusters of servers, or client-server communication modules.

The system 30 also includes a dedicated communications link, either physical or virtual, in communication with the remote medical services server 43 which provides dedicated communications between each customer site 33 and at least one remote physician site 31 located remote from each customer site 33, to thereby establish a private network connection between each customer site 33 and the remote physician site 31, defining a private physician's network 39. Depending upon various factors including climate, mobility, and accessibility associated with the customer site 33, preferably the dedicated communications link is preferably, for example, in the form of either a single or a plurality of T-1 lines, as understood by those skilled in the art, serially connected between each customer site 33 and the remote physician site 31 located remote from the customer sites 33 and between the remote physician site 31 and various other system components requiring a high bandwidth capability, described later. The dedicated communications link provides the necessary privacy to meet various statutory privacy requirements and bandwidth to support the transmission of large amounts of digital data back and forth between remote physician and patient.

The dedicated communications link can also be formed by other means known to those skilled in the art such as, for example, through other broadband communications such as, cable, satellite, Wi-Fi, or other wire-based and wireless communications. Satellite, for example, is particularly advantageous for extremely remote customer sites 33, such as those located in remote parts of the world and having no other readily available communication links, and is particularly advantageous for mobile remote customer sites 33, such as civilian cruise, merchant marine, or military ships. The privacy aspect of the communication link can be provided through use of encryption devices (not shown) on either end of the private physician's network 39. A virtual private network tunnel can be established over the Internet or other public or private broadband, as well as.

Figure 4:
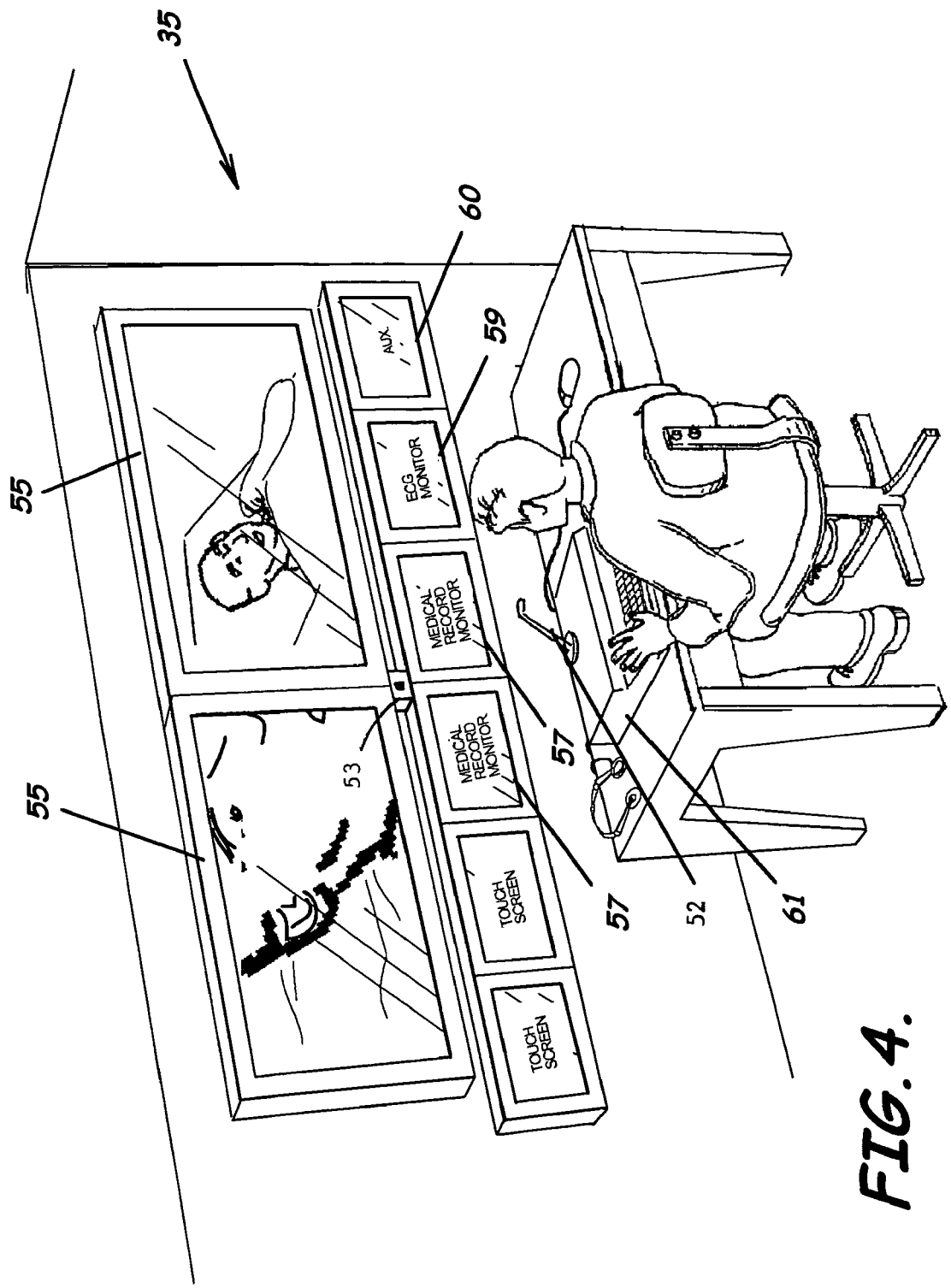
FIG. 4 is an environmental perspective view of a physician medical service delivery suite according to an embodiment of the present invention.

As perhaps best shown in FIG. 4, at the core of the invention's remote physician services are the remote physician medical delivery suites or studios 35, typically referred to as a virtual physician office. Each remote physician medical service delivery suite 35 is preferably positioned at the physician site 31, positioned remote from the customer site 33, and is in communication with the remote medical services server 43. Each remote physician medical delivery suite 35 preferably includes an audio input device 52 and a video input device 53 to capture audio and video images of the remote physician, and includes a video display device including a plurality of video displays 55, 55', 57, 59, 60, to display patient areas of interest and patient electronic medical records 49, to thereby allow the remote physician to perform remote patient medical service delivery through the remote physician medical service delivery suite 35. Each remote physician medical delivery suite 35 advantageously provides an integrated work environment supported by electronic medical records 49 and medical peripheral devices for delivering quality distributed medical care such as through videoconferencing or other techniques.

The remote physician medical delivery suites 35 allow a remotely positioned physician to "see" patients anywhere on the network 39. The remote physician medical service delivery suites 35 preferably incorporate a video display device including wall-size video screens 55 and/or desktop large-screen video monitors (not shown), electronic medical record video screens 57 for viewing records and entering new chart notes, electronic medical peripherals such as, for example, ECG readout monitor 59 for viewing an electrocardiograph, and auxiliary monitor 60 for viewing multi-functional videoscope imagery, e.g., otoscope imagery, headsets (not shown) for reviewing electronic stethoscope output. The remote physician medical service delivery suites 35 also preferably incorporate an automated encounter document creator to provide automated encounter document creation, e.g., voice recognition software and peripherals for providing real-time record transcriptions and preformatted templates selectable by the remote physician to reduce manual data entry requirements. A computer or physician command console 61 is adapted to control video display image selection, and provides the remote physician access to the patient electronic medical records 59, access to the dictation software, and use of the various peripherals. The remote physician medical delivery suites 35 support either primary care or specialist providers, and allow the virtual practice of medicine anywhere the network 39 can reach. Further, each remote physician medical delivery suite 35 is preferably equipped with an uninterruptible power and back-up/disaster recovery systems to insure availability at all times.

The system 30 can also include a remote workstation 41 associated with the remote physician site 31 in communication with the remote medical services server 43 and including memory and software stored in the memory adapted to provide access to the remote medical services program product 51, to allow a user, e.g., remote physician, physician assistant, scheduler, or utilization review or case management (URCM) nurse, to display the patient electronic medical record 49 to review patient medical administration data and to enter additional patient medical administration data.

Figure 3B:
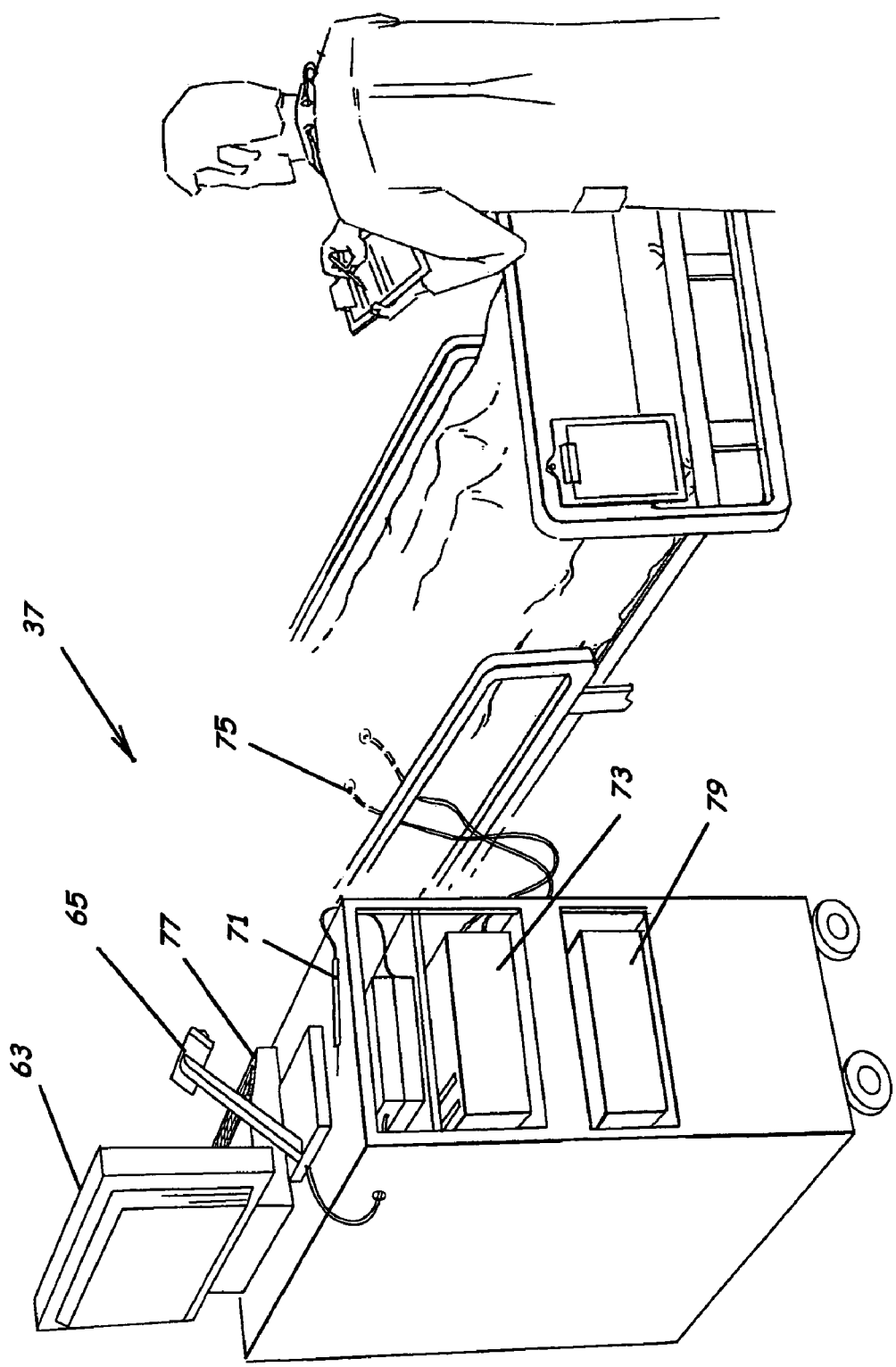
FIG. 3B is an environmental perspective view of a patient medical service delivery station according to an embodiment of the present invention.
Figure 3C:
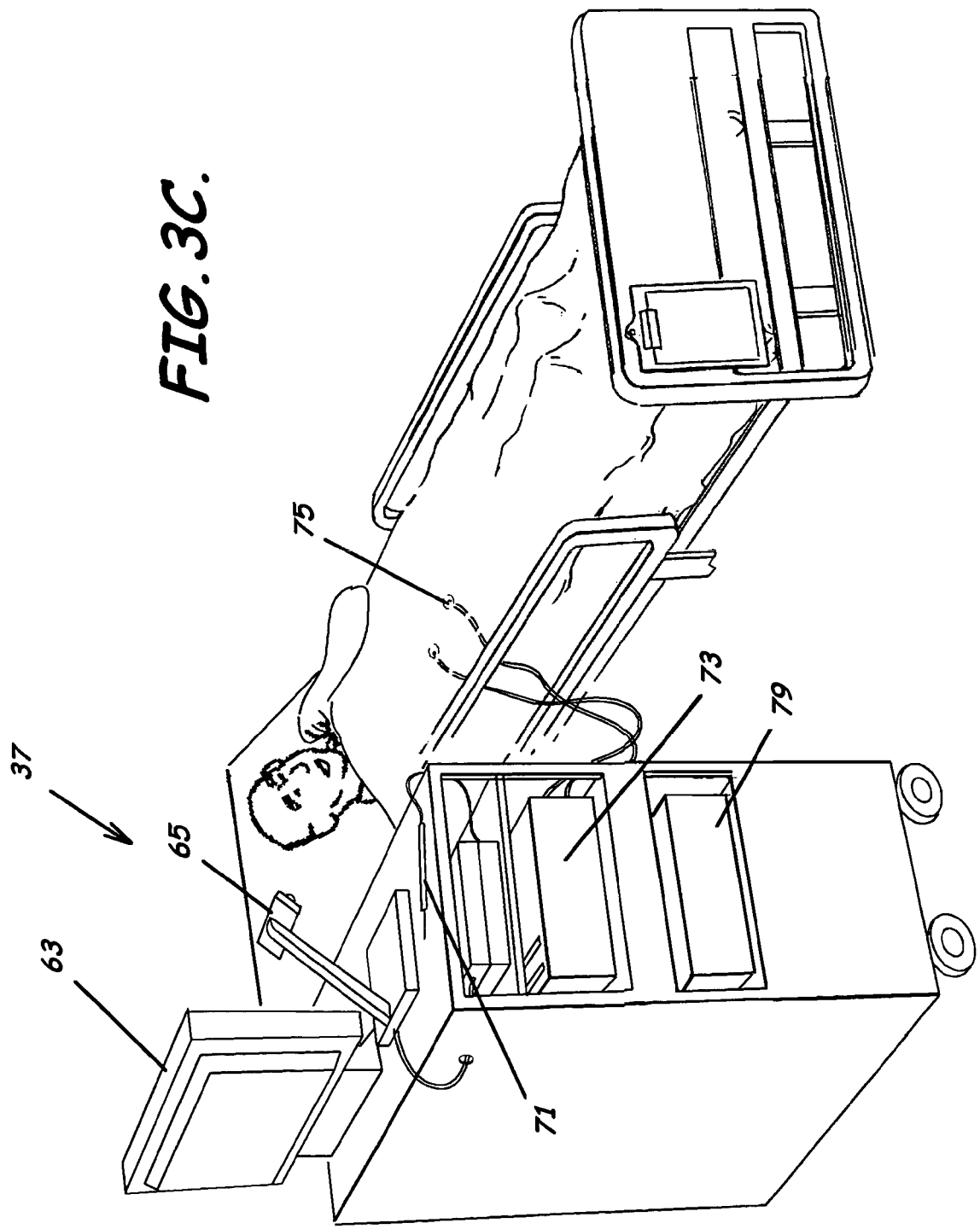
FIG. 3C is an environmental perspective view of a patient self-administering medication before a patient medical service delivery station according to an embodiment of the present invention.

As perhaps best shown in FIGS. 3A-B, each customer site 33 includes at least one but preferably a plurality of patient medical service delivery stations or carts 37 each preferably positioned in a patient clinic 34 located at the customer site 33 to provide the remote physician the ability to communicate with and treat a patient. Advantageously, each patient medical service delivery station 37 is designed to be easily moved about the patient clinic 34, and has wheels and handles to allow easy manipulation. The patient medical service delivery station 37 includes various medical videoconferencing components including at least one video monitor 63 and a remotely controllable pan/zoom video input device 65 preferably having over 180 degrees range of motion and providing diagnostic quality images. Note, each patient medical service delivery station 37 is adapted to be manned by either a patient clinic physician who requires consultation with a remote physician specialist while providing medical service delivery; or either a patient clinic physician assistant or patient clinic nurse, often referred to as an "extender," to provide the in-person portion of the medical service delivery by either a remote specialist physician or a remote primary care physician and to manipulate the various examination instruments, described below.

Each patient medical service delivery station 37 also includes various electronic medical instruments adapted to communicate with the remote physician medical service delivery suites 35, through the private physician's network 35. For example, each patient medical service delivery station 37 preferably includes a video visualizer or light table 67 adapted to provide to the remote physician during the remote patient medical service delivery video visualizations of documents such as, for example, a hard-copy x-ray or an ECG print out formulated outside system 30. Also preferably included is an electronic stethoscope and sending unit 69 adapted to provide for an electronic auscultation of the patient, and a multi-functional videoscope 71, e.g., a handheld medical camera complete with fiber-optic halogen lighting used to peer into the patient's throat or ears, or examine the skin closely. An ECG 73 connected to ECG leads 75 can provide electrocardiograph visualization during remote patient medical service delivery. A point-of-care laboratory testing device/kit 79, either stand-alone or networked, can provide for real-time laboratory results just prior to or during provision of the remote medical service delivery. The medical service delivery station 37 is scalable to allow the inclusion of other devices known to those skilled in the art such as, for example, an ultrasound device (not shown) to perform ultrasonography.

Each patient medical service delivery station 37 also can include a computer or workstation 77 in communication with the remote medical services server 43 through the private physician's network 39, allowing the patient clinic medical service provider at the customer site 33 complete access to patient medical information, and necessary resources to connect to the remote physician medical delivery suites 35. Specifically, each computer 77 includes memory and software stored in the memory adapted to provide access to the remote medical services program product 51 to allow display of the patient electronic medical record 49 so that the patient clinic medical service provider can review current patient medical administration data and can enter additional patient medical administration data.

As stated above, the combination of the remote physician medical service delivery suites 35 and patient medical service delivery stations 37 allows for remote medical service delivery from various specialist physicians. This is an important feature as specialist physician services, especially in unique specialties, are often difficult to procure. Specialist physician consultations can be for various medical specialty disciplines including cardiology, orthopedics, psychology, mental health management, infectious disease/HIV management, dermatology, and urology. These consultations are typically for services outside of the normal scope of the patient clinic primary care physician's expertise. Access to remote specialty services provides the customer the opportunity to provide the most appropriate care in an expedient manner. Advantageously, this allows the total cost of care to be lower through reduced patient transportation and quicker access to appropriate care. During a remote medical service delivery encounter, the remote specialist physician can receive all required data and can recreate all consultation notes electronically. In this manner, specialist consultation reports are available back to the patient clinic 34 literally at the conclusion of the virtual visit.

The combination of the remote physician medical service delivery suites 35 and patient medical service delivery stations 37 not only allows for remote medical service delivery from a specialist physician, but also an additional primary care physician. The remote primary care physician consultations provide direct interaction between the remote primary care physician and a patient. These visits can support all primary care needs, such as, for example, physicals, minor medical problems, and management of chronic conditions. Remote medical services provided can also include medical diagnosis, medication prescribing, laboratory ordering, and follow-up care. These live, virtual face-to-face consultations can be performed substantially exactly like actual in-person physician visits. At the customer site 33, physician extenders such as, for example, nurses or physician assistants, interact with the patient and provide the hands-on portion of the examinations. The patient medical service delivery station peripherals, described above, can provide the examining physician with all needed supplemental information. In this manner the physician is provided with information required to perform a complete diagnosis and management decisions. According to this configuration, access to on-call emergency medicine services staffed by certified ER physicians is advantageously available 24/7.

Further, although according to the preferred embodiment of the present invention, the system 30 provides an in-person primary care physician at each patient clinic 34, primary care physician staffing problems can arise. Thus, the remote primary care physician medical service delivery can be remotely provided by either a primary care physician scheduled from a pool of physicians at the physician site 31, a substitute physician, or a primary care physician normally providing in-patient's service at a patient clinic 34. This feature advantageously enhances physician-patient appointment attendance and reduces physician employment costs, particularly those associated with locum tenens doctors, because it provides a ready substitute physician for an absent patient clinic primary care physician, allows the provision of additional staffing of a patient clinic 34 inflected with an unusually heavy workload, and it allows an in-patient primary care physician temporarily afflicted with a medical condition that would otherwise prevent the provision of in-person patient medical services at the patient clinic 34 to continue providing medical service delivery, negating a need to provide an on-site patient clinic physician replacement.

As perhaps best shown in FIGS. 1A-2C, the system 30 also includes at least one medical services scheduler computer or workstation 81 or server 82 positioned remote from the customer site 33 and in communication with the remote medical services server 43 and including memory and software stored in the memory adapted to provide access to the remote medical services program product 51. The medical services scheduler computer 81 can allow a scheduler access to patient electronic medical records 49 to establish a remote medical service delivery appointment. That is, the scheduler can examine remote physician schedule availability for the remote physicians and availability of the remote physician medical service delivery suites 35 at the physician site 31, and perform scheduling of a remote physician and a patient clinic medical service provider, to thereby initiate remote patient medical service delivery to a patient through a patient medical service delivery station 37 at the customer site 33 at a preselected time.

Figure 2A:
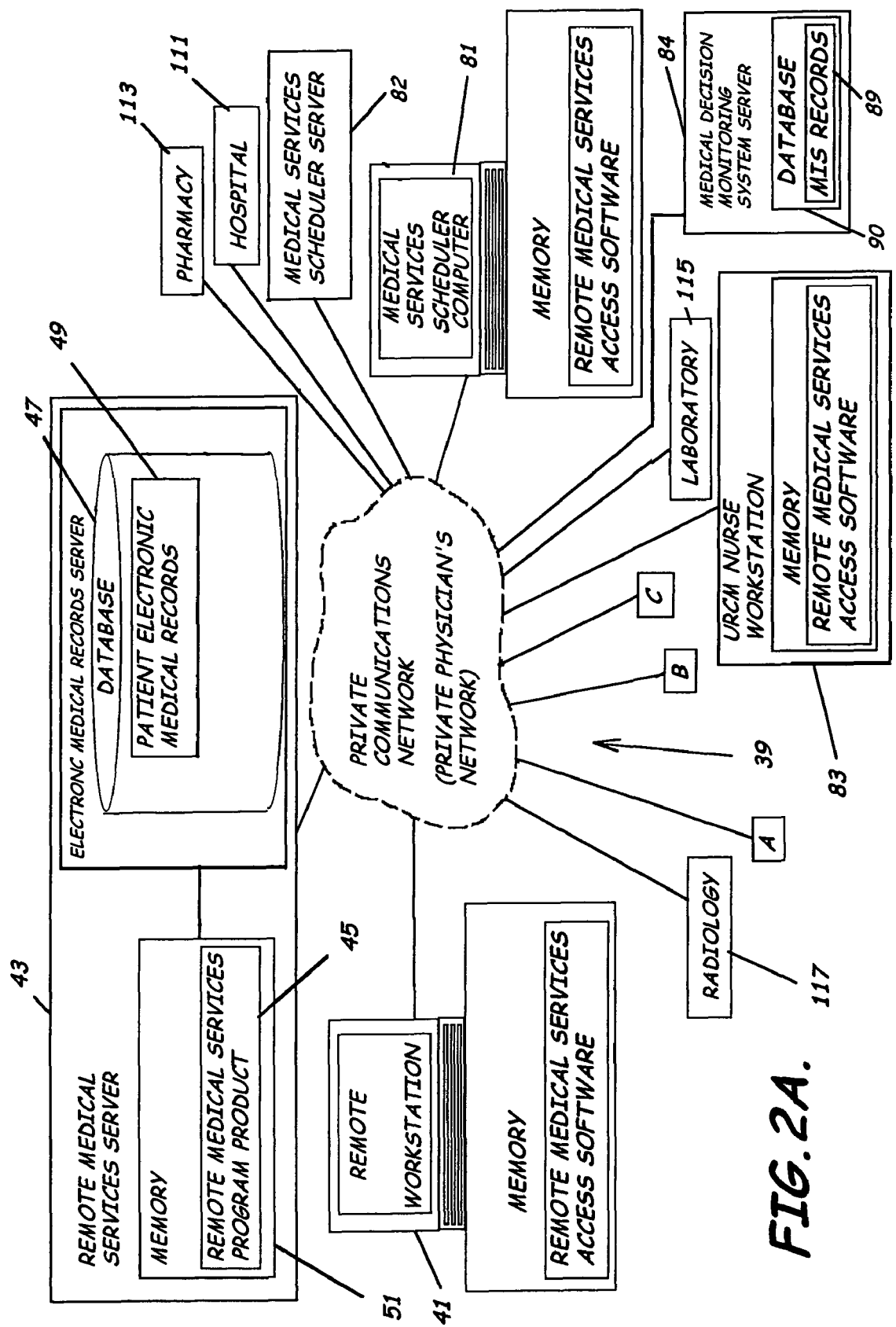

According to the preferred embodiment of the present invention, a patient clinic medical services provider accesses a medical specialty record referral system (MSRS) record 85 (FIG. 2B), or other suitable service request media, to update the request with the appointment data. The MSRS record 85 is preferably stored on a MSRS server 86 (FIG. 2A), located either within or external to a respective customer facility or site 33, that is in communication with a computer or workstation 91 accessible to the requesting physician and preferably located within the respective customer facility or site 33. The MSRS record 85 can, however, alternatively be associated with the remote medical services server 43, and/or alternatively be part of the patient electronic medical record 49. The patient clinic medical services provider can access the MSRS records 85 to determine if the remote medical service delivery request has been approved. As shown in FIG. 2A-B, the workstation 91 is preferably in communication with the remote medical services server 43 and the MSRS server 86 through the private physician's network 39. The workstation 91 preferably includes memory 93 and software stored in the memory 93 adapted to provide access to the remote medical services program product 51 to allow remote computerized physician medical service to request entry so that the patient clinic medical service provider can input a physician's medical service request, and display the patient electronic medical record 49 to review current patient medical administration data and/or enter additional patient medical administration data.

The system 30 can also include at least one but preferably a plurality of URCM nurse computers or workstations 83 positioned either remote from the customer facility or site 33, within the customer facility or site 33, or a combination thereof. The URCM nurse computers or workstations 83 are in communication with the remote medical services server 43 and can include memory and software stored in the memory adapted to provide access to the remote medical services program product 51 to allow a URCM nurse access to patient electronic medical records 49 preferably stored in database 47 to review resource utilization and/or monitor patient medical service delivery.

More particularly, a URCM nurse specializing in utilization review provides gate-keeping functions by examining patient electronic medical records 49 and evaluating requested remote medical service delivery appointments entered in the MSRS to approve the appointment requests and/or propose and discuss alternatives with the requesting medical service provider. The URCM nurse can examine remote physician schedule availability for the remote physicians and availability of the remote physician medical service delivery suites 35 at the physician site 31. The URCM nurse can further access medical decision monitoring system (MDMS) records 89, preferably stored in a MDMS database 90 associated with an MDMS server 84 (FIG. 1A), to document particular medical services requests and associated clinical data along with the evaluation results; and can access the respective MSRS records 85 to update the records in accord with the results of the evaluations and/or proposed modifications to the medical services requests. A URCM nurse specializing in case management can further utilize the URCM computer or workstation 83 to access the patient electronic medical records 49 to monitor, over time, the delivery of both remote and local medical services. Note, although the MDMS records 89 are preferably associated with an MDMS server 84, typically separate from the patient electronic medical records 49, the MDMS records 89 can alternatively be associated with a customer or customer affiliated computer or be part of or stored with the patient electronic medical record 49.

According to the preferred embodiment of the present invention, a scheduler schedules the appointment for the requested remote medical services in the respective patient's electronic medical record 49 using the remote medical services program product 51. The scheduler further can access the MSRS records 85 to update the request with the appointment data. The patient clinic medical services provider can access the MSRS records 85 to determine if the remote medical service delivery request has been approved. Alternatively, the scheduler can provide direct contact to both the scheduled remote physician and the scheduled patient clinic medical service provider to provide scheduling information.

As shown in FIG. 2C, the system 30 can also include a customer medical information management computer including memory 99 to store data therein to thereby define a customer medical services server 101, which can be positioned at one or more of the customer sites or facilities 33. Due to the remote nature between the physician site 31 and some customer sites or facilities 33 and depending upon the type of configuration utilized to establish the physician's private network 39, continuous uninterrupted transmission is not always established continuously 24 hours per day. Thus, advantageously, a duplicate copy of the patient electronic medical records 49 associated with the individual customer facility or site 33 can be stored in the memory 99 of the customer medical services server 101 to provide a ready access to the individual customer's patient electronic medical records 49 in the event of a temporary network interruption or failure. Thus, advantageously, the remote medical services program product 51 is preferably adapted to perform the operation of maintaining a duplicate copy of an associated customer's patient electronic medical records 49, one copy stored in the memory 45 of the remote medical services server 43 and the other copy stored in the memory 99 of or database associated to a respective customer medical services server 101.

Although other methodologies are within the scope of the present invention, in an embodiment of the present invention, when a change is made to a respective patient's electronic medical record 49 for the particular customer and when the network 39 is functioning properly, the remote medical services program product 51 simultaneously updates both copies of electronic medical records 49. When a change is made to a respective patient's medical record 49 for a particular customer, either from input to the electronic medical record 49 at the customer site 33, through input at the physician site 31, or through input at an alternative system site, described later, the remote medical services program product 51 detects a network interruption or failure and, responsive to the detected failure, applies the change to the respective customer site copy or physician site copy and maintains a log of electronic medical record changes.

Upon reestablishment of the network connection after a network failure, the portion of the remote medical services program product 51 located in the memory 99 of the customer medical services server 101 and the portion of the remote medical services program product 51 located on the remote medical services server 43 can detect changes in individual patient electronic medical records 49 and cross-update the respective changed records 49 on the customer medical services server 101 and remote medical services server 43, respectively. Note, alternatives are available such as, for example, performing a periodic download or update of records stored in the memory 99 of the customer medical services server 101 or other methodology known to those skilled in the art. Note, this alternative methodology is also useful for networks having a less than ideal bandwidth capability to thereby provide a reduced record access delay. That is, after both copies of the electronic medical records 49 are established, only the changes need be transmitted over the network 39, thus providing improved access performance.

Figure 1B:
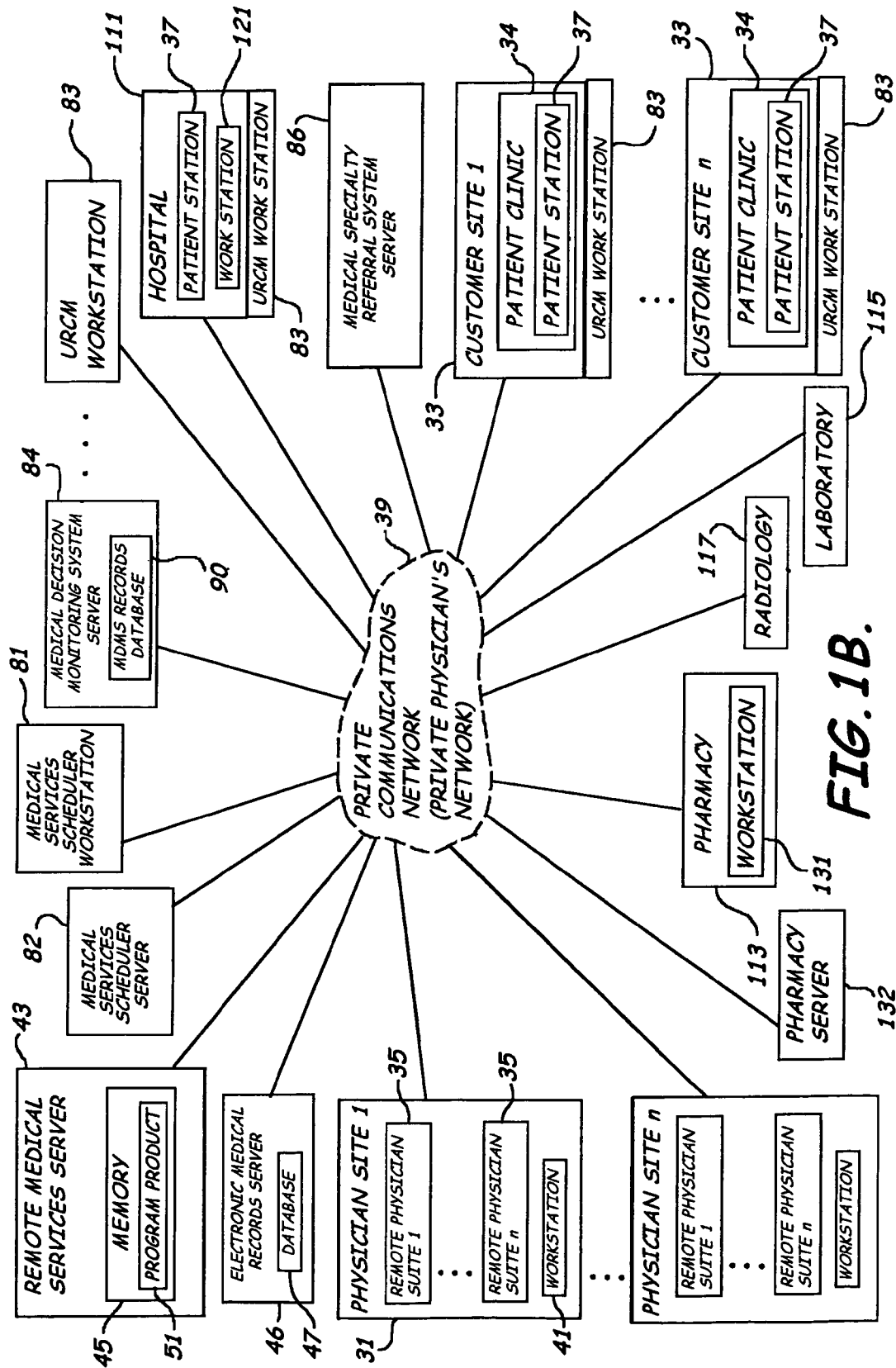
FIG. 1B is a schematic block diagram of system according to an embodiment of the present invention.

As shown in FIGS. 1A-1B, according to the preferred embodiment of the present invention, the system 30 preferably also includes one or more hospitals 111, and a pharmacy or pharmacy unit 113, a laboratory or laboratory unit 115, and a radiology unit 117, functioning either as separate entities or positioned within a hospital 111. The hospital or hospitals 111, generally located remote from the customer site 33, provide additional in-person physician medical services delivery not receptive to remote physician medical services delivery at the patient clinic 34. The hospital 111 can include one or more hospital physician workstations 121 located in the hospital and in communication with the remote medical services server 43 through the private physician's network 39. Each workstation 121 includes memory and software stored in the memory adapted to provide access to the remote medical services program product 51, to allow a hospital physician or other authorized hospital medical service provider to display the patient electronic medical record 49 for the preselected patient to thereby provide hospital physician medical services. This is especially advantageous where the hospital 111 is a community hospital not otherwise maintaining patient medical records either electronically or in a compatible electronic form, and thus, would not otherwise have real-time access to the patient's electronic medical records 49. The workstation 121 also allows a medical service provider such as, for example, a URCM nurse, to transcribe hospital medical record events into the patient's electronic medical record 49.

In the preferred embodiment of the present invention, the private physician's network 39 further includes a dedicated communications link in communication with the remote medical services server 43 providing dedicated communications between the hospital 111 and the remote physician site 31, thereby establishing a private network connection between the hospital 111 and the remote physician site 31. In this embodiment, the hospital 111 preferably includes at least one patient medical service delivery station 37 positioned in the hospital 111 and in communication with the remote medical services server 43 through the private physician's network 39. Advantageously, the patient medical service delivery station 37 provides the hospital 111 supplementary primary care physician staffing and allows for consultation of hospital personnel with a remote specialist physician.

The system 30 can include various pharmacy/drug related services, ranging from straightforward online medical service provider order entry and drug compliance to complete pharmaceutical procurement and delivery, including formulary management, pharmacist review, and point-of-use packaging. The pharmacy 113 is generally located remote from the customer facility or site 33 to provide pharmacy services. A pharmacy workstation 131 located in the pharmacy 113, in communication with the remote medical services server 43, includes memory and software stored in the memory adapted to provide access to the remote medical services program product 51, to allow a pharmacist, pharmacy assistant, nurse, or, in the correctional facility example, an authorized prison guard to display a patient electronic medical record 49 for a patient, to thereby provide pharmacy services to the patient. According to the preferred embodiment of the present invention, pharmacy records are associated with or included in the electronic medical records 49. In another embodiment of the present invention, pharmacy records are stored in a separate pharmacy records server 132 (see FIG. 1B).

The system 30 provides the ability to benchmark prescription costs and dosages, and provides for comparison of a physician's prescription and dosage choices against the general prescription population or with other pharmaceutical options. Advantageously, prescribing patterns can be seen virtually in real time, and costs can be more effectively analyzed and managed than in a traditional pharmacy system. Further, the system 30 provides for medication use tracking, provides for clinical checks including those for patient allergies, alerts the physician to harmful drug interactions, checks the drug formulary, and can send the prescription to a selected local pharmacy for filling. After delivery, medication use can then be directly documented.

A pharmacy prescription compliance computer or workstation 133 can be positioned remote from the pharmacy 113 at the customer facility or site 33, in communication with the remote medical services server 43 through the private physician's network 39. The computer 133 includes memory and software stored in the memory adapted to provide access to the remote medical services program product 51 to thereby record a patient medication administration compliance for a respective patient medication order. Either a medical service provider at the customer facility or site 33 or a customer representative, e.g., a pharmacy assistant, nurse, or prison guard for a correctional facility customer, can visibly monitor the medication administration. Alternatively, the patient can be positioned within the view of patient medical service delivery station 37 which can provide monitoring of patient medication administration compliance either through visual observation by a remote medical services provider or through use of automated recording.

The laboratory unit 115, providing laboratory medical service delivery, is located remote from the customer facility or site 33 and remote from the remote physician site 31 to provide laboratory services. The laboratory unit 115 can be either associated with the hospital 111 or a separate independent unit. If associated with the hospital 111, the laboratory can access the physician's private network 39 through the hospital 111. For an independent laboratory unit 115, the private physician's network can include a limited access communications link in communication with the remote medical services server 43 which can provide communications between the laboratory 115 and the remote medical services server 43 to thereby update the electronic medical records 49 with laboratory data.

The radiology unit 117 provides radiology medical service delivery. The radiology unit is preferably associated with the hospital 111 and thus has access to the physician's private network 39 to post radiology charts to the database 47. As with the laboratory unit 115, if the radiology unit 117 is not accorded full authorization to access the database 47, limited access can be provided. Note, for both the laboratory unit 115 and the radiology unit 117, the communications link need not be dedicated and, depending upon whether patient identifying data is utilized, the communication link may not need to be provided encryption devices, as described previously.

Figure 5A:
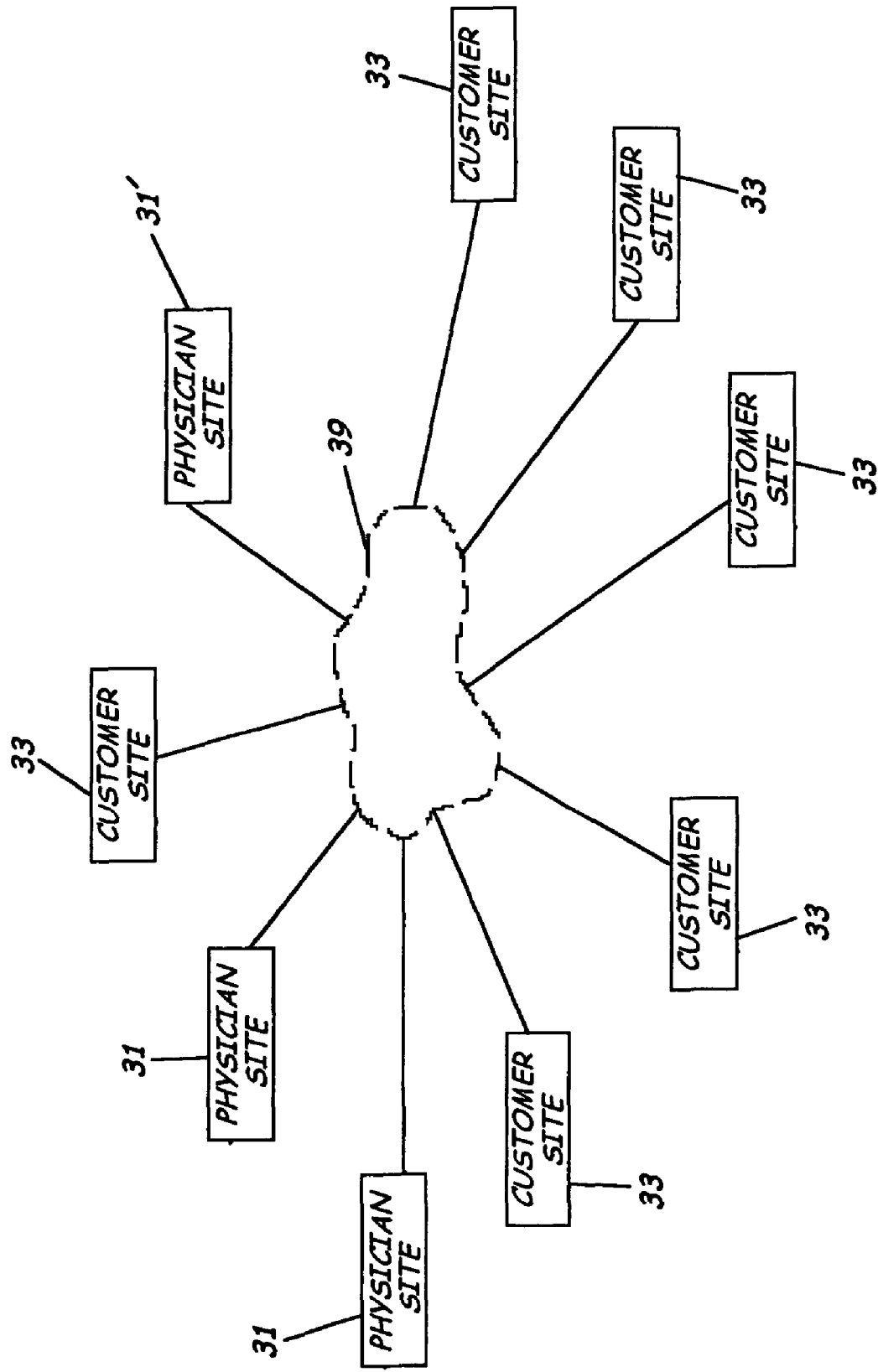
FIG. 5A is a schematic view of a system according to an embodiment of the present invention.
Figure 5B:
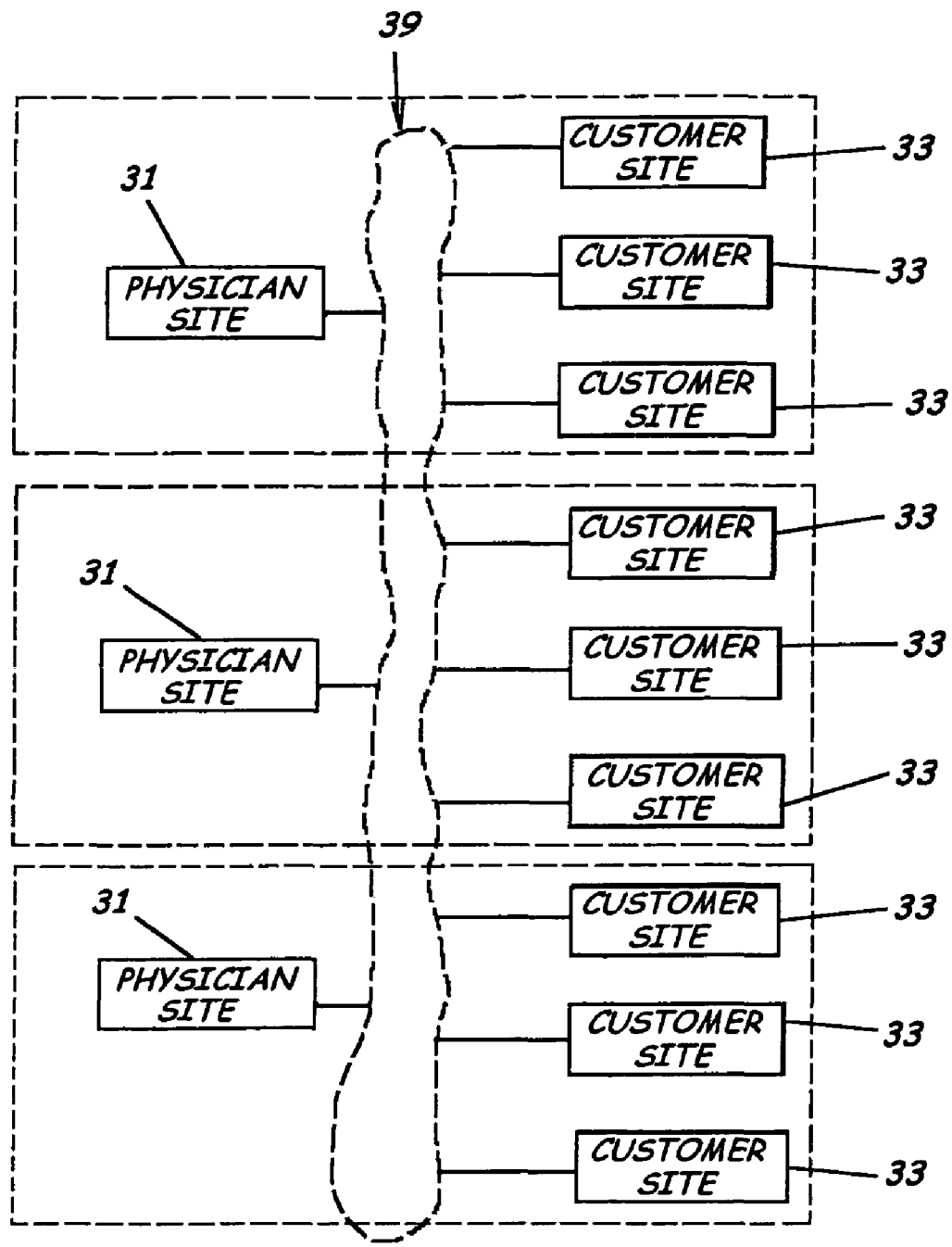
FIG. 5B is a schematic view of a system according to an embodiment of the present invention.
Figure 5C:
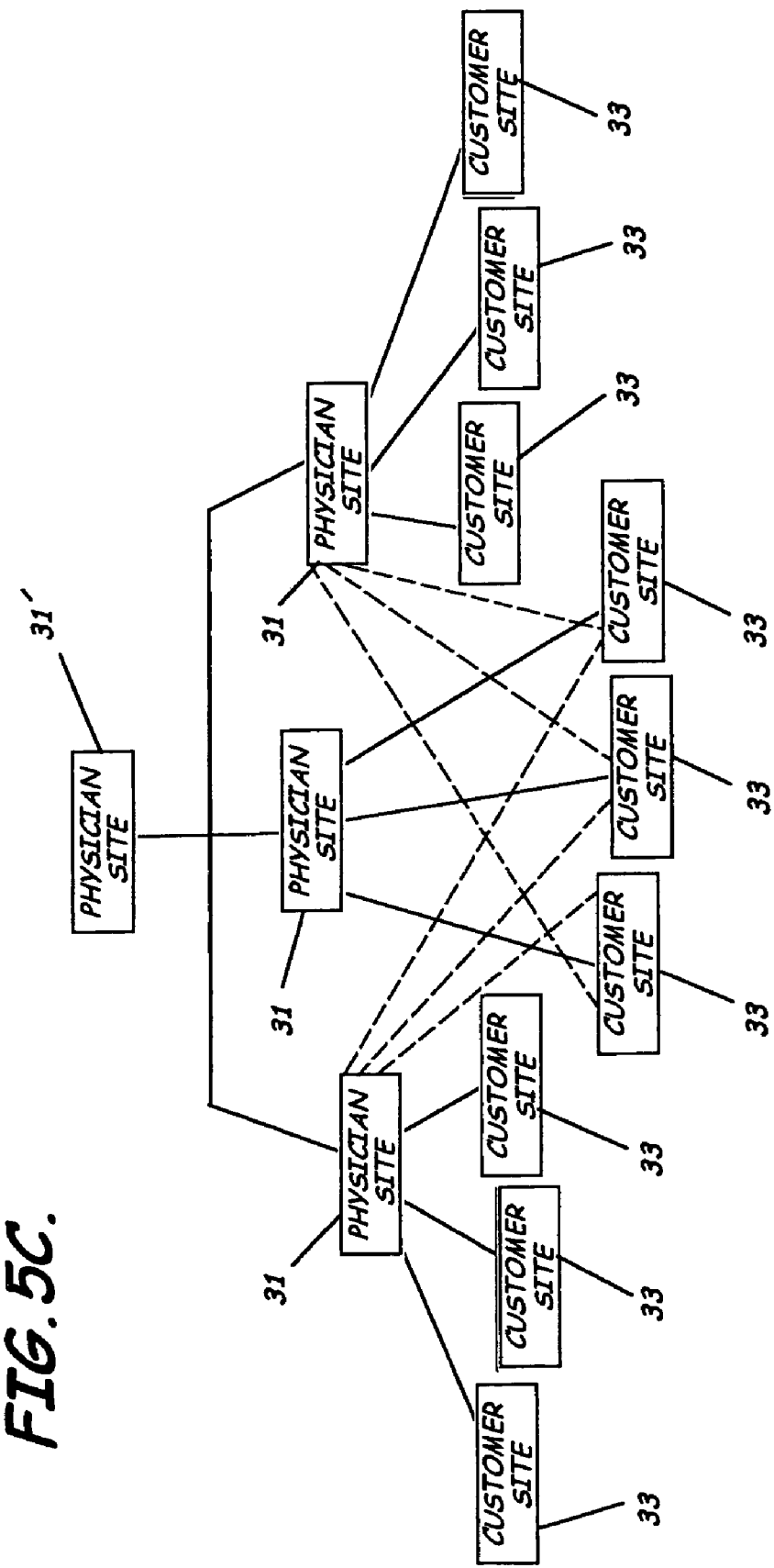
FIG. 5C is a schematic view of a system according to an embodiment of the present invention.

As shown in FIGS. 5A-5C, embodiments of the present invention support establishing a system 30 having an interconnected network of physician and customer sites 31, 33, and multiple systems 30, which can be associated with regional areas. This configuration allows for the application of autonomous systems 30 which provide remote physician medical service delivery in accordance with various state laws or other regulatory requirements. Each remote physician site 31 supporting the various regional areas can further be linked to a central physician site 31' which can allow for centralized management and which can allow for the support of even more unique specialties. For example, during application of remote medical service delivery, a remote specialist physician located at one of the regional physician sites 31 and using a remote physician medical service delivery suite 35 may conference with a remote specialist physician at the central physician site 31' also networked to a patient via a remote physician medical service delivery suite 35. Advantageously, this allows the remote physician at the central physician site 31' to also view the patient and apply his or her knowledgebase to the remote physician at the regional physician site 31 and thus, comply with the regional regulatory requirements regarding the practice of medicine.

As shown in FIGS. 1A-17, according to embodiments of the present invention, the system 30 includes various methods of establishing or initiating the provision of remote physician medical services. These methods can include, for example: the steps that occur while a patient is being treated, e.g. steps involving the interaction between the remote physician and a patient and/or the interaction between the remote physician and other medical services specialist when diagnostic tests are performed; the steps associated with treatment authorization and treatment review; the steps associated with enrolling new patients; and those associated with report generation and administration of the system, itself. Note, the various steps described below may occur in the order shown in the figures, may occur in parallel, may be interchanged, or may be bypassed altogether.

In an embodiment of the present invention, provided is a method of providing enhanced medical services delivery by a remote specialist physician to a patient being serviced in a customer facility or site 33 having a medical service provider and a patient medical service delivery station 37. Medical services from a specialist are preferably provided initially using the remote specialist physician medical service delivery functionality of the system 30, rather than by either transporting the patient to the specialist physician or the specialist physician to the patient. The remote specialist physician can then determine if additional or more extensive treatment is necessary. Advantageously, this functionality reduces specialist physician medical delivery costs, increases specialist physician availability, and/or reduces patient transportation requirements, especially where the patient has limited transportation, such as a prison inmate or an invalid, or where the patient is located a significant distance from a specialist physician. The following process will be described using a generic facility as an example customer facility. Most of the process steps, described below, are directly transferable to other customer facilities or sites 33. Advantageously, the system 30 is flexible enough to allow various other customer-driven requirements to be implemented, as will be understood by those skilled in the art.

Figure 6A:
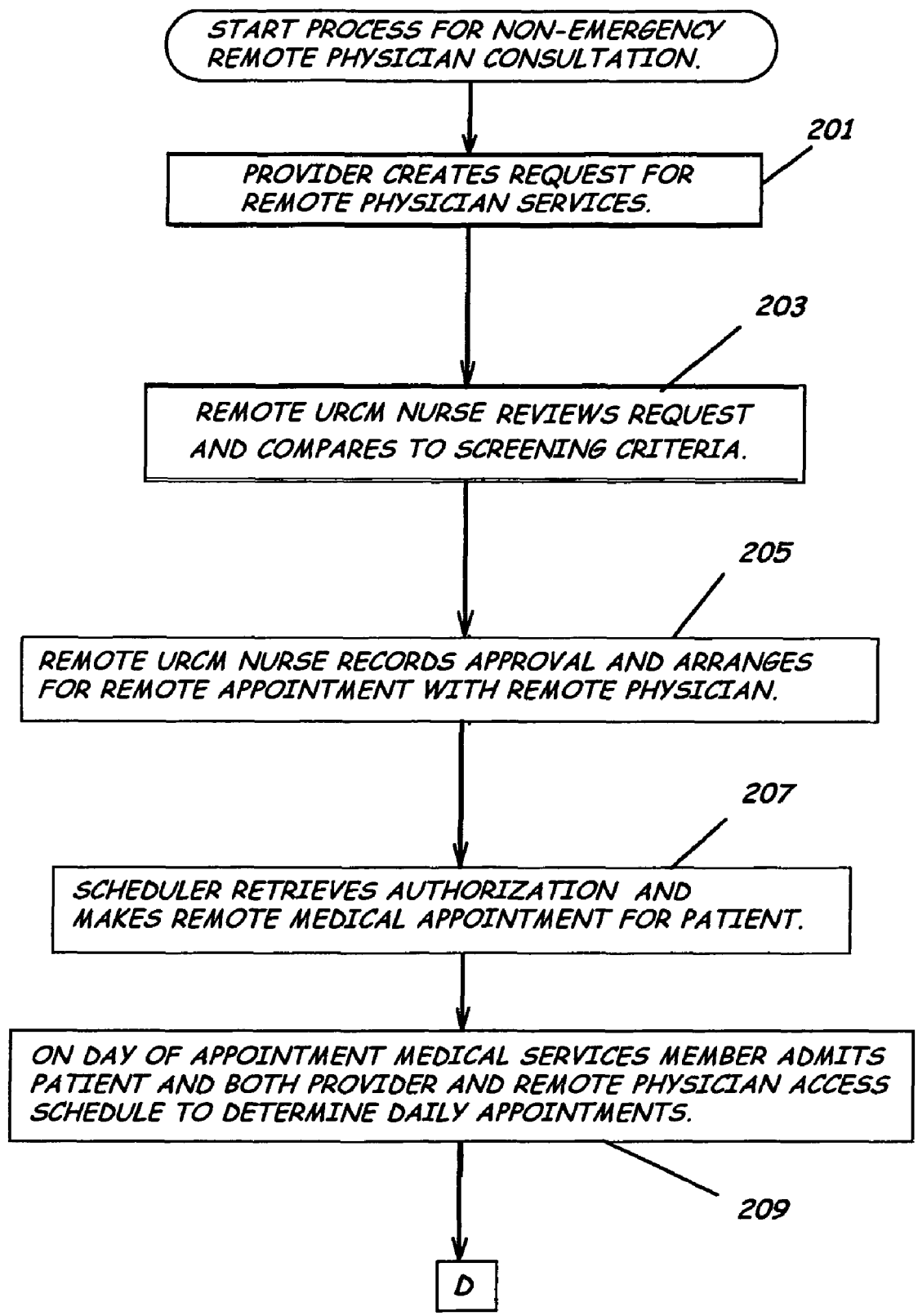
FIG. 6A-B is a schematic flow diagram of a method of providing enhanced medical service delivery according to an embodiment of the present invention.
Figure 6B:
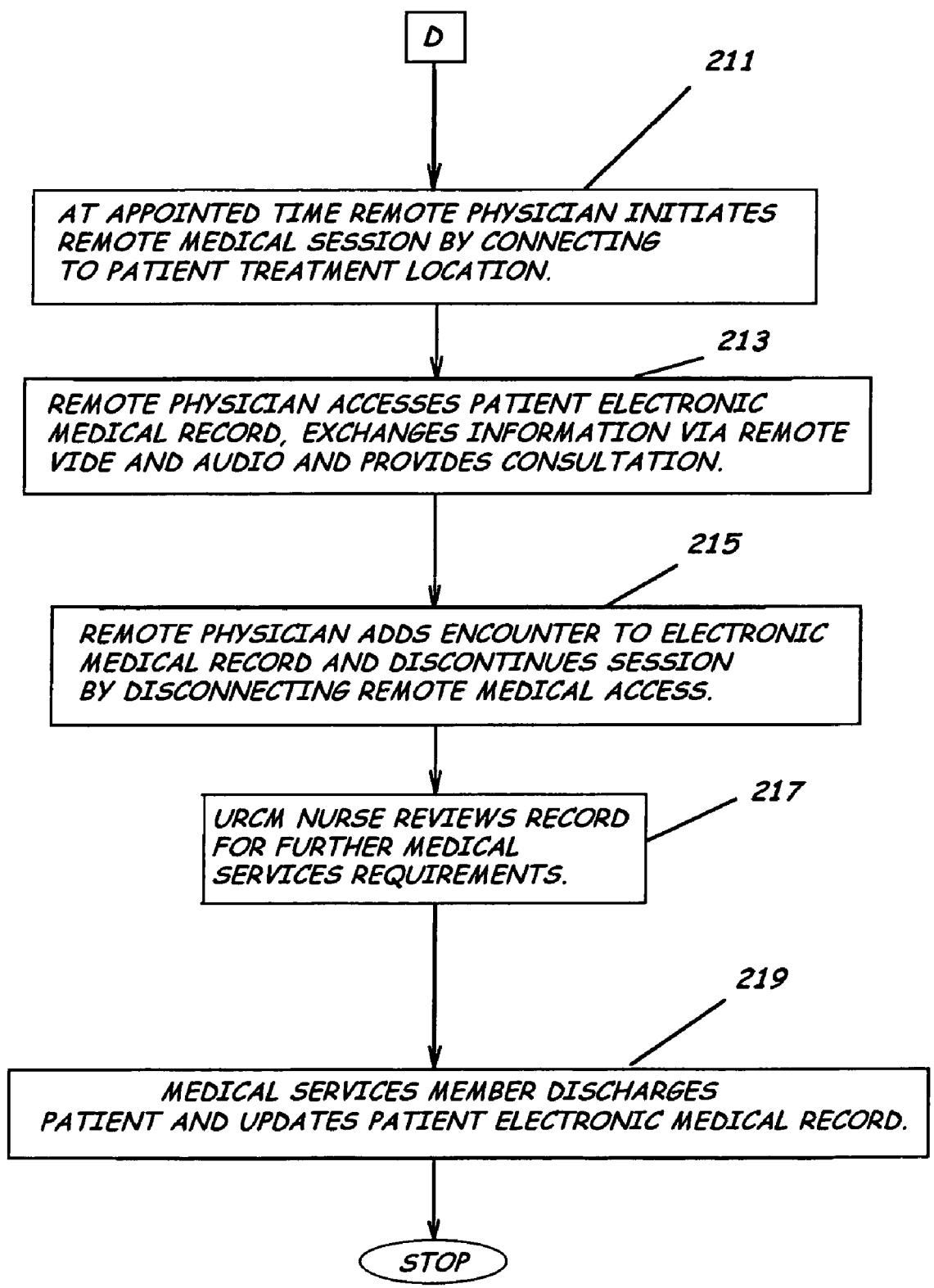

As shown in FIG. 6A-B, according to the preferred embodiment of the present invention, a method of providing specialist physician medical services includes creating a request for a patient medical services referral from a remote specialist physician for a patient (block 201), the request including pertinent patient clinical data about the patient's condition. According to an embodiment of the present invention, the request for specialist physician medical services along with the respective pertinent clinical data is entered in a MSRS 85 record preferably stored in a database associated with or accessible by a medical specialty referral system server 86, which can be either associated with or remote from the customer facility or site 33.

A preferably remotely located URCM nurse receives or is otherwise provided access to a daily list containing referral requests including those for specialist physician medical services, reviews associated patient electronic medical records 49, and evaluates the medical services requests using appropriate pre-selected screening criteria (block 203). According to an embodiment of the present invention, the URCM nurse accesses the memory 45 of a remote medical services server 43 to display predetermined specialist physician screening criteria according to the type of specialty requested, to thereby evaluate the request, comparing the patient clinical data against the predetermined screening criteria. The nurse documents/records in a MDMS record 89 the medical services request and associated clinical data along with the evaluation results. Note, according to an embodiment of the present invention, the MSRS record 85 and the MDMS record 89 can be consolidated in order to streamline the URCM nurse utilization review process.

If the URCM nurse determines the requested specialty physician medical services to be authorized, the nurse also documents the approval data and associated variance data, if any, in the MDMS record 89 (block 205). Then either by automated or manual process, the nurse also preferably accesses the MSRS record 85 and updates the medical services request status by appending the approval data to the medical services request. The remote medical services program product 51, in response to the authorization data in the MDMS record 89, automatically generates an authorization in the form of a hard-copy printout, e-mail notification, or other preferably electronic media.

A scheduler retrieves or is otherwise provided the authorization and schedules the approved medical services requested by the facility medical service provider (block 207). The scheduler makes the appointment for the requested medical services in the respective patient's electronic medical record using the remote medical services program product 51. The scheduler further can access the MSRS record 85 to update the request with the appointment data. The facility medical services provider preferably receives the MSRS approvals at least daily.

Preferably on the morning of the appointment, the medical service provider (remote physician extender), or alternatively the scheduler or a URCM nurse, or other authorized medical services member accesses the remote medical services program product 51 and patient electronic medical record 49 to admit the patient, adding the patient to a remote physician medical service delivery schedule, which initiates a remote patient medical service encounter with the scheduled remote specialist physician (block 209). A medical service provider (remote physician extender) at the customer facility clinic 34 and the remote specialist physician both access the daily schedule to determine their daily remote physician medical service delivery appointments.

At the scheduled time, the scheduled facility medical service provider and the patient are present at the patient medical service delivery station 37 associated with the facility clinic 34. The remote specialist physician initiates the remote physician medical service delivery, often referred to as a session, by connecting to the facility clinic 34 (block 211) using a remote physician medical service delivery suite control console 61 (FIG. 4). Upon establishment of the connection, the remote specialist physician can see and hear the patient and line data is transferred, and the facility medical service provider can begin the consultation.

The remote physician medical service delivery suite video display device functionality allows the display of the patient's electronic medical record 49 simultaneously with display of the patient and/or the facility medical service provider during the consultation. The remote specialist physician converses with the patient and the provider to gather data about the patient's condition (block 213). In addition to live video images of patient areas of interest, the provider, often referred to as a presenter, can provide the remote specialist physician immediate access to live video images of documents, charts, or electronic feed from a patient monitoring device, such video images simultaneously displayed with the video image of the patient/provider and the video image of the electronic medical record. For example, an orthopedic specialist physician may request to view x-rays if not already appended to the electronic medical record 49. A cardiologist physician may request the facility medical provider place an electronic stethoscope 69 on the patient for an electronic auscultation. Electrocardiographs, either direct electronic or hardcopy (through a document video visualizer 67), can also be transmitted to the remote specialist physician.

Further, as the remote specialist physician discusses the diagnosis and treatment plan with the patient and the provider, the remote specialist physician can record the encounter in the patient's electronic medical record 49 by accessing the remote medical services program product 51 functionality. The remote specialist physician preferably ends the remote physician medical services delivery by disconnecting the remote physician medical service delivery suite 35 from the patient medical service delivery station 37 (block 215). Any details not documented during the encounter can be documented thereafter preferably either using keyboard entry or through use of voice-activated dictation software.

The remote specialist physician, upon completion of documenting the encounter, preferably generates or makes available an extract of the encounter, either in electronic form, or in hard-copy print, and provides or otherwise transmits or makes available the extract to an associated remote URCM nurse. The nurse reviews the encounter data in the EMR to determine if the remote specialist physician has requested additional medical services (block 217). Further, preferably at the end of the business day or other predetermined time, a medical service member accesses the remote medical services program product 51 functionality reviews that all unmet needs are addressed, and discharges the patient, closing the encounter; and preferably accesses the MSRS record 85 to update the medical services referral request with the results of the remote medical services delivery appointment (block 219).

Figure 7:
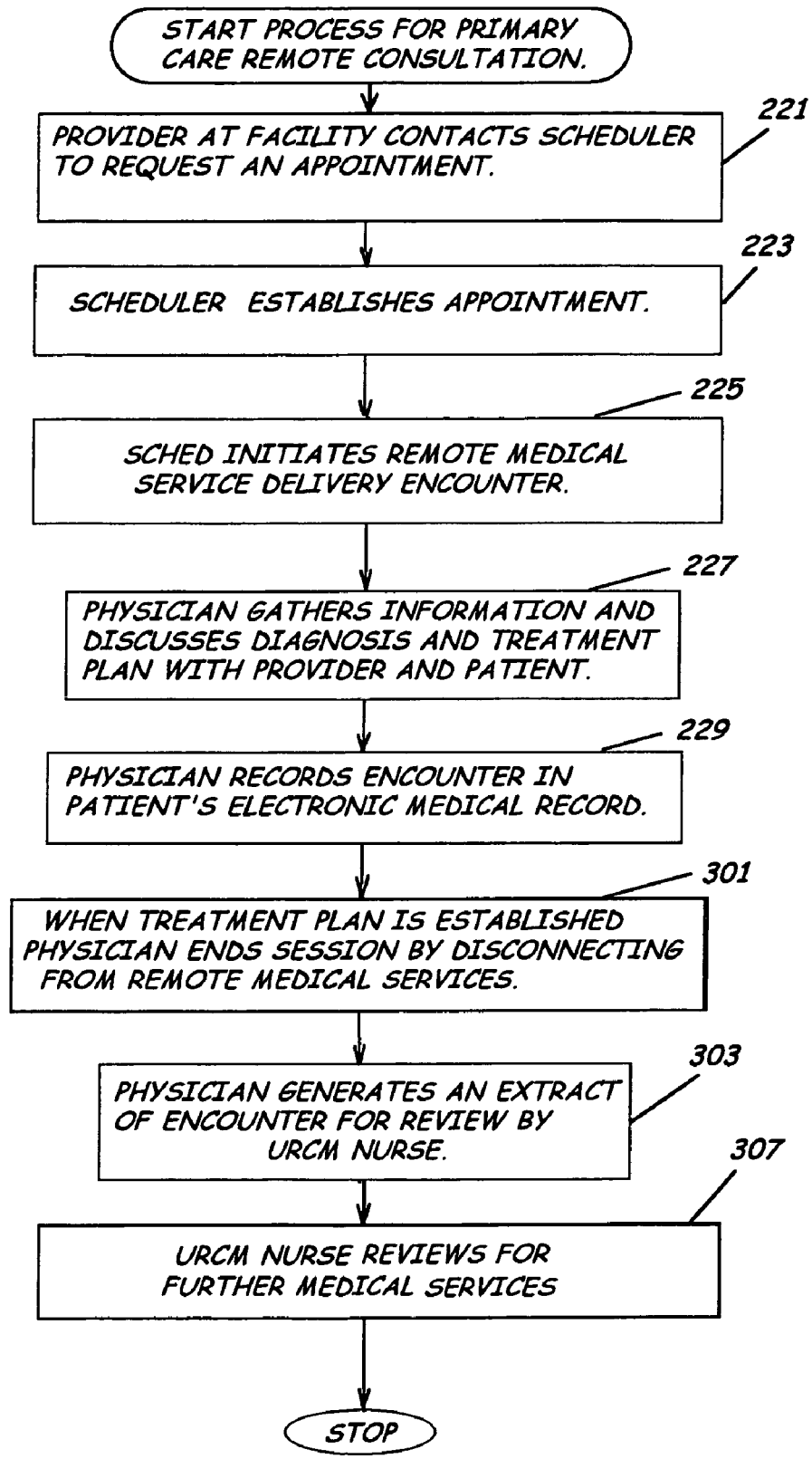
FIG. 7 is a schematic flow diagram of a method of providing enhanced medical service delivery according to an embodiment of the present invention.

As shown in FIG. 7, in an embodiment of the present invention, provided is a method of providing enhanced medical services delivery by a remote primary care physician to a patient being serviced in a customer facility having a medical service provider and a patient medical service delivery station 37, but where a patient needs to see a primary care physician and there is no such in-person physician available. Remote physician medical service delivery, according to embodiments of the present invention, allows a patient to talk with a remote primary care physician without the need to be transported.

Although according to most of the embodiments of the present invention, the customer facility or site 33 is provided an in-person primary care physician, there are situations where either a primary care physician cannot be supported or, more commonly, where the in-person primary care physician requires supplemental help in order to manage an excessive patient load, or even more commonly, where the facility only has a single in-person primary care physician, and that physician is unable to provide in-person medical service delivery. For example, the facility in-person primary care physician may be either on vacation or may be inflicted with a contagious or medical condition preventing in-person medical service delivery. Further, utilization of the remote physician medical service delivery suite 35 allows a primary care physician having a physical limitation preventing in-person medical service delivery to continue to provide medical services. Advantageously, the above described functionality provides for efficient utilization of primary care substitutes and negates the logistics and costs involved to transport the substitute primary care physician to the customer facility.

According to an embodiment of the present invention, a method of providing primary care physician medical services includes a medical service provider, usually a physician's assistant or nurse at a customer facility clinic 34, contacting or otherwise submitting a request to the scheduler for an appointment with a remote primary care physician for a patient (block 221). Subject to availability, the scheduler schedules the appointment for the same day utilizing the scheduling functionality of the remote medical services program product 51 (block 223). Further, prior to the scheduled time, the scheduler admits the patient, which creates a medical services delivery encounter (block 225). The remote primary care physician accesses the schedule to view the remote physician medical service delivery appointment.

Similar to the process described with respect to a remote specialist physician, at the scheduled time, the facility medical service provider and the patient are present at the patient medical service delivery station associated with the facility clinic. The remote primary care physician initiates the remote physician medical service delivery by connecting to the facility clinic 34 using a remote physician medical service delivery suite command console 61. Upon establishment of the connection, the remote primary care physician can see and hear the patient, and the facility medical service provider can begin the consultation. The remote physician medical service delivery suite 35 also can display the patient's electronic medical record 49 during the consultation.

The remote specialist physician converses with the patient and the provider to gather data about the patient's condition, discusses the diagnosis, and discusses the treatment plan (block 227). The remote primary care physician, preferably during the encounter, utilizing the associated remote medical peripherals to perform supplemental examinations, records details of the encounter in the patient's electronic medical record 49 (block 229). After a treatment plan is established, if required, the remote primary care physician preferably ends the session by disconnecting from the facility clinic (block 301). Any details not documented during the encounter can then be documented. The remote primary care physician, upon completion of documenting the encounter, then generates or otherwise makes available an extract of the encounter and can provide or otherwise transmit the extract to an associated remote URCM nurse (block 303). The nurse reviews the encounter data to determine if the remote primary care physician has requested additional medical services (block 307). Preferably at the end of the business day, the medical services member accesses the remote medical services program product 51 functionality and discharges the patient, closing the encounter, if not already closed.

Figure 8:
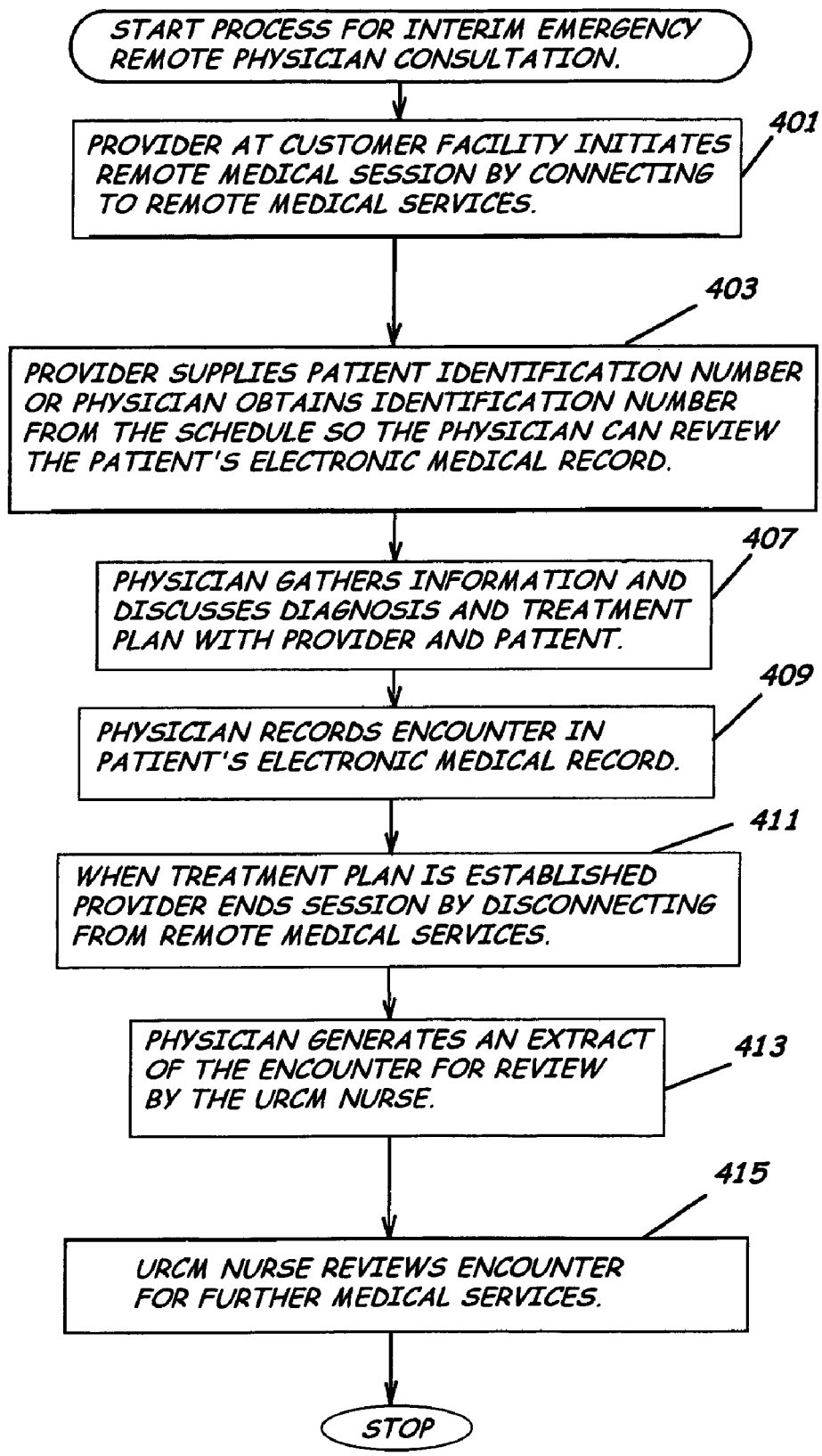
FIG. 8 is a schematic flow diagram of a method of providing enhanced hospital medical service delivery according to an embodiment of the present invention.

As perhaps best shown in FIG. 8, in an embodiment of the present invention, provided is a method of providing enhanced medical services delivery by a remote physician to a patient being serviced in a customer facility or site 33 having a medical service provider and a patient medical service delivery station 37, but where a patient needs to see a physician due to an emergency and there is no such in-person physician available. The remote physician medical service delivery, according to embodiments of the present invention, allow a facility medical service provider, utilizing associated remote medical peripherals, to talk with a remote physician, to perform supplemental examinations, either prior to contacting or prior to or during arrival of emergency medical services personnel.

According to the preferred embodiment of the present invention, a method of providing such emergency physician medical services includes a medical service provider, usually a physician's assistant or nurse at a customer facility clinic 34, initiating a remote physician medical service delivery by connecting the patient medical service delivery station 37 associated with the facility clinic 34 to the remote physician medical service delivery suite 35 (block 401). Upon establishment of the connection, the remote physician can see and hear the patient, and the facility medical service provider can begin the consultation. The facility medical service provider provides patient identifying data such as, the patient identification number, or the remote physician obtains the identification number from the schedule, so that the remote physician, utilizing the associated remote medical peripherals to perform supplemental examinations, can review the patient's electronic medical record 49 (block 403) during the consultation.

The remote physician converses with the provider and/or the patient to gather data about the patient's condition, discusses the diagnosis, and discusses the treatment plan (block 407). The remote physician, preferably during the encounter, records details of the encounter in the patient's electronic medical record 49 (block 409). After a treatment plan is established, the provider preferably ends the session by disconnecting from the physician remote site 31 (block 411). Any details not documented during the encounter can be documented thereafter. The remote physician, upon completion of documenting the encounter, preferably generates an extract of the encounter and provides, transmits, or otherwise makes available the extract for review by an associated remote URCM nurse (block 413). The nurse reviews the encounter data from the extract or directly from the patient electronic medical record 49 to determine if the remote physician has requested additional medical services (block 415). Preferably at the end of the business day, a medical services member accesses the remote medical services program product 51 functionality and, if not already done so, discharges the patient, closing the encounter.

According to embodiments of the present invention, implementation and use of electronic medical records 49, alone, can provide enhanced medical service delivery. For example, when the patient arrives at the facility clinic 34, a scheduling (intake) desk registers the patient by accessing functionality within the remote medical services program product 51, thereby creating an encounter. The intake desk then routes the patient to the appropriate facility medical service provider. A nurse assistant or other provider inputs the patient's vital sign data into the respective patient's electronic medical record 49. A facility nurse enters additional clinical data about the patient and indicates that the patient's data is ready for physician review. The facility primary care physician reviews the encounter data, updates it as necessary, records laboratory/medicine orders, and signs the encounter when it is complete.

Finally, a discharge nurse enters the diagnosis and procedure codes into the electronic medical record 49 and closes the encounter. Note also, for correctional facility patients, assisted living facility patients, and other long-term care facility patients needing to be seen on a regular basis at a facility affiliated clinic, a facility medical service provider can enter medical service requests into a facility scheduling system for the respective facility to interface with transportation scheduling, to thereby enhance medical service delivery. For example, with respect to a correctional facility, a correction facility medical service provider enters a medical service request into a correctional facility scheduling system. The prisoner transportation section then schedules the prisoner, the transportation vehicle, the vehicle driver, and any necessary security requirements.

Electronic medical record functionality can also be implemented with respect to ancillary medical services such as providing laboratory orders, radiology images, and pharmacy services. Implementation with respect to pharmacy services, in the context of a correctional facility example, is perhaps best described in two co-pending applications: U.S. Patent Application Ser. No. 10/806,878 by Clements et al., titled "Pharmaceutical Inventory and Dispensation Computer System and Methods," incorporated by reference, and U.S. Patent Application Ser. No. 10/959,627 by Clements et al., titled "Pharmaceutical Inventory and Dispensation Computer System and Methods," also incorporated by reference.

According to an embodiment of the present invention, utilizing a patient's electronic medical record 49 and functionality within the remote medical services program product 51, a medical service provider can create an appropriate laboratory order and perform various quality assurance checks such as, for example, quality assurance checks for duplicate laboratory orders and quality assurance checks for patient allergies. Upon satisfying the various quality assurance checks, a laboratory order and labels for a sample are printed. A sample technician retrieves the laboratory order and collects the sample from the patient. The sample technician then sends the laboratory orders, the associated label laboratory samples, and a log of the samples to a laboratory. If the laboratory is not granted full access to the network 39, the laboratory order data can be entered manually in a laboratory computer. If an automated laboratory system is used to conduct the laboratory tests and is connected to the laboratory computer system, the results are automatically entered into the laboratory computer system. The laboratory technician then accesses the laboratory computer system to either print out the laboratory results in order to fax, mail, or telephone the results to the facility medical service provider or, send the results via e-mail, or if granted some accesses to the network 39, enters the results directly into the respective patient electronic medical record 49, typically through use of HL-7 messages.

For radiology order requests, according to an embodiment of the present invention, utilizing a patient's electronic medical record 49 and functionality of the remote medical services program product 51, a medical service provider enters the radiology order request which print out the radiology order. The radiology technician then retrieves the order, takes the image, and sends the radiology order and the image to the radiologist. The radiologist reviews the image and enters the results directly into the patient's electronic medical record 49. Further, the image, if not already generated electronically, can be scanned and stored in a database, e.g. database 47, and can be associated with or appended to the patient's electronic medical record 49, to thereby provide ready access. The original image, if in a non-electronic form, can then be either sent to the facility clinic 34, placed in storage, or destroyed. A facility medical service provider can review the radiologist results by accessing the patient's electronic medical record 49.

According to embodiments of the present invention, the system 30 includes various methods that include the steps associated with treatment authorization and treatment review. Described below is the implementation of such utilization review and case management in the context of medical service delivery.

Figure 9:
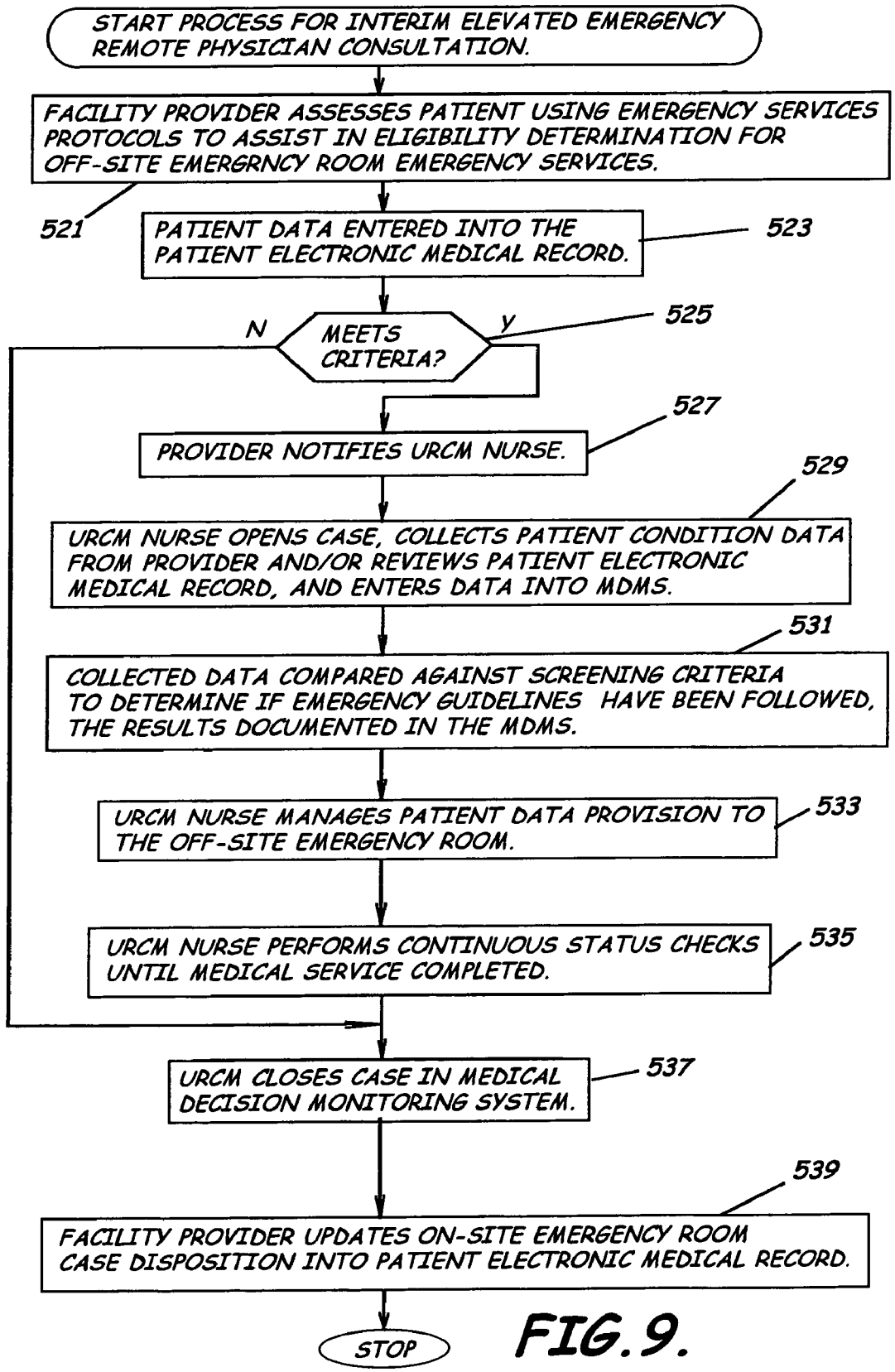
FIG. 9 is a schematic flow diagram of a method of providing enhanced emergency medical service delivery according to an embodiment of the present invention.

As shown in FIG. 9, in an embodiment of the present invention, provided is a method of providing enhanced emergency medical services delivery to a patient being serviced in a customer facility or site 33 having a medical service provider. According to the preferred embodiment of the present invention, the method includes a resident facility provider first prescreening a patient presented to the provider for emergency medical services eligibility at an off-site facility, such as, for example, a community or contract hospital 111 according to a pre-established protocol (block 521), to thereby determine if treatment is necessary, e.g., a likelihood of permanent injury or death unless treatment is rendered immediately. Regardless of the outcome of the prescreening, the results of the prescreening are entered in the respective patient electronic medical record 49 (block 523). If such eligibility determination is made (block 525), the provider or other facility member contacts emergency medical services to transport the patient to a medical treatment facility for emergency treatment.

The provider next, preferably via telephone or other immediate alert system known to those skilled in the art, contacts and informs a URCM nurse of the emergency (block 527), providing patient clinical data about the patient's condition, the hospital selected, and other pertinent data. The URCM nurse opens a case, collects patient health information for the patient from the medical service provider that prompted the request for emergency medical services and/or from the patient electronic medical record 49, and records or otherwise enters the data into a MDMS record 89 (block 529) preferably stored in the database 47 associated with the remote medical services server 43. The collected and recorded patient health information/data is then compared against predetermined emergency medical service screening criteria to determine if emergency medical services guidelines have been complied with. The results of the guidelines compliance determination are documented in the MDMS record 89 (block 531). If required, approval data and any associated variance data are recorded in the MDMS record 89. Because the evaluation can be made real-time during the telephone call with the facility medical services provider, the provider will know whether the requested emergency room evaluation has been approved.

The URCM nurse then manages provision of patient data (pre-certification data, if needed) to the destination medical treatment facility (block 533). Periodically, preferably every two to three hours until medical services are completed, the URCM nurse contacts the medical treatment facility to obtain follow-up patient disposition data (block 535), recording such status data in the MDMS record 89. Upon completion of medical service delivery to the patient and return of the patient, the URCM nurse closes the case in the MDMS (block 537). Correspondingly, the facility provider updates the patient disposition in the patient's electronic medical record 49 (block 539).

Figure 10:
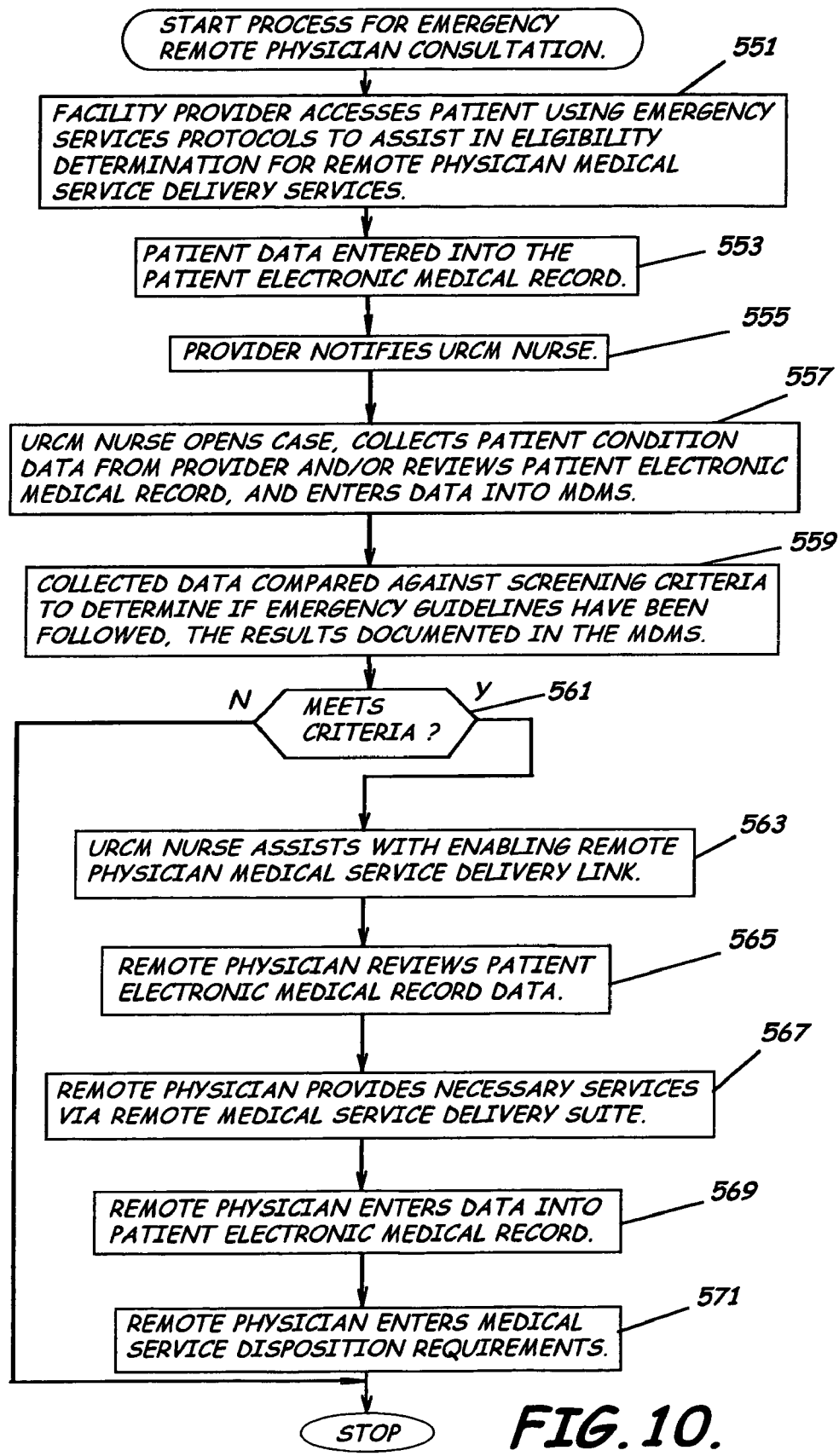
FIG. 10 is a schematic flow diagram of a method of providing enhanced medical service delivery in the form of an emergency room evaluation according to an embodiment of the present invention.

As shown in FIG. 10, in an embodiment of the present invention, provided is a method of providing enhanced emergency medical services delivery to a patient being serviced in a customer facility or site 33 having a medical service provider. According to the preferred embodiment of the present invention, the method includes a resident facility provider first prescreening a patient presented to the provider according to a pre-established protocol for emergency medical service eligibility via remote physician medical service delivery (block 551), to thereby determine if emergency treatment is necessary. Regardless of the outcome of the prescreening, the results of the prescreening are entered in the patient electronic medical record 49 (block 553).

If such eligibility determination is made, the provider, preferably via telephone or other immediate alert system, contacts and informs a URCM nurse of the emergency (block 555), providing patient clinical data about the patient's condition. The URCM nurse opens a case, collects patient health information for the patient from the medical service provider that prompted the request for emergency medical services and/or from the patient electronic medical record 49, and records or otherwise enters the data into a MDMS record 89 (block 557). The collected and recorded patient health information/data is then compared against predetermined emergency medical service screening criteria to determine if emergency medical services guidelines have been complied with. The results of the guidelines compliance determination are documented in the MDMS record 89 (block 559). If required, approval data and any associated variance data are recorded in the MDMS record 89. If the screening criteria have been satisfied (block 561), the URCM nurse further assists with enabling the remote physician medical service delivery link (block 563).

The remote physician, generally a specialist, reviews the patient electronic medical record 49 (block 565) and provides the necessary services via remote medical service delivery suite 35 (block 567). During and/or after the medical service delivery encounter, the remote physician enters the encounter data into the patient electronic medical record 49 (block 569), including patient disposition (block 571). There are several remote disposition options. For example, the remote physician can advise/request patient transit to an off-site facility emergency room. In such case, the remote physician notifies the provider at the customer facility or site 33 and the URCM nurse. Preferably, the remote physician also e-mails or otherwise makes available to, or provides reference to, the encounter data for review by the URCM nurse. The procedures thereafter are generally similar to those described with respect to FIG. 9 (blocks 531-539).

The URCM nurse accesses the memory 45 of a remote medical services server 43, displays predetermined screening criteria, and evaluates the request by comparing the encounter data against the predetermined screening criteria, to thereby determine if the appropriate guidelines have been followed.

The nurse documents/records the evaluation results along with the approval data and associated variance data, if any, in the MDMS record 89. The URCM nurse keeps the facility medical provider informed as to whether the advised treatment has been authorized. If the emergency room treatment is approved, either the URCM nurse or facility provider can contact appropriate personnel to procure the patient transportation. For example, if the facility is a correctional facility, the URCM nurse can contact correctional facility transportation personnel, if civilian, the URCM nurse can contact local EMS personnel. The URCM nurse also contacts the emergency room to provide an early warning of an expected patient arrival and the patient's initial diagnosis. After receiving the patient, the emergency room personnel then notify the URCM nurse of the patient arrival and post-evaluation disposition.

If still further treatment is determined to be required for greater than a preselected number of hours, e.g. an extended 23-hour observation or an extended medical treatment regime, the URCM nurse evaluates the proposed treatment, comparing the patient medical requirement against predetermined utilization screening criteria and records the results of the evaluation and associated authorization data in the MDMS record 89. According to the preferred embodiment of the present invention, the URCM nurse then closes the emergency room evaluation case and creates a new case for the patient. In an embodiment of the present invention, a URCM nurse affiliated with the hospital preferably assumes responsibility for the new case and performs follow-up operations including documenting the patient status in the MDMS record 89.

If the remote physician had initially determined a 23-hour observation was required, the process is similar to that described above except rather than the URCM nurse notifying the emergency room, the nurse preferably completes a bed registration and transmits or makes available to a record administrator the data contained therein. After the patient is transferred to the hospital 111, the URCM nurse affiliated with the hospital can assume responsibility for the patient.

The remote physician, during emergency medical service delivery, can alternatively advise referral for non-emergency managed care via remote specialist physician medical service delivery. In such case, the remote physician notifies the customer facility provider and the URCM nurse. The procedures for such non-emergency medical care via remote physician medical service delivery are described later (see block 620, FIG. 12A).

Further, the remote physician can return the patient to the facility provider for routine care. In such case, the remote physician notifies the provider at the customer facility or site 33 and the URCM nurse. The URCM nurse updates and closes the case in MDMS, and the facility personnel manage scheduling further routine care with the facility provider.

Still further, the remote physician can return medical service delivery for the patient to the provider at the customer facility or site 33, recommending no further action. Again, the remote physician notifies the facility provider and the URCM nurse of the patient's disposition. The URCM nurse updates and closes the case in MDMS, and the patient is restored to routine care with the facility provider.

Figure 11:
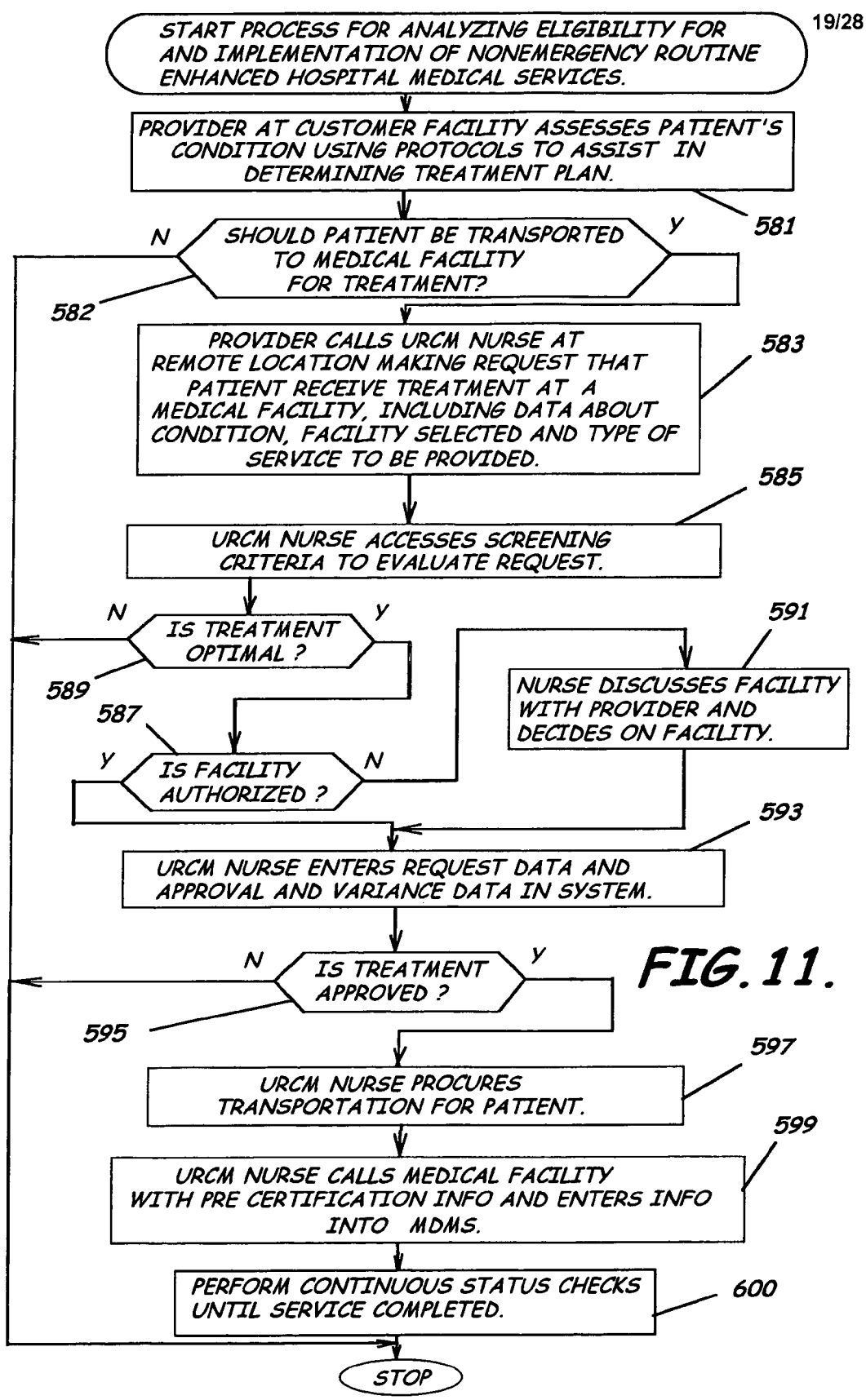
FIG. 11 is a schematic flow diagram of a method of providing enhanced hospital medical service delivery according to an embodiment of the present invention.

As shown in FIG. 11, in an embodiment of the present invention, provided is a method of providing routine enhanced hospital medical services delivery to a patient being serviced in a customer facility 33 having a medical service provider. According to an embodiment of the present invention, the method includes a resident facility provider first assessing the patient using pre-established protocols to thereby determine a proposed patient medical treatment according to a proposed treatment plan (block 581). If the medical service provider determines the patient should be transported to an external medical treatment facility (block 582), such as, for example, a community or contract hospital 111, the provider contacts, preferably via telephone, a URCM nurse and requests the proposed patient medical treatment at the desired hospital 111 (block 583). Information provided preferably includes patient clinical data about the patient's condition, the hospital selected, and the type of medical service to be provided by the hospital 111, e.g., emergency room evaluations, 23-hour observations, and outpatient procedures, and admissions.

The URCM nurse accesses the memory 45 of a remote medical services server 43 to display predetermined hospital admission screening criteria, to thereby evaluate the request (block 585), comparing the patient clinical data against the predetermined community hospital admission screening criteria. The nurse determines if the treatment is authorized (block 587) and, if authorized, the nurse can further determine if the facility is optimal (block 589), i.e., if an alternate facility is more appropriate due to such factors as cost, location, or quality of care. To do so, the nurse can access an online resource manual providing alternate hospital data.

According to the preferred embodiment of the present invention, the URCM nurse is empowered to discuss alternative facilities with the medical service provider (block 591), the provider, however, ultimately having the final say. The nurse records the requested patient treatment and the evaluation results along with the approval data and associated variance data, if any, in the MDMS record 89 (block 593). The nurse informs the medical service provider of whether the requested patient medical treatment is approved. If the treatment was approved (block 595), the nurse procures or helps procure patient transportation to the selected hospital (block 597) and provides the selected hospital pre-certification data (block 599). Periodically, preferably every two to three hours, the URCM nurse contacts the hospital 111 to obtain follow-up patient disposition data (block 600), recording such data in the MDMS record 89.

Figure 12A:
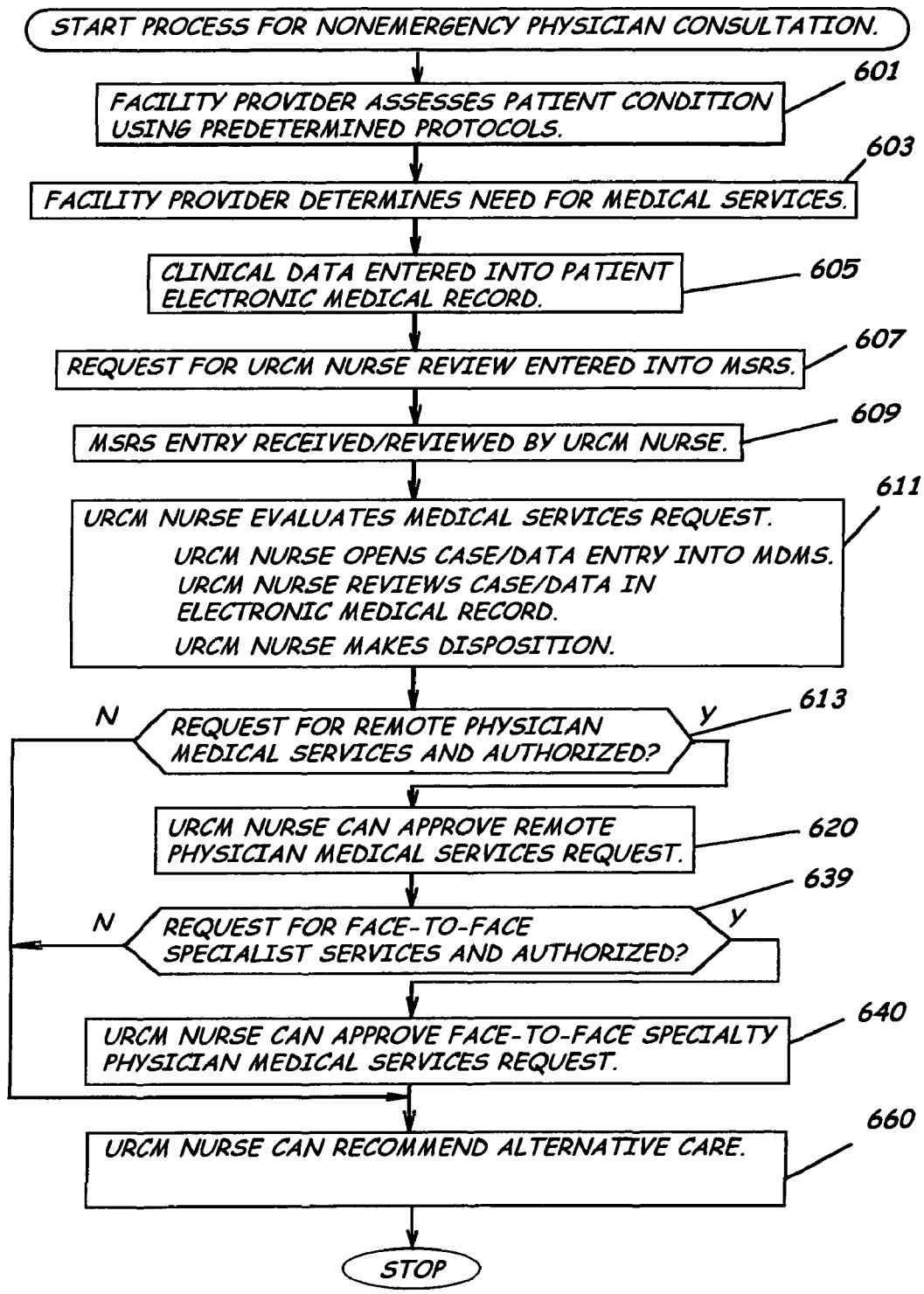
FIGS. 12A-12D are schematic flow diagrams of a method of providing enhanced medical service delivery in the form of scheduled medical services according to an embodiment of the present invention.

As shown in FIG. 12A, in an embodiment of the present invention, provided is a method of delivering enhanced non-emergency medical services in the form of scheduled medical services to a patient being serviced in a customer facility or site 33 having a medical service provider. According to the preferred embodiment of the present invention, the method includes a resident facility medical services provider first assessing a patient presented to the provider using pre-established protocols to assist in treatment plan determination (block 601). Such medical services include but are not limited to referrals to external medical treatment facility specialists, follow-up appointments, outpatient procedures, day surgeries, and scheduled admissions.

If medical services are determined warranted (block 603), a facility medical services provider enters the patient's clinical data in a respective patient electronic medical record 49 (block 605) and a facility member enters a request for the desired medical service in an MSRS record 85 (block 607). A preferably remotely located URCM nurse reviews the requests for services periodically or when specifically contacted (block 609), and evaluates (block 611) the medical service requests using appropriate pre-selected screening criteria. The URCM nurse opens a case, reviews patient health information for the patient from the patient electronic medical record 49, and documents/records in a respective MDMS record 89 the medical service request, associated clinical data, and the evaluation results.

Depending upon the type of medical services request, the URCM nurse generally has three major choices when evaluating such requests: authorize remote physician medical service delivery; authorize face-to-face medical service delivery; or propose an alternative to the requesting facility provider or physician. For example, if the requested service is for remote specialist physician medical services and is evaluated to be authorized (block 613), the URCM nurse can approve the request (block 640, FIG. 12C). Alternatively, the URCM nurse can recommend alternatives, described later (see block 660, FIG. 12D).

Figure 12B:
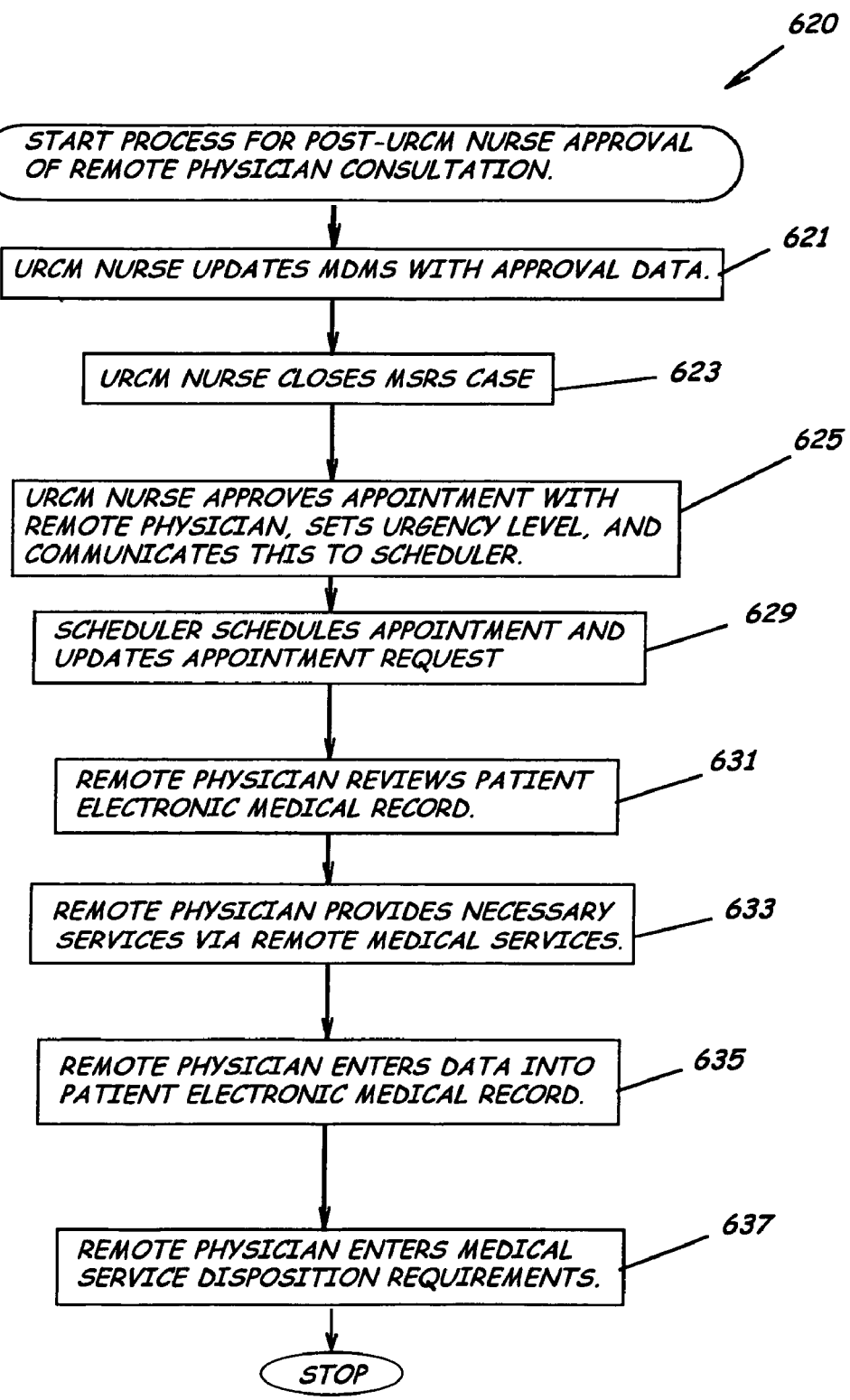

As shown in FIGS. 12A and 12B, if the remote services are approved (block 620), the URCM nurse updates the MDMS record 89, documenting the approval data and associated variance data, if any (block 621), and closes the MSRS case, updating the request status by appending the approval data to the request (block 623). The remote medical services program product 51, in response to the authorization data in the MDMS record 89, can automatically generate an authorization, preferably in electronic form, such as, for example, e-mail notification, other electronic media known to those skilled in the art, or alternatively in the form of a hard-copy printout. The authorization includes data such as, for example, priority (expedite or routine), sending facility, receiving physician, and any special patient instructions. The URCM nurse indicates approval of the remote physician medical services request in the respective patient electronic medical record 49 and in the MSRS record 85, assigns the approved appointment an appointment an urgency level, and communicates the approval to the scheduler (block 625). According to the preferred embodiment of the present invention, the urgency levels include the categories of "urgent" (preferably defined as that required no later than the next day), "expedite" (preferably defined as that required within the next 30 days), and "routine" (preferably defined as that required within the next 120 days).

According to an embodiment of the present invention, a scheduler retrieves or is otherwise provided the authorization and schedules the approved medical services requested by the facility medical service provider. The scheduler makes the appointment, according to the urgency level, for the requested medical services using a medical services scheduling and inpatient record program product, and accesses the MSRS record 85 to update the request with the appointment data (block 629). The facility medical services provider accesses the MSRS records 85 at least daily to determine if requests have been approved. The remote physician, generally a specialist, reviews the patient electronic medical record 49 (block 631) and provides the necessary services via the remote medical service delivery suite 35 (block 633). During and/or after the medical service delivery encounter, the remote physician enters the encounter data into the patient electronic medical record 49 (block 635), including patient disposition (block 637). This can be accomplished either through typing or speech dictation software.

There are several remote disposition options available to the physician. For example, the remote physician can recommend additional remote specialist physician medical service delivery. The remote physician preferably notifies the provider at the customer facility or site 33 and the URCM nurse of the selection, preferably via a clinical note in the electronic medical record 49. The remote physician can also e-mail or otherwise make available the encounter data for review by the URCM nurse. The URCM nurse generally either approves the advised services, as described above (see block 620), or recommends alternative care, as will be described later (see block 660, FIG. 12D). The remote physician can return the patient to the facility provider for routine care. In such case, the remote physician notifies the provider at the customer facility or site 33 and the URCM nurse. The URCM nurse updates and closes the case in MDMS, and the facility personnel manage scheduling further routine care with the facility provider. Further, the remote physician can return the patient recommending no further action. Again, the remote physician notifies the provider at the customer facility or site 33 and the URCM nurse. The URCM nurse updates and closes the case in MDMS, and the patient is restored to routine care with the facility provider. Still further, the remote physician can advise managing for direct emergency or urgent transport to an appropriate hospital, as described previously. Additionally, the remote physician can advise transit for direct face-to-face medical care, described below.

Figure 12C:
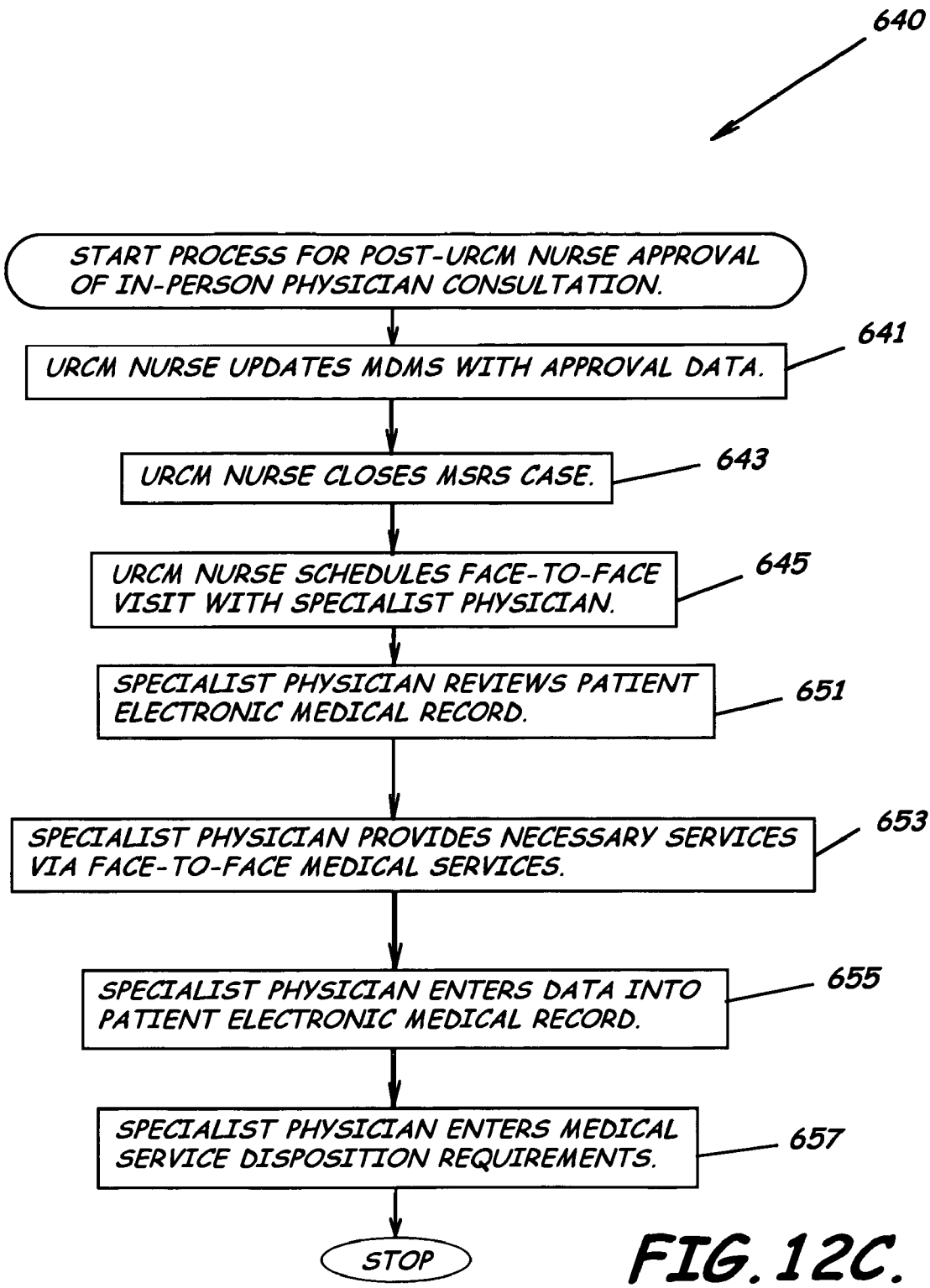

As shown in FIGS. 12A and 12C, if the requested service is for face-to-face specialist physician medical services and is evaluated to be authorized (block 639), the URCM nurse can approve the request (block 640). Alternatively, the URCM nurse can recommend and approve remote specialist physician medical service delivery (see block 620, FIG. 12B), or recommend alternatives, described later (see block 660, FIG. 12D). Note, according to an embodiment of the present invention, if the treatment plan includes a face-to-face referral to a specialist and the specialty is supported by remote physician medical service delivery, the requested medical referral service will be delivered via remote medical services delivery (e.g. remote specialist physician medical service delivery) prior to a determination that further face-to-face specialist services are required at an external medical treatment facility.

According to an embodiment of the present invention, if the face-to-face medical services are authorized and approved, the URCM nurse updates the MDMS record 89, documenting the approval data and associated variance data, if any (block 641), and closes the MSRS case, updating the request status by appending the approval data to the request (block 643). As described previously, the remote medical services program product 51, in response to the authorization data in the MDMS record 89, can automatically generate an authorization preferably in electronic form such as, for example, e-mail notification, other electronic media known to those skilled in the art, or alternatively in the form of a hard-copy printout. URCM nurse or scheduler can schedule the visit with the face-to-face specialist (block 645).

The URCM nurse or scheduler also can create a request for patient transport, if required. If the appointment is within seven days, the scheduler preferably either e-mails or otherwise provides a patient transport request to transportation personnel. If scheduled by a scheduler, the scheduler can provided appointment data to either the URCM nurse or a clerk who then accesses the MDMS record 89 and updates the medical services request by adding the appointment data. Note, in a correctional facility example, when the facility medical services provider enters a request for medical services to be provided by another prison clinic, the sequence of steps is similar to those described above, except the scheduler is instead preferably not involved.

The specialist physician reviews the patient electronic medical record 49 (block 651) and provides the necessary services via remote medical service delivery suite 35 (block 653). During and/or after the medical service delivery encounter, the remote physician enters the encounter data into the patient electronic medical record 49 (block 655), including patient disposition (block 657). There are several remote disposition options available to the specialist physician. The specialist physician preferably notifies the provider at the customer facility or site 33 and the URCM nurse of the selection via a clinical note entered into the patient's electronic medical record 49. Preferably, the specialist physician also e-mails or otherwise makes available the encounter data for review by the URCM nurse. The URCM nurse generally either approves the advised services, as described above (see block 640), or recommends alternative care as will be described later (see block 660, FIG. 12D).

The specialist physician can recommend additional face-to-face specialist physician medical service delivery. Alternatively, the specialist physician can instead recommend additional remote specialist physician medical service delivery for approval by the URCM nurse, as described above (see block 620, FIG. 12B). Further, the specialist physician can return the patient to the facility provider for routine care. In such case, the remote physician notifies the provider at the customer facility or site 33 and the URCM nurse. The URCM nurse updates and closes the case in the MDMS, and the facility personnel manage scheduling further routine care with the facility provider. Still further, the specialist physician can return medical service delivery responsibility for the patient to the provider at the facility or site 33, recommending no further action. The specialist physician notifies the provider at the customer facility or site 33 and the URCM nurse. The URCM nurse updates and closes the case in the MDMS, and the patient is restored to routine care with the facility provider.

Figure 12D:
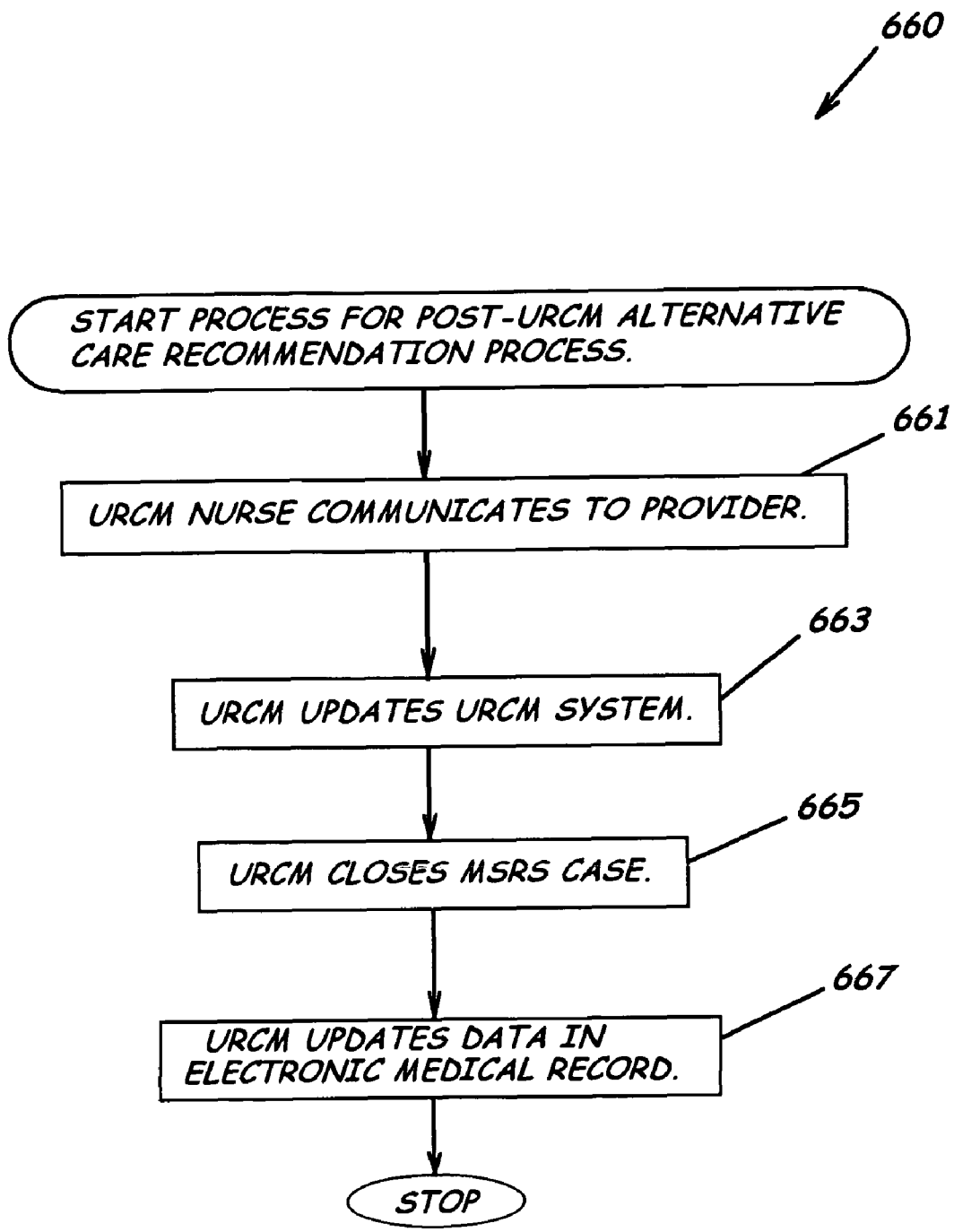

As shown in FIGS. 12A and 12D, the URCM nurse, performing the function of utilization review, can communicate to the provider recommendations for alternative medical services (block 661). For example, the URCM nurse can recommend the provision of additional medical services by a facility provider primary care physician rather than a remote specialist physician or recommend monitoring the patient in a facility infirmary, rather than transfer to an external hospital 111. These recommendations can take the form of discussions and negotiations with the requesting physician. Regardless of the recommendations, the URCM nurse updates the case in MDMS (block 663), closes the case in the MSRS (block 665), and updates data in the patient electronic medical record 49 (block 667). Unless one of the above described medical services is selected as a result of discussions with the requesting physician, the patient is generally restored to routine care with the facility provider.

Advantageously, according to embodiment of the present invention the system 30 provides for an active review process which maximizes information flow and allows for enhanced management of service utilization at facility affiliated hospitals 111, and thus, improved management of patient costs. The URCM nurse, performing the function of case management, accesses facility affiliated MSDS records 89 or electronic medical records 49 to generate a daily census report which lists all admitted patients. The nurse then performs a daily case review for each patient listed on the report in order to update the status of each respective patient, to thereby determine if the treatment plan is being followed and to provide authorizations if the treatment plan has been modified.

The URCM nurse accesses the MDMS records 89 for each respective patient, reviews previous case notes, and gathers information about the ongoing treatment of the patients from the hospital medical service provider and the MDMS records 89. The nurse also reviews any "paper" records not entered in the respective patient's electronic medical record 49 and consults the hospital medical service provider, if required, to determine if the treatment plan has been modified. The nurse also accesses laboratory, radiology, anthology, and procedure scheduling data to determine if, for example, the provider's laboratory and radiology orders are being filled promptly and if the provider is obtaining and reviewing the results promptly. This information is used to update the patient's case notes in the MDMS record 89. If the treatment plan was altered, the nurse accesses the memory 45 of a remote medical services server 43, displays predetermined screening criteria, and compares the treatment plan updates to the predetermined screening criteria. The URCM nurse determines if the updates are authorized and enters approval data and variance data, if any, into the MDMS record 89.

Note, according to the preferred embodiment of the present invention, as noted above, each facility-affiliated hospital 111 has its own URCM nurse. The facility affiliated hospital URCM nurse can provide authorizations needed for the patients at the hospital clinic. After the hospital provider has performed medical services on the patient, this nurse can review the provider's notes to determine if additional procedures, admissions, or appointments have been requested. Similar to the procedures for the remote URCM nurse, the hospital affiliated URCM nurse accesses the memory 45 of a remote medical services server 43, displays predetermined screening criteria, and compares the requests to the predetermined screening criteria. The nurse determines if the requests are authorized and enters approval data and variance data, if any, into the MDMS record 89. The nurse also reviews provider notes from any remote physician medical services delivery and provides authorizations, if required.

Figure 13:
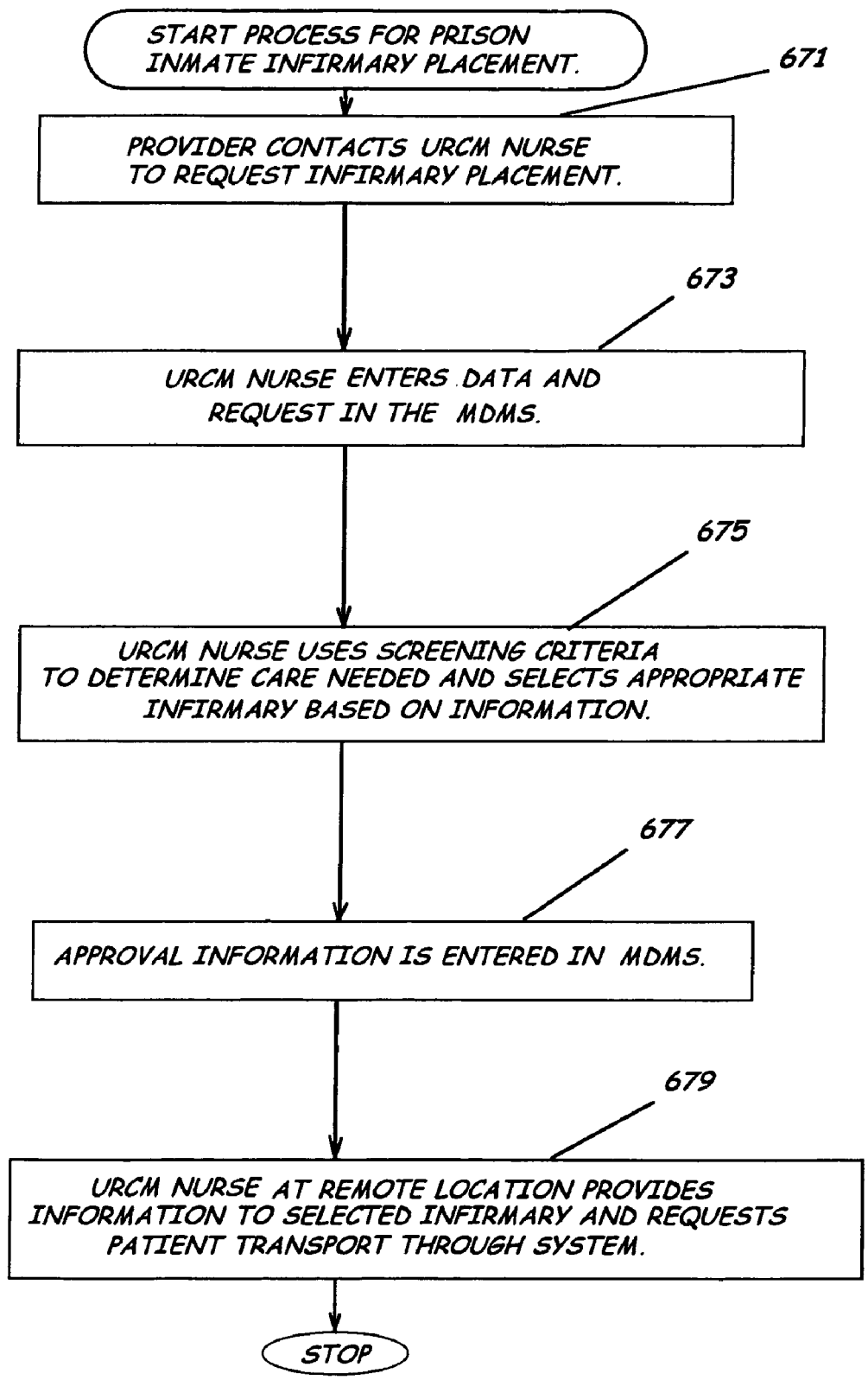
FIG. 13 is a schematic flow diagram of a method of providing enhanced medical service delivery according to an embodiment of the present invention.

As shown in FIG. 13, in an embodiment of the present invention, provided is a method of providing enhanced medical services delivery in the form of medical services to a patient prison inmate being serviced in medical treatment facility having a medical service provider. The medical treatment facility can include, for example, a prison clinic 34, a community hospital 111, or a prison affiliated hospital 111. According to the preferred embodiment of the present invention, the method includes a resident facility medical services provider first contacting, preferably via telephone, a remotely positioned URCM nurse, requesting infirmary placement (block 671). The nurse records the requested patient transfer and patient condition data in a MDMS record 89 (block 673). The URCM nurse accesses the memory 45 of a remote medical services server 43, displays predetermined screening criteria, and compares the collected data to the predetermined screening criteria. Using the predetermined screening criteria, the nurse determines the medical necessity and level of care needed and to authorize the infirmary placement (block 675). If authorized, the nurse selects the appropriate infirmary according to predetermined criteria such as, for example, the patient's medical needs, patient's custody status, geographic location of the infirmary, and infirmary that availability. To do so, the nurse can access an online resource manual and a bed availability board. The approval data and variance data, if any, are recorded in the MDMS record 89 (block 677). The nurse, during the telephone call, can inform the medical service provider of whether the requested infirmary is approved.

If the treatment was approved, the nurse provides the selected infirmary clinical data about the patient and procures patient transportation to the selected infirmary (block 679). Transportation procurement is preferably accomplished by sending a copy of the request (e-mail or fax), providing a transportation specialist (e.g. EMS dispatch) patient data (e.g., age, race, custody status, and isolation status). The nurse also preferably verifies receipt of the request through a follow-up telephone call. Note, the nurse preferably need not perform the transportation request step if the patient is being transferred from a facility clinic 34 to a facility infirmary, as arrangements are preferably made by the sending facility clinic 34. The URCM nurse routinely obtains follow-up patient disposition data on the patient placed in the infirmary, recording such data in the information diary of the MDMS record 89. The frequency of obtaining follow-up data is generally dictated by factors such as, for example, level of care required, acute, diagnosis, and the attributes of the selected infirmary.

Advantageously, according to an embodiment of the present invention, the system 30 provides for an active review process which maximizes information flow and allows for enhanced management of service utilization at the prison infirmaries, and thus, improved management of patient costs. The prison infirmary, preferably via e-mail or other electronic means, sends daily census reports to the URCM nurse. The nurse accesses the MDMS records 89 for those patients having open dispositions to generate a facility compliance report. Utilizing the prison infirmary census reports and facility compliance reports, the nurse determines which cases need to be reviewed. The review process includes reviewing patient case notes from the MDMS records 89 and contacting infirmary personnel to gather additional patient status data, such as, for example, patient status updates, patient response to medications, and rehabilitation process. The case notes are then updated by entering the gathered patient status data into the MDMS record case notes. The URCM nurse further accesses the memory 45 of a remote medical services server 43, displays predetermined screening criteria, and compares the collected data to the predetermined screening criteria. The nurse then enters approval data and variance data, if any, into the MDMS record 89. Note, the prison infirmary census reports are also used update the bed availability board which is used during infirmary placement, described above.

Advantageously, embodiments of the present invention also include procedures where either a remote, customer facility affiliated, or hospital affiliated URCM nurse determines that a medical service provider request fails to meet applicable predetermined screening criteria. For example, with respect to a customer correctional facility, the respective URCM nurse may determine that a request requires additional information or that a physician advisor must, and has not, reviewed the request. In such situation, the URCM nurse enters in the MDMS record 89 the status and any necessary supporting information and, according to the preferred embodiment of the present invention, as described above, accesses the respective MSRS record 85 and updates the request information by suspending the request and providing an explanation. The medical service provider accesses the MSRS records 85 daily to determine the status of any outstanding requests. If the suspension is due to a requirement for additional information, the medical service provider is given a predetermined time period in which to respond, e.g., 14 days, by providing the additional requested information. If the additional information is not provided within the predetermined time period, the nurse closes the request by updating the status information in the MDMS record 89.

Periodically, the remotely located URCM nurse accesses the MDMS records 89 to generate the suspended request report. For requests suspended due to an additional information requirement, the nurse determines if such additional information is provided and if the information is adequate according to the predetermined screening criteria. If the request is authorized, medical services are provided as described above. If there is still insufficient information to pass the screening criteria, the request is suspended for review by a physician advisor. In either situation, the nurse updates the request status in the MDMS record 89.

If the request was suspended for a previously requested physician advisor review, a notification letter to the physician advisor automatically prints out or otherwise delivered. According to the preferred embodiment of the present invention, the URCM nurse hand-carries a notification letter to the physician advisor who reviews the case and either approves or denies the request. The physician advisor's decision is provided to the nurse who then accesses the MDMS record 89 to update the request status accordingly. If the request is approved, medical services are provided, as described previously. If the request is denied, a letter notifying the medical service provider of the denial and an appeal is automatically printed or otherwise transmitted. The transmittal of the notification letter is documented.

If an appeal is made, the nurse accesses the MDMS records 89 and updates the request status to reflect the appeal. The physician advisor is provided a copy of or access to the appeal, which is then reviewed before a utilization review committee meeting where the request is either approved or denied. The results of the committee meeting are entered into the MDMS records 89, entry of which automatically generates a decision notification letter, which is sent or otherwise transmitted to the medical services provider, preferably by the URCM nurse. If the request is approved, medical services are provided as described above. If denied, additional appeals in accordance with predetermined procedures can be authorized. Regardless, the MDMS record 89 is updated to reflect the status of the request.

Figure 14:
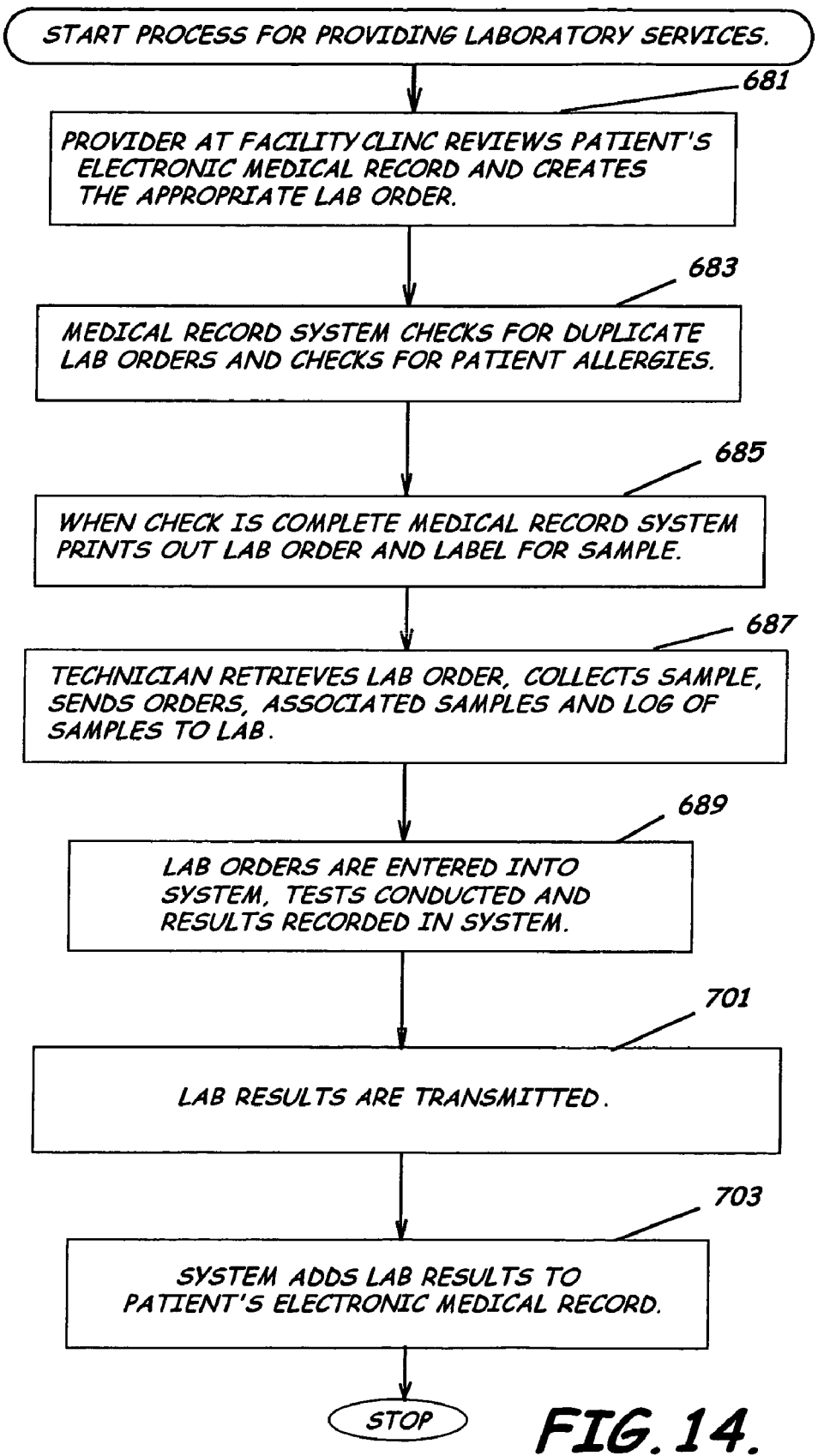
FIG. 14 is a schematic flow diagram of a method of providing enhanced medical service delivery in the form of laboratory services according to an embodiment of the present invention.

As shown in FIG. 14, according to an embodiment of the present invention, the system 30 includes various methods that can include the steps associated with providing laboratory services. For example, using a correctional facility customer for illustrative purposes only, a medical service provider at a facility clinic 34 can review a patient's electronic medical record 49 and create the appropriate laboratory order (block 681). The functionality in the remote medical services program product 51 checks for duplicate laboratory orders and checks for patient allergies (block 683). When the check is complete, the system prints out a laboratory order and labels for a sample (block 685). A technician then retrieves the laboratory order, collects the sample, sends the orders, associated samples, and log of the samples to the laboratory 115 (block 687). At the laboratory 115, the laboratory orders are entered into the system, tests are conducted, and the results are recorded (block 689). The laboratory results are then preferably electronically transmitted (block 701) and/or provided to the medical service provider at the facility clinic 34. The laboratory results are then directly added to an associated patient's electronic medical record 49 (block 703), or if provided via hard-copy, the laboratory results are scanned and added to the patient's electronic medical record 49 or "typed" directly into the record 49.

Figure 15:
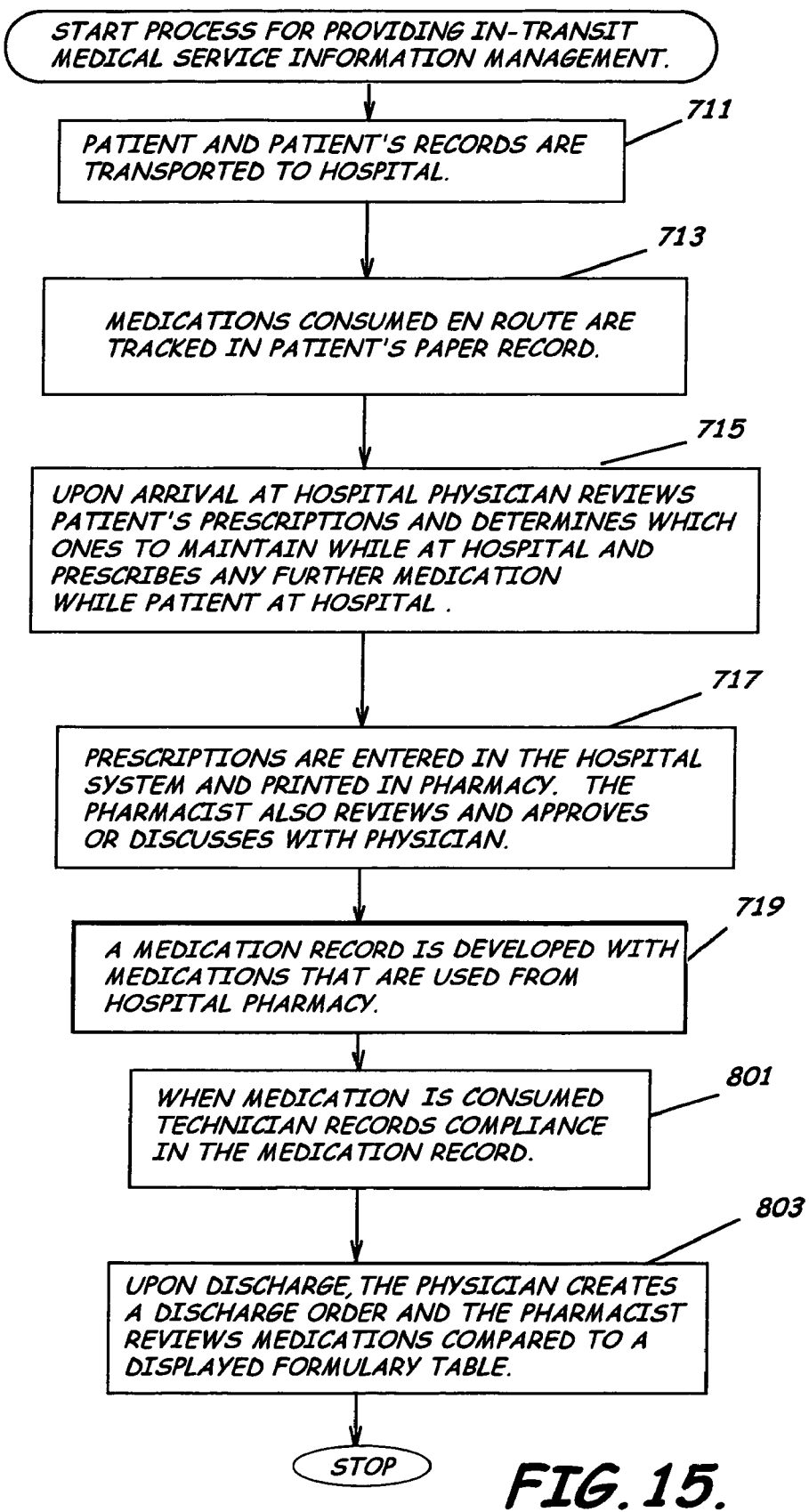
FIG. 15 is a schematic flow diagram of a method of providing enhanced hospital medical service delivery according to an embodiment of the present invention.

According to embodiments of the present invention, the system 30 includes various methods that can include the steps associated with providing in-transit medical service information management. For example, as shown in FIG. 15, in an embodiment of the present invention, medical services are provided to patients in transit. Such services can include, for example, monitoring patient medications during transportation to a hospital 111 through discharge from the hospital 111. The patient and patient's records are transported to the hospital 111 (block 711). Any medications consumed en route are tracked in a patient's paper record (block 713). Upon arrival at the hospital 111, a physician reviews the patient's prescriptions and determines which prescriptions to maintain while at the hospital 111 and prescribes any further required medications (block 715). If the hospital 111 does not support the electronic medical records 49, the prescriptions are entered in the hospital pharmaceutical system, which are reviewed and/or approved by the pharmacist (block 717). Approval may or may not require a discussion with the physician. Typically, a medication record is printed with the medications that are issued from the hospital pharmacy (block 719). When the medications are consumed, a hospital technician records compliance in the medication record (block 801). Upon discharge, the physician creates a discharge order and the pharmacist reviews the ordered medications compared to a displayed formulary table (block 803).

According to embodiments of the present invention, advantageously the system 30 also includes various methods that can include the steps associated with enrolling patients in the system 30. For example, the method can include transmitting or otherwise rendering available an enrollment file to the remote medical services server 43. The method can also include providing an enrollment processing program product (not shown) to perform error checking on the enrollment data, to process error-free entries, and to format the data for storage in MDMS records 89 and to transmit the formatted data to a remote medical services program product interface (not shown). The remote medical services program product interface performs additional formatting to either initialize new electronic medical records 49 or update pre-existing electronic medical records 49. Note, with respect to a correctional facility example, enrollment data can be provided for each new prison inmate upon entry or re-entry in the penal system or just-in-time when a prison inmate actually need medical care.

According to embodiments of the present invention, the system 30 also includes various methods that can include the steps associated with report generation and administration of the system 30. For example, functionality within the remote medical services program product 51 allows access to data within the electronic medical records 49 to formulate reports such as, for example, to allow for invoicing, invoice approval, formation of co-pay reports, and combine the data from the various reports.

Figure 16:
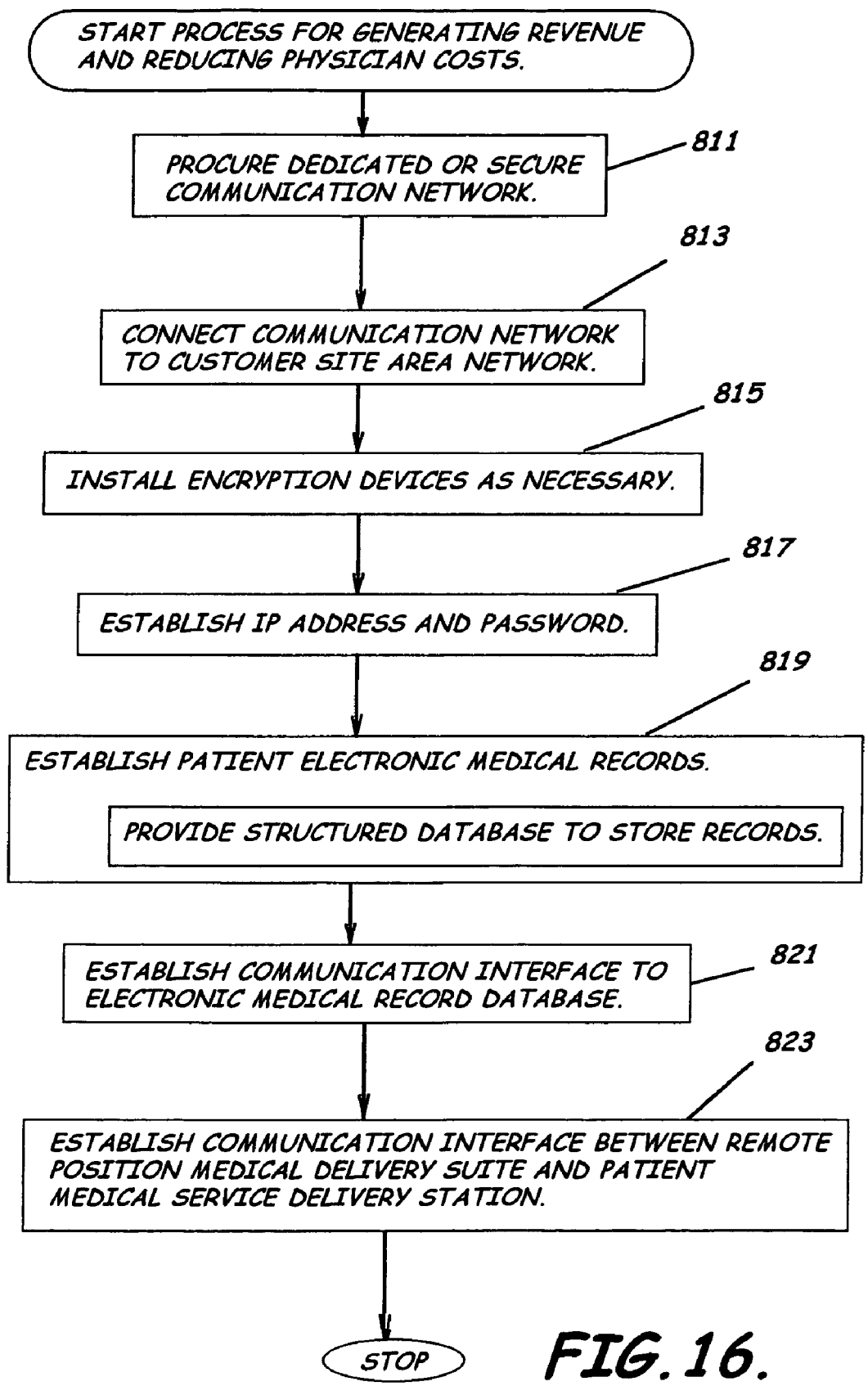
FIG. 16 is a schematic flow diagram of a method to enhance medical service delivery according to an embodiment of the present invention.

As shown in FIG. 16, embodiments of the present invention include a method of generating revenue from and reducing physician costs in providing medical services to a customer facility or site 33 such as, for example, correctional facility having a patient clinic 34. The method can include procuring a preferably broadband dedicated or secure communication network (block 811) between a remote physician facility or site 31, housing at least one but preferably a plurality of remote physician medical service delivery suits 35, to define a physician's private network 39. Although various types of network architecture are within the scope of the present invention, if available, utilizing T-1 lines each serially connected between a central remote physician site 31 and the customer site 33 has distinct advantages.

According to the preferred embodiment of the present invention, the above step is performed separately for each customer to provide each customer a substantially similar dedicated connection between the physician site 31 and a respective customer site 33. According to the preferred embodiment of the present invention, each customer site 33, even if owned by the same customer, is provided individual private physician network connections such that each customer site 33 is not normally afforded access to each other customer site 33. Note, other forms of communication network architecture such as, for example, satellite, cable, DSL, or ISDN, are within the scope of the present invention. For example, a virtual private network tunnel can be established over the Internet or one of the other forms of broadband. Note also, for the correctional facility example, if a land-based line is selected, the step includes coordinating with correctional facility site managers to provide access for the land-based line to enter the facility 33.

The communication link is then connected to a customer area network (block 813). The patient medical service delivery station 37, used to perform remote medical service delivery, and the customer computer or workstation 91, used by customer site medical service providers to access the electronic medical records 49, are correspondingly connected to the facility's area network (not shown). Note, this step includes coordinating with and providing a time limit to customer site personnel for the placement of at least one but preferably multiple patient medical service delivery stations 37. Positioning of the communication link may depend upon the physical location of the patient medical service delivery stations 37 depending upon the size of the customer facility or site 33 and/or customer preference. Depending upon the desired level of security and the network architecture selected, encryption devices (not shown) either in the form of hardware or software are then installed (block 815) at each end of the physician's private network 39 to prevent outside-network access. To complete establishment of communications between the remote physician facility 31 and the customer facility or site 33, an account number is established for each autonomous customer facility or site 33, each account number assigned an IP address and password (block 817).

Patient electronic medical records 49 are then established in a structured database 37 for each pre-identified patient and/or potential patient (prison inmate) in the correctional facility (block 819). The database 37, either physically or through software, is partitioned such that only entities connected to the individual customer's physician's private network 39 can access the electronic medical records 49. Specifically, with respect to a correctional facility, this further includes partitioning the database 47 such that individual prisons, even if owned or managed by the same customer entity, are preferably unable to access the records for other prisons.

A communications interface is then established with a remote medical services program product 51 (block 821) stored in memory 45 of the remote medical services server 43 associated with the central remote physician facility or site 31, the interface adapted to accept remote input from correctional facility medical personnel to access the patient electronic medical records 49. Further, a communications interface is established between a remote physician medical service delivery suite 35 (block 823) located at the central remote physician facility 31 and the patient medical service delivery station 37 positioned in the customer facility 33, the communications interface adapted to provide a video and audio connection between the remote physician medical service delivery suite 35 and the patient medical service delivery station 37.

Figure 17:
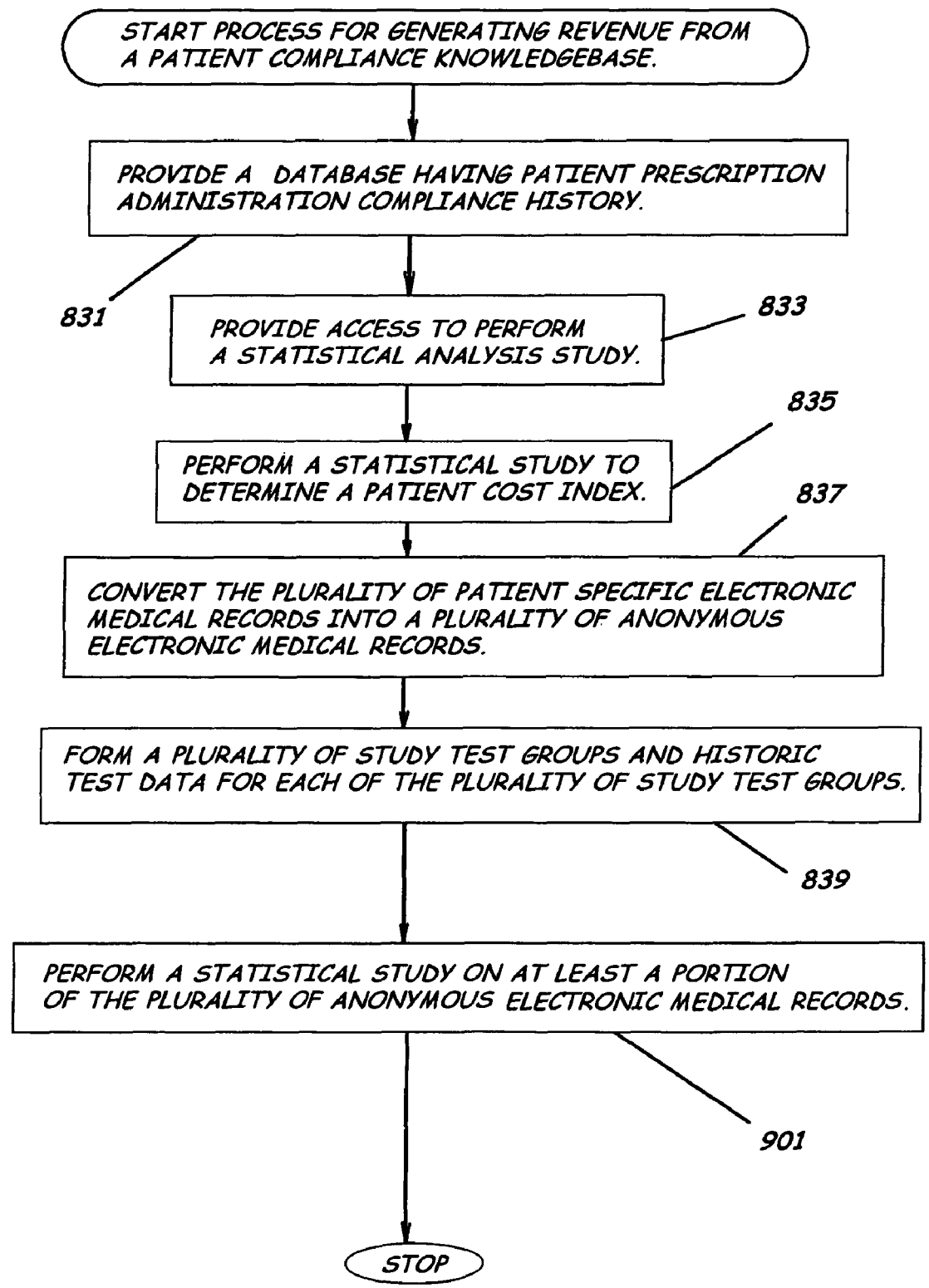
FIG. 17 is a schematic flow diagram of a method to enhance medical service delivery according to an embodiment of the present invention.

As shown in FIG. 17, embodiments of the present invention include a method of generating revenue from a patient medication compliance knowledgebase. The method can include providing a database 37 stored in memory of a computer for maintaining a plurality of patient specific electronic medical records 49 for individual patients, the records 49 including data indicating a patient medication prescription history for a plurality of prescribed medications having a predetermined set of delivery attributes, (e.g. route, dose, frequency) and a corresponding patient prescription administration compliance history for the prescribed medications (block 831). The method also includes providing access to the database 37 to perform a statistical analysis study on one or more of the prescribed medications, the study including analysis of medication compliance with at least one of the delivery attributes (block 833). Advantageously, in the preferred embodiment of the present invention, the database 37 can consist almost entirely of prison inmates whose medication compliance has been strictly monitored, adding a significant level of reliability to the database knowledge. Advantageously, the method can alternatively include performing a statistical study to determine a patient cost index (block 835) for enhancing remote medical service contract bidding and to forecast expected individual patient medical costs based on patient demographics, patient medical history, and historic patient medication administration compliance.

The method can also include removing patient identification data from the electronic medical records 49 to convert the plurality of patient specific electronic medical records 49 into a plurality of anonymous electronic medical records (block 837) to thereby form substantially instantaneously a plurality of study test groups and historic test data for each of the plurality of study test groups (block 839), and performing a statistical study on at least a portion of the plurality of anonymous electronic medical records for at least one of the plurality of medications (block 901).

It is important to note that while embodiments of the present invention have been described in the context of a fully functional system, those skilled in the art will appreciate that the mechanism of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include: nonvolatile, hard-coded type media such as read only memories (ROMs) or erasable, electrically programmable read only memories (EEPROMs), recordable type media such as floppy disks, hard disk drives and CD-ROMs, and transmission type media such as digital and analog communication links.

As shown in FIGS. 1A-17, embodiments of the present invention also include a computer readable medium that is readable by a computer to provide enhanced medical services delivery by a remote physician to a patient being serviced in a facility 33 having a patient medical service delivery station 37. For example, in an embodiment of the present invention, the computer readable medium includes a set of instructions that, when executed by the computer or computers, cause the computer or computers to perform the operations of: establishing a communications link in between a remote physician medical service delivery suite 35 and the patient medical service delivery station 37 through a communications network 39; displaying on a first remote physician medical service delivery suite video screen 57 an electronic medical record 49 of the patient; and displaying on a second remote physician medical service delivery suite video screen 55, 55', a real-time video image of the patient transmitted from the patient medical service delivery station 37, simultaneously while displaying the electronic medical record 49. The set of instructions can also cause the computer to perform the operation of displaying on a third remote physician medical service delivery suite video screen 59, 60, at least one of the following: a real-time visual image of non-electronically stored documents, electronic stethoscope data, and multifunctional videoscope data, transmitted from the patient medical service delivery station 37.

Also for example, in an embodiment of the present invention, the computer readable medium includes a set of instructions that, when executed by the computer or computers, cause the computer or computers to perform the operations of: capturing video images of the a remote physician to display to a patient positioned at a patient medical service delivery station 37; displaying patient areas of interest captured by a patient medical service delivery station video input device 65; and displaying a patient electronic medical record 49 of the patient so that the remote physician can review current patient medical administration data and can enter additional patient medical administration data. The instructions that, when executed by the computer, cause the computer to display patient areas of interest further can cause the computer to perform the following operations: displaying to the remote physician on a first video display 55 a near image of the patient area of interest when providing remote physician medical services, and displaying to the remote physician on a second video display a far image 55' of the patient area of interest when providing the remote physician medical services. Further, the instructions that, when executed by the computer, cause the computer to display a patient electronic medical record 49 can further cause the computer to perform the operation of displaying the electronic medical record 49 to the remote physician on a third video display 57 when providing the remote physician medical services.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That claimed is:

1. A system of enhanced medical services delivery to geographically distributed patients by remotely separated physicians located at a remote physician site, the system comprising:

an at least one remote medical information management computer including memory to store data therein to thereby define a remote medical services server;

a database associated with the remote medical services server and including a plurality of patient electronic medical records providing a single consolidated medical service delivery record for each of a corresponding plurality of patients, each record accessible by a patient clinic medical service provider, a medical services scheduler, and a remote physician;

a remote medical services program product stored in the memory of the remote medical services server and adapted to accept remote input from medical personnel to access the plurality of patient electronic medical records to thereby provide display of and data entry in a selected patient electronic medical record of a selected patient;

a dedicated communications link in communication with the remote medical services server and providing dedicated communications between a patient treatment location and the remote physician site located remote from the patient treatment location to thereby establish a private network connection between the patient treatment location and the remote physician site defining a private physician's network;

a plurality of patient medical service delivery stations each positioned in a patient clinic located at the patient treatment location and in communication with the remote medical services server through the private physician's network, each patient medical service delivery station including:
  a remotely controllable video input device to capture patient video images, the remotely controllable video input device controllable by the remote physician to provide enhanced patient viewing,
  a video display device positioned to be monitored by the patient clinic medical service provider and positioned to display patient video images captured by the patient medical service delivery station video input device and video images of the remote physician captured by a remote physician medical service delivery suite video input device ; and
  a computer in communication with the remote medical services server through the private physician's network and positioned to provide access to the remote medical services program product to provide data to display the selected patient electronic medical record, patient video images captured by the patient medical service delivery station video input device and video images of the remote physician to thereby provide feedback to the respective patient and patient clinic medical service provider; and
a remote physician medical service delivery suite positioned remote from the patient clinic at the remote physician site and in communication with the remote medical services server and each of the plurality of patient medical service delivery stations through the private physician's network to thereby facilitate the remote physician to perform remote patient medical service delivery through the remote physician medical service delivery suite and a respective patient medical service delivery station, the remote physician medical service delivery suite including:
  an audio input device to capture remote physician audio,
  a video input device to capture video images of the remote physician, and
  a plurality of video display devices including those to display patient areas of interest of the selected patient and to display the selected patient electronic medical record, and including:
    a first video display device configured to display near images of the patient area of interest of the selected patient,
    a second video display device configured to display far images of the patient area of interest of the selected patient, the first and the second video display devices together configured to simultaneously display both the near and far patient images of the patient area of interest of the selected patient to the remote physician when operating the remote physician medical service delivery suite with the respective medical service delivery station, and
    at least one electronic medical record video display to display portions of the selected patient electronic medical record of the selected patient to the remote physician when operating the remote physician medical service delivery suite with the respective medical service delivery station; and
the remote medical services program product including instructions that when executed by the remote medical services server cause the remote medical services server to perform the following operations:
  receiving remote input from medical personnel to initiate access to the plurality of patient electronic medical records to thereby provide display of and data entry in the selected patient electronic medical record,
  providing electronic medical record access to the patient clinic medical service provider through a computer located at the patient clinic and positioned remote from the remote physician medical services delivery suite and in communication with the remote medical services server through the private physician's network to thereby provide a computer-assisted review of current patient medical administration data by the patient clinic medical service provider and entry in and receipt of additional patient medical administration data into the selected patient electronic medical record,
  providing electronic medical record access to the medical services scheduler through at least one medical services scheduler computer positioned remote from the patient treatment location and in communication with the remote medical services server through the private physician's network to thereby provide a computer-assisted screening of the remote physician medical services request, examination of remote physician schedule availability, and scheduling of the remote physician and the patient clinic medical service provider by the medical services scheduler to thereby initiate remote patient medical service delivery to the selected patient through one of the plurality of patient medical service delivery stations at a preselected time,
  establishing a communications link between the remote physician medical service delivery suite and the patient medical service delivery station through the private physician's network to facilitate provision of remote physician medical services,
  providing electronic medical record access to the remote physician through the remote physician medical service delivery suite positioned remote from the patient clinic at the remote physician site and through the private physician's network to thereby provide patient electronic medical record access to the remote physician when the remote physician is providing remote physician medical services to the selected patient,
  providing data to display the real-time near video image of the patient area of interest of the selected patient received from the patient medical service delivery station, on a video display screen of the first video display device of the remote physician medical service delivery suite,
  providing data to display the real-time far video image of the patient area of interest of the selected patient received from the patient medical service delivery station, on a video display screen of the second video display device of the remote physician medical service delivery suite, and
  providing data to display the selected patient electronic medical record on a video display screen of the third video display device of the remote physician medical service delivery suite,
  simultaneously displaying the selected patient electronic medical record and both the real-time near and far video images of the selected patient to the remote physician when the remote physician is providing remote physician medical services responsive to operation of the remote physician medical service delivery suite with the patient medical service delivery station.

2. A system as defined in claim 1, further comprising:
at least one patient clinic computer associated with the patient clinic and positioned remote from the remote physician medical services delivery suite and in communication with the remote medical services server through the private physician's network, and adapted to provide access to the remote medical services program product to provide for remote computerized physician medical service request entry of a physician's medical service request by the patient clinic medical service provider and to display the selected patient electronic medical record to provide for computer-assisted review of the current patient medical administration data and entry in and receipt of additional patient medical administration data by the patient clinic medical service provider;
the at least one medical services scheduler computer positioned remote from the patient treatment location and in communication with the remote medical services server, adapted to provide access to the remote medical services program product to provide for the computer-assisted screening of the remote physician medical services request, examination of remote physician schedule availability, and scheduling of a remote physician and a patient clinic medical service provider, to thereby initiate remote patient medical service delivery to the selected patient through the one of the plurality of patient medical service delivery stations at the preselected time; and
at least one utilization review or case management computer in communication with the remote medical services server and adapted to provide access to the remote medical services program product, a medical services referral request record, and the patient electronic medical record, to provide computer-assisted utilization review of a remote physician medical services delivery request by a patient clinic medical service provider.

3. A system as defined in claim 1, further comprising:
a pharmacy located remote from the patient treatment location to provide pharmacy services;
at least one pharmacy computer positioned in the pharmacy and in communication with the remote medical services server and adapted to provide access to the remote medical services program product to display a patient electronic medical record for the selected patient to a pharmacy member to thereby provide pharmacy services; and
at least one pharmacy prescription compliance computer positioned remote from the pharmacy, in communication with the remote medical services server through the private physician's network and adapted to provide access to the remote medical services program product to thereby record a patient medication administration compliance for a respective patient medication order.

4. A system as defined in claim 1, further comprising:
a medical decision monitoring system server configured to receive and process document medical services requests, associated clinical data, medical services request evaluation results, and proposed modifications to the medical services requests entered by a utilization review or case management nurse; and
a database associated with the medical decision monitoring system server and including a plurality of medical decision monitoring system records accessible by the utilization review or case management nurse to document medical services requests, associated clinical data, medical services request evaluation results, and proposed modifications to the medical services requests.

5. A system as defined in claim 1, further comprising:
a treatment facility located remote from the patient treatment location to provide additional in-person physician medical services delivery not receptive to remote physician medical services delivery at the patient clinic; and
at least one treatment facility physician workstation positioned remote from the at least one physician medical service delivery suite and located in the treatment facility, in communication with the remote medical services server through the private physician's network and adapted to provide access to the remote medical services program product to display the patient electronic medical record for the preselected patient to a treatment facility physician to thereby provide treatment facility physician medical services.

6. A system as defined in claim 1,
wherein the system further comprises a treatment facility located remote from the patient treatment location and remote from the remote physician site to provide additional in-person physician medical services delivery;
wherein the private physician's network further comprises a dedicated communications link in communication with the remote medical services server providing dedicated communications between the treatment facility and the remote physician site to thereby establish a private network connection between the treatment facility and the remote physician site; and
wherein the system further comprises at least one patient medical service delivery station positioned in the treatment facility and in communication with the remote medical services server through the private network connection, and including a video input device to capture patient video images and a video display device adapted to be monitored by a treatment facility medical service provider.

7. A system as defined in claim 1,
wherein the video display device for each patient medical service delivery station is configured to display both patient video images captured by the patient medical service delivery station video input device and the video images of the remote physician captured by the remote physician medical service delivery suite video input device, to provide feedback to the respective patient and patient clinic medical service provider; and
wherein each patient medical service delivery station further comprises:
a video visualizer adapted to communicate with the remote physician medical service delivery suite, through the private physician's network to provide video visualizations of documents to the remote physician during the remote patient medical service delivery,
an electronic stethoscope adapted to communicate with the remote physician medical service delivery suite, through the private physician's network to provide for an electronic auscultation of a preselected patient,
a multi-function medical video scope adapted to communicate with the remote physician medical service delivery suite, through the private physician's network to provide ear, nose, and throat visualizations of a preselected patient to the remote physician during remote patient medical service delivery,
an ECG connected to ECG leads adapted to communicate with the remote physician medical service delivery suite through the private physician's network to provide electrocardiograph visualization of a preselected patient to the remote physician during remote patient medical service delivery, and a point-of-care laboratory testing device adapted to communicate with the remote physician medical service delivery suite through the private physician's network to provide real-time laboratory results during provision of the remote medical service delivery.

8. A system as defined in claim 1, wherein each patient medical service delivery station is adapted to be manned by a patient clinic physician and a patient clinic medical staff supporting member;

wherein the system further comprises a plurality of remote physician medical service delivery suites;

wherein the plurality of remote physician medical service delivery suites are adapted to be manned by a corresponding plurality of remote physicians; and wherein the remote patient medical service delivery is remotely provided through the remote physician medical service delivery suite by the patient clinic physician through one of the patient medical service delivery stations manned by the patient clinic medical staff supporting member responsive to the patient clinic physician being temporarily afflicted with a medical condition preventing provision of in-person patient medical services at the patient clinic, negating a need to provide an on-site replacement patient clinic physician, to thereby enhance physician-patient appointment attendance and reduce physician employment costs.

9. A system as defined in claim 1, wherein the patient medical service delivery station is positioned to provide remote monitoring of patient medication administration and to record corresponding patient medication self-administration compliance for a respective patient medication order.

10. A system of enhanced medical services delivery to geographically distributed patients by a remotely separated physician located at a remote physician site, the system comprising:

at least one remote medical information management computer including memory to store data therein to thereby define a remote medical services server;

a plurality of patient electronic medical records stored in the memory accessible to the remote medical services server and providing a medical service delivery record for a corresponding plurality of patients;

a remote medical services program product stored in the memory of the remote medical services server adapted to accept remote input from medical personnel to access the plurality of patient electronic medical records to thereby provide display of and data entry in a selected patient electronic medical record;

a patient medical service delivery station positioned in a patient clinic located at a patient treatment location in communication with the remote medical services server through a communications network and adapted to capture patient video images and to display remote physician video images; and a remote physician medical service delivery suite positioned remote from the patient clinic at the remote physician site and in communication with the patient medical service delivery station and the remote medical services server through the communications network and adapted to display patient video images and a respective selected patient electronic medical record, to thereby facilitate performing remote patient medical service delivery by the remote physician through the remote physician medical service delivery suite and the patient medical service delivery station, the remote physician medical service delivery suite including a plurality of video display devices, including:

a first video display device configured to display near images of a patient area of interest of the selected patient, a second video display device configured to display far images of the patient area of interest of the selected patient, the first and the second video display devices together configured to simultaneously display both the near and far patient images of the patient area of interest of the selected patient to the remote physician when operating the remote physician medical service delivery suite with the respective medical service delivery station, and at least one electronic medical record video display device configured to display at least portions of the selected patient electronic medical record of the selected patient to the remote physician when operating the remote physician medical service delivery suite with the respective medical service delivery station; and the remote medical services program product including instructions that when executed by the remote medical services server cause the remote medical services server to perform the following operations:

establishing a communications link between the remote physician medical service delivery suite and the patient medical service delivery station through the communications network to facilitate provision of remote physician medical services, providing electronic medical record access to a patient clinic medical service provider through the communications network to thereby provide a computer-assisted review of current patient medical administration data by the patient clinic medical service provider and entry in and receipt of additional patient medical administration data into the selected patient electronic medical record, providing electronic medical record access to the remote physician through the remote physician medical service delivery suite positioned remote from the patient clinic at the remote physician site and through the communications network to thereby provide electronic medical record access to the remote physician when the remote physician is providing remote physician medical services to the preselected patient, providing data to display a real-time near video image of the selected patient received from the patient medical service delivery station on the video screen of the first video display device of the remote physician medical service delivery suite, providing data to display a real-time far video image of the preselected patient received from the patient medical service delivery station on a video screen of the second video display device of the remote physician medical service delivery suite, and providing data to display the electronic medical record of the selected patient on a video screen of the at least one electronic medical record video display device of the remote physician medical service delivery suite, simultaneously displaying both the real-time near and far video images and the electronic medical record of the patient to the remote physician when the remote physician is providing remote physician medical services responsive to operation of the remote physician medical service delivery suite with the patient medical service delivery station.

11. A system as defined in claim 10, further comprising:
a medical services scheduler computer in communication with the remote medical services server and adapted to provide access to the remote medical services program product adapted to provide computer-assisted scheduling of a remote physician and the patient clinic medical service provider to thereby initiate remote patient medical service delivery to the selected patient through the patient medical service delivery station at a preselected time; and
a utilization review or case management computer in communication with the remote medical services server and adapted to provide access to the remote medical services program product, a medical services referral request record, and patient electronic medical records, to provide computer-assisted utilization review of a remote physician medical services delivery request by the patient clinic medical service provider.

12. A system as defined in claim 10, further comprising:
at least one pharmacy computer located in the pharmacy and in communication with the remote medical services server and adapted to provide access to the remote medical services program product to display the selected patient electronic medical record to a pharmacy member to thereby provide pharmacy services.

13. A system as defined in claim 10,
wherein the system further comprises a hospital located remote from the patient treatment location and remote from the remote physician site to provide additional in-person physician medical services delivery;
wherein the communications network further comprises a dedicated communications link in communication with the remote medical services server providing dedicated communications between the hospital and the remote physician site to thereby establish a private network connection between the hospital and the remote physician site; and
wherein the system further comprises at least one patient medical service delivery station positioned in the hospital and in communication with the remote medical services server through the private network connection, and including a video input device to capture patient video images and a video display device adapted to be monitored by a hospital medical service provider.

14. A system as defined in claim 10,
wherein the system further comprises a laboratory located remote from the patient treatment location and remote from the remote physician site to provide laboratory services; and
wherein the communications network further comprises a limited access communications link in communication with the remote medical services server providing communications between the laboratory and the remote physician site to thereby update the electronic medical records with laboratory data.

15. A system as defined in claim 10, further comprising:
a customer medical information management computer positioned at the patient treatment location and including memory to store data therein to thereby define a customer medical services server;
a duplicate copy of the patient electronic medical records stored in the memory of the customer medical services server associated with the patient treatment location; and
wherein the remote medical services program product is further adapted to perform the following operations:
maintaining the duplicate copy of associated electronic medical records,
simultaneously updating both the electronic medical records stored in the memory of the remote medical services server and the electronic medical records stored in the memory of a respective customer medical services server,
maintaining a log of electronic medical record changes, responsive to network interruption, and
reconciling the changes responsive to network reestablishment.

16. A system as defined in claim 10,
wherein the remote physician medical service delivery suite further comprises:
a computer having a memory and software stored in the memory and adapted to control video display image selection to define a physician command console, and
an automated encounter document creator stored in the memory to provide automated encounter document creation; and
wherein the remote physician medical service delivery suite is configured to receive and display multi-functional medical video scope visualizations for an electronic visualization of the patient's ear, nose, and throat, document visualizations and electrocardiograph visualizations, and audio from an electronic stethoscope, and point-of-care laboratory data.

17. A system as defined in claim 10,
wherein the remote physician medical service delivery suite includes a remote physician medical service delivery suite video input device adapted to capture remote physician video images; and
wherein the patient medical service delivery station further comprises:
a video input device to capture patient video images,
a video display device adapted to display patient video images captured by the patient medical service delivery station video input device and video images of the remote physician captured by the remote physician medical service delivery suite video input device, to provide feedback to the respective patient and patient clinic medical service provider, and
a computer in communication with the remote medical services server through the communications network and adapted to provide access to the remote medical services program product to provide for display of the patient electronic medical record.

18. A system as defined in claim 10, further comprising:
a plurality of remote physician medical service delivery suites adapted to be manned by a corresponding plurality of remote physicians to provide remote medical services simultaneously to a corresponding plurality of geographically separated patients, each remote physician medical service delivery suite including a plurality of video display screens to simultaneously display both near and far patient images; and
a plurality of patient medical service delivery stations, each including a remotely controllable video input device controllable by any one of the plurality of remote physicians to provide enhanced patient viewing.

19. A method of providing enhanced medical services delivery by a remote physician to a patient being serviced in a facility having a facility medical service provider and a patient medical service delivery station, the method comprising the steps of:

assigning a facility medical service provider to a patient medical service delivery station, the facility medical service provider defining a physician extender;

assigning a remote physician to a remote physician medical service delivery suite positioned at a remote physician site located remote from the facility having a physician extender and the patient medical service delivery station;

initiating a remote physician medical service delivery encounter by connecting the remote physician medical service delivery suite with the patient medical service delivery station through a communication network;

displaying a real-time live near video image of a patient area of interest of the patient being examined by the remote physician on a first remote physician medical service delivery suite video display screen of a plurality of remote physician medical service delivery suite video display screens, the real-time live near video image received from the patient medical service delivery station;

displaying a real-time live far video image of the patient area of interest of the patient being examined by the remote physician on a second remote physician medical service delivery suite video display screen, the real-time live far video image received from the patient medical service delivery station;

displaying an electronic medical record of the patient on a third remote physician medical service delivery suite video screen;

providing audio data of the remote physician from the remote physician medical service delivery suite to the patient medical service delivery station; and displaying a real-time live video image of the physician extender assisting the remote physician with examination of the patient area of interest through the remote physician medical service delivery suite and the patient medical service delivery station, simultaneously displaying the real-time live near video image of the patient area of interest being examined by the remote physician, the real-time live far video image of the patient area of interest being examined by the remote physician, the electronic medical record, and the real-time live video image of the physician extender assisting the remote physician with examination of the patient area of interest, and providing the audio data responsive to operation of the remote physician medical service delivery suite in communication with the patient medical service delivery station.

20. A method as defined in claim 19, further comprising: the step of transmitting the following to the remote physician medical service delivery suite for display on at least one other video display screen of the plurality of remote physician medical service delivery suite video display screens:

electronic stethoscope data for an electronic auscultation;
multi-functional video scope data for an electronic visualization of the patient's ear, nose, and throat; and
point-of-care laboratory data.

21. A method as defined in claim 19, further comprising the steps of:

producing an encounter record of the remote physician medical service delivery encounter by an automated encounter document creator configured to provide automated encounter document creation;

providing a utilization review or case management nurse access to the encounter record; and reviewing by the utilization review or case management nurse data comprising the encounter record to determine if additional medical services were requested and to perform a utilization review of the remote physician medical consultation encounter.

22. A method as defined in claim 19, further comprising the steps of:

requesting by the medical service provider a remote physician medical service delivery consultation referral;

providing consultation to the patient and the medical service provider during the remote physician medical service delivery encounter;

receiving feedback real-time from the patient and the medical service provider during the remote physician medical service delivery encounter responsive to the consultation;

recording data summarizing the remote physician medical consultation encounter; and updating a remote physician medical consultation referral request by a scheduler with results of the remote physician medical service delivery encounter.

23. A method as defined in claim 19, further comprising the steps of:

accessing a medical service delivery schedule by the medical service provider and the remote physician to determine their respective daily remote physician medical service delivery appointments; and reporting to the assigned medical service delivery suites at a substantially same predetermined scheduled time.

24. A method as defined in claim 19, wherein the remote physician assigned to the remote physician medical service delivery suite is a patient clinic physician, and wherein the step of initiating a remote physician medical service delivery encounter further comprises the step of:

providing the remote medical service delivery by the patient clinic physician responsive to the patient clinic physician being temporarily afflicted with a medical condition preventing provision of in-person patient medical services at the patient clinic, negating a need to provide an on-site replacement patient clinic physician, to thereby enhance physician-patient appointment attendance and reduce physician employment costs.

25. A method as defined in claim 19, further comprising the steps of:

evaluating a patient medical services request, the evaluation including the step of comparing patient clinical information contained in the patient medical services request against predetermined screening criteria;

generating an patient medical services request authorization for a remote patient medical service encounter with a scheduled remote specialist physician via an automated process responsive to the patient medical services request evaluation and responsive to approval data recordation;

accessing a patient electronic medical record and admitting the patient to add the patient to a remote physician medical service delivery schedule to thereby initiate the remote patient medical service encounter with the scheduled remote specialist physician; and providing the remote patient medical service delivery through the patient medical service delivery station and a remote physician medical service delivery suite remotely positioned with the scheduled remote specialist physician.

26. A method as defined in claim 25, further comprising the steps of:

accessing the patient electronic medical record by a scheduler on the scheduled date to admit the patient to thereby initiate the remote patient medical service encounter and to thereby add the remote patient medical service encounter to a daily physician work schedule; and accessing the remote physician medical service delivery schedule by the requesting medical service provider and the scheduled remote specialist physician to determine their respective daily remote physician medical service delivery appointments.

27. A method as defined in claim 19, further comprising the steps of:

providing point-of-care laboratory data to the remote physician medical service delivery suite, transmitted from the patient medical service delivery station; and displaying the point-of-care laboratory data on a fourth video display screen of the plurality of remote physician medical service delivery suite video display screens, when simultaneously displaying the real-time near video image on the first video display screen, the real-time far video image on the second video display screen, and the electronic medical record on the third video display screen.

28. A method as defined in claim 19, further comprising the step of:

remotely controlling a remotely controllable patient medical service delivery station video input device by the remote physician to capture patient video images of the patient, when simultaneously displaying the real-time near video image; the real-time far video image, and the electronic medical record.

29. A method as defined in claim 19, further comprising the steps of:

receiving electrocardiograph data for the patient from the patient medical service delivery station responsive to operation of the remote physician medical service delivery suite with the patient medical service delivery station when the remote physician is providing remote physician medical services; and displaying a visualization of the electrocardiograph data on a fourth video display screen of the plurality of remote physician medical service delivery suite video display screens, when simultaneously displaying the real-time near video image, the real-time far video image, and the electronic medical record.

30. A method as defined in claim 19, further comprising the step of:

providing automated encounter document creation to include providing real-time record transcriptions and preformatted remote services delivery templates selectable by the remote physician to thereby produce an encounter record of the remote physician medical service delivery encounter.

31. A method as defined in claim 19, further comprising the step of:

generating an automated patient medical services request authorization responsive to approval data recordation and responsive to a patient medical services request evaluation to include the step of comparing patient clinical information contained in the patient medical services request against predetermined screening criteria.

32. A tangible non-transitory computer readable medium that is readable by a computer to provide enhanced medical services delivery by a remote physician to a patient being serviced in a facility having a patient medical service delivery station, the non-transitory computer readable medium storing a set of instructions that when executed by the computer, cause the computer to perform the following operations:

establishing a communications link between a remote physician medical service delivery suite and the patient medical service delivery station through a communications network to facilitate provision of remote physician medical services, the remote physician medical service delivery suite positioned at a remote physician site located remote from the facility having the patient medical service delivery station;

providing data to display an electronic medical record of the patient on a first remote physician medical service delivery suite video display screen of a plurality of remote physician medical service delivery suite video display screens;

providing data to display a real-time near video image of a patient area of interest being examined by the remote physician received from the patient medical service delivery station, the real-time near video image of a patient area of interest being examined by the remote physician being displayed on a second remote physician medical service delivery suite video display screen; and providing data to display a real-time far video image of both the patient area of interest being examined by the remote physician and a physician extender located at the patient medical service delivery station and assisting the remote physician with the with examination of the patient area of interest, received transmitted from the patient medical service delivery station, the real-time far video image of both the patient area of interest being examined by the remote physician and the physician extender assisting the remote physician with examination of the patient area of interest being displayed on a third remote physician medical service delivery suite video display screen, simultaneously displaying the electronic medical record and both the real-time near video image of the patient area of interest being examined and real-time far video image of the patient area of interest being examined and the physician extender assisting the remote physician with examination of the patient area of interest, to the remote physician when the remote physician is providing remote physician medical services responsive to operation of the remote physician medical service delivery suite in communication with the patient medical service delivery station.

33. A non-transitory computer readable medium as defined in claim 32, further comprising a set of instructions that when executed by the computer, cause the computer to perform the following operations:

providing multi-functional video scope data to the remote physician medical service delivery suite received from the patient medical service delivery station, the multi-functional video scope data providing an electronic visualization of the patient's ear, nose, and throat;

providing data to display the multi-functional video scope data received from the patient medical service delivery station on a fourth video display screen of the plurality of remote physician medical service delivery suite video display screens; and providing document visualization video data generated from a document video visualizer and point-of-care laboratory data generated from a point-of-care laboratory testing device to the remote physician medical service delivery suite received from the patient medical service delivery station.

34. A non-transitory computer readable medium as defined in claim 32, further comprising a set of instructions that when executed by the computer, cause the computer to perform the following operations:

providing point-of-care laboratory data to the remote physician medical service delivery suite, received from the patient medical service delivery station; and providing data to display the point-of-care laboratory data on a fourth video display screen of the plurality of remote physician medical service delivery suite video display screens, when simultaneously displaying the real-time near video image, the real-time far video image, and the electronic medical record.

35. A non-transitory computer readable medium as defined in claim 32, further comprising a set of instructions that when executed by the computer, cause the computer to perform the following operation:

providing data to remotely control a remotely controllable patient medical service delivery station video input device by the remote physician to capture patient video images of the patient, when simultaneously displaying the real-time near video image, the real-time far video image, and the electronic medical record.

36. A non-transitory computer readable medium as defined in claim 32, further comprising a set of instructions that when executed by the computer, cause the computer to perform the following operations:

receiving electrocardiograph data for the patient from the patient medical service delivery station responsive to operation of the remote physician medical service delivery suite with the patient medical service delivery station when the remote physician is providing remote physician medical services; and providing data to display a visualization of the electrocardiograph data on a fourth video display screen of the plurality of remote physician medical service delivery suite video display screens, when simultaneously displaying the real-time near video image, the real-time far video image, and the electronic medical record.

37. A non-transitory computer readable medium as defined in claim 32, further comprising a set of instructions that when executed by the computer, cause the computer to perform the following operation:

providing automated encounter document creation to include providing real-time record transcriptions and preformatted remote medical services delivery templates selectable by the remote physician to thereby produce an encounter record of the remote physician medical service delivery encounter.

38. A non-transitory computer readable medium as defined in claim 32, further comprising a set of instructions that when executed by the computer, cause the computer to perform the following operation:

generating an automated patient medical services request authorization responsive to approval data recordation and responsive to patient medical services request evaluation data to include the operation of performing an automated comparison of patient clinical information contained in the patient medical services request against predetermined screening criteria.

39. A non-transitory computer readable medium as defined in claim 3, wherein the operation of providing data to display a patient electronic medical record includes the operations of providing data to display portions of the electronic medical record to the remote physician on two separate video display screens when the remote physician is providing the remote physician medical services.

40. A non-transitory computer readable medium as defined in claim 32, further comprising a set of instructions that when executed by the computer, cause the computer to perform the following operation:

providing a laboratory a limited access communications link to the electronic medical records to provide for updating the electronic medical records with laboratory data.

41. A tangible non-transitory computer readable medium that is readable by a computer to provide enhanced medical services delivery by a remote physician to a patient being serviced in a facility having a patient medical service delivery station, the non-transitory computer readable medium storing a set of instructions that when executed by the computer, cause the computer to perform the following operations:

capturing video images of the a remote physician with a video input device positioned at a remote physician medical service delivery suite to display the video images of the remote physician to a patient facility medical service provider defining a physician extender positioned to assist the remote physician and to a patient when the remote physician is providing remote physician medical services, the video images of the remote physician displayed on a video display device positioned at the patient medical service delivery station defining a patient medical service delivery station video display device, the remote physician medical service delivery suite located remote from the facility having the patient medical service delivery station;

providing data to display patient areas of interest captured by a patient medical service delivery station video input device and the video images of the remote physician captured by the remote physician medical service delivery suite video input device when the remote physician is providing remote physician medical services, the video images of patient areas of interest and the video images of the remote physician displayed on the patient medical service delivery station video display device to thereby provide feedback to the patient and physician extender;

providing data to display a patient electronic medical record of the patient on the patient medical service delivery station video display device to thereby provide for review of current patient medical administration data and entry in and receipt of additional patient medical administration data to the patient medical service delivery station;

receiving electronic medical record data entered by the physician extender through the patient medical services delivery station;

providing data to display a real-time live near image of a patient area of interest being examined by the remote physician to the remote physician on a first video display screen of a remote physician medical service delivery suite when the remote physician is providing remote physician medical services;

providing data to display a real-time live far image of the patient area of interest being examined by the remote physician to the remote physician on a second video display screen of the remote physician medical service delivery suite when providing the remote physician medical services; and providing data to display the electronic medical record of the patient on a third video display screen of the remote physician medical service delivery suite, simultaneously displaying to the remote physician both the real-time live near image of the patient area of interest being examined by the remote physician on the first video display screen, the real-time live far image of the patient area of interest being examined by the remote physician on the second video display screen, and portions of the electronic medical record entered by the physician extender assisting the remote physician in examining the patient area of interest on the third video display screen, when the remote physician is providing remote physician medical services through operation of the remote physician medical service delivery suite in communication the patient medical service delivery station.

42. A system of enhanced medical services delivery to geographically distributed patients by remotely separated physicians located at a remote physician site, the system comprising:

at least one remote medical information management computer including memory to store data therein to thereby define a remote medical services server;

a dedicated communications link in communication with the remote medical services server and providing dedicated communications between a patient treatment location and the remote physician site located remote from the patient treatment location to thereby establish a private communications network connection between the patient treatment location and the remote physician site, defining a private physician's network;

a database associated with the remote medical services server and including a plurality of patient electronic medical records providing a single consolidated medical service delivery record for each separate one of a corresponding plurality of patients that combines both outpatient and inpatient records, each consolidated record accessible by a patient clinic medical service provider, a medical services scheduler, and a remote physician;

a plurality of patient medical service delivery stations each positioned in a patient clinic located at the patient treatment location, in communication with the remote medical services server through the private physician's network, and each patient medical service delivery station including:

a remotely controllable video input device to capture patient video images, the remotely controllable video input device controllable by the remote physician, to provide enhanced patient viewing, a video display device positioned to be monitored by the patient clinic medical service provider and configured to display patient video images captured by the patient medical service delivery station video input device and a video image of the remote physician captured by a video input device of a remote physician medical service delivery suite to thereby provide feedback to the respective patient and patient clinic medical service provider, a patient medical delivery station computer in communication with the remote medical services server through the private physician's network, and including memory and software stored in the memory and positioned to provide access to remote medical services program product and to provide for display of a patient electronic medical record, a video visualizer adapted to communicate with the remote physician medical service delivery suite through the private physician's network to provide video visualizations of documents to the remote physician during the remote patient medical service delivery, an electronic stethoscope adapted to communicate with the remote physician medical service delivery suite through the private physician's network to provide for an electronic auscultation of a preselected patient, a multi-function medical video scope adapted to communicate with the remote physician medical service delivery suite through the private physician's network to provide ear, nose, and throat visualizations of a preselected patient to the remote physician during remote patient medical service delivery, an electrocardiograph connected to electrocardiograph leads adapted to communicate with the remote physician medical service delivery suite through the private physician's network to provide electrocardiograph visualization of a preselected patient to the remote physician during remote patient medical service delivery, and a point-of-care laboratory testing device adapted to provide real-time laboratory results during provision of the remote medical service delivery;

the remote physician medical service delivery suite positioned remote from the patient clinic at the remote physician site and in communication with the remote medical services server and each of the plurality of patient medical service delivery stations through the private physician's network to thereby allow the remote physician to perform remote patient medical service delivery through the remote physician medical service delivery suite and a respective patient medical service delivery station, the remote physician medical service delivery suite including:

an audio input device to capture audio, a video input device to capture video images of the remote physician, and a plurality of video display screens positioned to simultaneously display to the remote physician both near and far patient images of a patient area of interest, portions of a patient electronic medical record, and one or more of the following: multi-functional video scope data and point-of-care laboratory data for the preselected patient, when operating the remote physician medical service delivery suite and a respective one of the plurality of medical service delivery stations, the plurality of video display screens comprising:

a first video display screen positioned to display a near image of the patient area of interest of the preselected patient to the remote physician when providing remote physician medical services, a second video display screen positioned to display a far image of the patient area of interest to the remote physician when providing the remote physician medical services, a third video display screen positioned to display portions of an associated patient electronic medical record of the preselected patient to the remote physician, a fourth video display screen also positioned to display portions of the associated patient electronic medical record of the preselected patient to the remote physician, and a fifth video display screen positioned to display one or more of the following: multi-functional video scope data and point-of-care laboratory data defining auxiliary data, transmitted from the patient medical service delivery station; and the remote medical services program product including instructions that when executed by the remote medical services server cause the remote medical services server to perform the following operations:

establishing a communications link between the remote physician medical service delivery suite and a respective one of the plurality of patient medical service delivery stations through the private physician's network to facilitate provision of remote physician medical services, providing electronic medical record access to a patient clinic medical service provider through the private physician's network to thereby provide a computer-assisted review of current patient medical administration data by the patient clinic medical service provider and entry in and receipt of additional patient medical administration data into the selected patient electronic medical record, providing electronic medical record access to the remote physician through the remote physician medical service delivery suite positioned remote from the patient clinic at the remote physician site and through the private physician's network to thereby provide electronic medical record access to the remote physician when the remote physician is providing remote physician medical services to the preselected patient, providing data to display a real-time near video image of the selected patient received from the respective patient medical service delivery station on the first video display screen of the of the remote physician medical service delivery suite, providing data to display a real-time far video image of the preselected patient received from the respective patient medical service delivery station on the second video display screen of the remote physician medical service delivery suite, providing data to display the electronic medical record of the selected patient on the third video display screen of the remote physician medical service delivery suite, and providing data to display the multi-functional video scope data, and the point-of-care laboratory data transmitted from the respective patient medical service delivery station, simultaneously displaying both the real-time near and far video images of the patient, the electronic medical record of the patient, and auxiliary data to the remote physician when the remote physician is providing remote physician medical services through operation of the remote physician medical service delivery suite with the respective patient medical service delivery station.

* * * * *

UNITED STATES PATENT AND TRADEMARK OFFICE
CERTIFICATE OF CORRECTION

| | | |
|---|---|---|
| PATENT NO. | : 7,912,733 B2 | Page 1 of 1 |
| APPLICATION NO. | : 11/415936 | |
| DATED | : March 22, 2011 | |
| INVENTOR(S) | : Leon M. Clements et al. | |

It is certified that error appears in the above-identified patent and that said Letters Patent is hereby corrected as shown below:

Column 51, line 58, after the word "claim," delete the number "3", insert -- 32 --;

Column 55, line 23, cancel the text beginning with "providing data to display a real-time near video image" to and ending "second video display screen of the remote physician medical service delivery suite," and insert the following claim elements:
--providing data to display a real-time near video image of the selected patient received from the
    respective patient medical service delivery station on the first video display screen of the
    remote physician medical service delivery suite,
providing data to display a real-time far video image of the preselected patient received from the
    respective patient medical service delivery station on the second video display screen of the
    remote physician medical service delivery suite,--.

Signed and Sealed this
Sixth Day of September, 2011

David J. Kappos
*Director of the United States Patent and Trademark Office*